(12) United States Patent
Freitag et al.

(10) Patent No.: US 8,381,729 B2
(45) Date of Patent: *Feb. 26, 2013

(54) METHODS AND DEVICES FOR MINIMALLY INVASIVE RESPIRATORY SUPPORT

(75) Inventors: Lutz Freitag, Hemer (DE); Anthony Wondka, Thousand Oaks, CA (US); Gregory Kapust, San Ramon, CA (US); Robert Bryan, San Ramon, CA (US); Michael Khenansho, Modesto, CA (US); Anthony Gerber, San Francisco, CA (US)

(73) Assignee: Breathe Technologies, Inc., Irvine, CA (US)

( * ) Notice: Subject to any disclaimer, the term of this patent is extended or adjusted under 35 U.S.C. 154(b) by 1378 days.

This patent is subject to a terminal disclaimer.

(21) Appl. No.: 11/882,530

(22) Filed: Aug. 3, 2007

(65) Prior Publication Data

US 2008/0135044 A1 Jun. 12, 2008

Related U.S. Application Data

(63) Continuation-in-part of application No. 10/567,746, filed as application No. PCT/DE2004/001646 on Jul. 23, 2004, now abandoned, and a continuation-in-part of application No. 10/870,849, filed on Jun. 17, 2004, now Pat. No. 7,588,033, and a continuation-in- (Continued)

(30) Foreign Application Priority Data

Aug. 11, 2003 (DE) .................. 103 37 138

(51) Int. Cl.
*A62B 9/00* (2006.01)

(52) U.S. Cl. .............................. 128/207.14; 128/207.16
(58) Field of Classification Search ............. 128/200.26, 128/207.14, 207.15, 207.16; 604/516, 518, 604/514, 509, 48, 28, 35; 424/423; 607/99; 600/114, 116; 606/108
See application file for complete search history.

(56) References Cited

U.S. PATENT DOCUMENTS

| 50,641 A | 10/1865 | Stone |
|---|---|---|
| 428,592 A | 5/1890 | Chapman |
| 697,181 A | 4/1902 | Smith |
| 718,785 A | 1/1903 | McNary |
| 853,439 A | 5/1907 | Clark |
| 859,156 A | 7/1907 | Warnken |
| 909,002 A | 1/1909 | Lambert |

(Continued)

FOREIGN PATENT DOCUMENTS

| CA | 2535450 | 2/2005 |
|---|---|---|
| CN | 200480029872 | 9/2006 |

(Continued)

OTHER PUBLICATIONS

U.S. Appl. No. 60/924,514 (co-pending), filed May 18, 2007, Wondka et al.

(Continued)

*Primary Examiner* — Steven Douglas
(74) *Attorney, Agent, or Firm* — Stetina Brunda Garred & Brucker

(57) ABSTRACT

Modes, methods, systems and devices are described for providing assisted ventilation to a patient, including wearable ventilation systems with integral gas supplies, special gas supply features, ventilation catheters and access devices, and breath sensing techniques.

154 Claims, 25 Drawing Sheets

Related U.S. Application Data part of application No. 10/771,803, filed on Feb. 4, 2004, now Pat. No. 7,487,778.

(60) Provisional application No. 60/835,066, filed on Aug. 3, 2006, provisional application No. 60/479,213, filed on Jun. 18, 2003.

(56) References Cited

U.S. PATENT DOCUMENTS

| | | | |
|---|---|---|---|
| 1,125,542 | A | 1/1915 | Humphries |
| 1,129,619 | A | 2/1915 | Zapf |
| 1,331,297 | A | 2/1920 | Walker |
| 2,178,800 | A | 11/1939 | Lombard |
| 2,259,817 | A | 10/1941 | Hawkins |
| 2,552,595 | A | 5/1951 | Seeler |
| 2,663,297 | A | 12/1953 | Turnberg |
| 2,693,800 | A | 11/1954 | Caldwell |
| 2,735,432 | A | 2/1956 | Hudson |
| 2,792,000 | A | 5/1957 | Richardson |
| 2,843,122 | A | 7/1958 | Hudson |
| 2,859,748 | A | 11/1958 | Hudson |
| 2,931,358 | A | 4/1960 | Sheridan |
| 2,947,938 | A | 8/1960 | Bennett |
| 3,172,407 | A | 3/1965 | Von Pechmann |
| 3,267,935 | A | 8/1966 | Andreasen et al. |
| 3,319,627 | A | 5/1967 | Windsor |
| 3,357,424 | A | 12/1967 | Schreiber |
| 3,357,427 | A | 12/1967 | Schreiber |
| 3,357,428 | A | 12/1967 | Carlson |
| 3,437,274 | A | 4/1969 | Apri |
| 3,460,533 | A | 8/1969 | Riú Plá |
| 3,493,703 | A | 2/1970 | Finan |
| 3,513,844 | A | 5/1970 | Smith |
| 3,610,247 | A | 10/1971 | Jackson |
| 3,625,206 | A | 12/1971 | Charnley |
| 3,625,207 | A | 12/1971 | Agnew |
| 3,631,438 | A | 12/1971 | Lewin |
| 3,643,660 | A | 2/1972 | Hudson et al. |
| 3,657,740 | A | 4/1972 | Cialone |
| 3,682,171 | A | 8/1972 | Dali et al. |
| 3,721,233 | A | 3/1973 | Montgomery et al. |
| 3,726,275 | A | 4/1973 | Jackson et al. |
| 3,727,606 | A | 4/1973 | Sielaff |
| 3,733,008 | A | 5/1973 | Churchill et al. |
| 3,741,208 | A | 6/1973 | Jonsson et al. |
| 3,754,552 | A | 8/1973 | King |
| 3,794,026 | A | 2/1974 | Jacobs |
| 3,794,072 | A | 2/1974 | Diedrich et al. |
| 3,802,431 | A | 4/1974 | Farr |
| 3,831,596 | A | 8/1974 | Cavallo |
| 3,881,480 | A | 5/1975 | Lafourcade |
| 3,896,800 | A | 7/1975 | Cibulka |
| 3,903,881 | A | 9/1975 | Weigl |
| 3,905,362 | A | 9/1975 | Eyrick et al. |
| 3,949,749 | A | 4/1976 | Stewart |
| 3,951,143 | A | 4/1976 | Kitrilakis et al. |
| 3,961,627 | A | 6/1976 | Ernst et al. |
| 3,972,327 | A | 8/1976 | Ernst et al. |
| 3,985,131 | A | 10/1976 | Buck et al. |
| 3,991,790 | A | 11/1976 | Russell |
| 4,003,377 | A | 1/1977 | Dahl |
| 4,036,253 | A | 7/1977 | Fegan et al. |
| 4,054,133 | A | 10/1977 | Myers |
| 4,067,328 | A | 1/1978 | Manley |
| 4,106,505 | A | 8/1978 | Salter et al. |
| 4,146,885 | A | 3/1979 | Lawson, Jr. |
| 4,206,754 | A | 6/1980 | Cox et al. |
| 4,211,086 | A | 7/1980 | Leonard et al. |
| 4,216,769 | A | 8/1980 | Grimes |
| 4,231,363 | A | 11/1980 | Grimes |
| 4,231,365 | A | 11/1980 | Scarberry |
| 4,256,101 | A | 3/1981 | Ellestad |
| 4,261,355 | A | 4/1981 | Glazener |
| 4,263,908 | A | 4/1981 | Mizerak |
| 4,265,237 | A | 5/1981 | Schwanbom et al. |
| 4,266,540 | A | 5/1981 | Panzik et al. |
| 4,273,124 | A | 6/1981 | Zimmerman |
| 4,274,162 | A | 6/1981 | Joy et al. |
| 4,278,082 | A | 7/1981 | Blackmer |
| 4,282,869 | A | 8/1981 | Zidulka |
| 4,306,567 | A | 12/1981 | Krasner |
| 4,323,064 | A | 4/1982 | Hoenig et al. |
| 4,354,488 | A | 10/1982 | Bartos |
| 4,365,636 | A | 12/1982 | Barker |
| 4,367,735 | A | 1/1983 | Dali |
| 4,377,162 | A | 3/1983 | Staver |
| 4,393,869 | A | 7/1983 | Boyarsky et al. |
| 4,406,283 | A | 9/1983 | Bir |
| 4,411,267 | A | 10/1983 | Heyman |
| 4,413,514 | A | 11/1983 | Bowman |
| 4,421,113 | A | 12/1983 | Gedeon et al. |
| 4,422,456 | A | 12/1983 | Tiep |
| 4,449,523 | A | 5/1984 | Szachowicz et al. |
| 4,454,880 | A | 6/1984 | Muto et al. |
| 4,462,398 | A | 7/1984 | Durkan et al. |
| 4,469,097 | A | 9/1984 | Kelman |
| 4,481,944 | A | 11/1984 | Bunnell |
| 4,488,548 | A | 12/1984 | Agdanowski |
| 4,495,946 | A | 1/1985 | Lemer |
| 4,506,666 | A | 3/1985 | Durkan |
| 4,506,667 | A | 3/1985 | Ansite |
| 4,519,387 | A | 5/1985 | Durkan et al. |
| 4,520,812 | A | 6/1985 | Freitag et al. |
| 4,527,557 | A | 7/1985 | DeVries et al. |
| 4,535,766 | A | 8/1985 | Baum et al. |
| 4,537,188 | A | 8/1985 | Phuc |
| 4,539,984 | A | 9/1985 | Kiszel et al. |
| 4,559,940 | A | 12/1985 | McGinnis |
| 4,570,631 | A | 2/1986 | Durkan |
| 4,571,741 | A | 2/1986 | Guillaumot |
| 4,584,996 | A | 4/1986 | Blum |
| 4,590,951 | A | 5/1986 | O'Connor |
| 4,592,349 | A | 6/1986 | Bird |
| 4,621,632 | A | 11/1986 | Bartels et al. |
| 4,630,606 | A | 12/1986 | Weerda et al. |
| 4,630,614 | A | 12/1986 | Atlas |
| 4,644,947 | A | 2/1987 | Whitwam et al. |
| 4,648,395 | A | 3/1987 | Sato et al. |
| 4,648,398 | A | 3/1987 | Agdanowski et al. |
| 4,658,832 | A | 4/1987 | Brugnoli |
| 4,660,555 | A | 4/1987 | Payton |
| 4,682,591 | A | 7/1987 | Jones |
| 4,684,398 | A | 8/1987 | Dunbar et al. |
| 4,686,974 | A | 8/1987 | Sato et al. |
| 4,686,975 | A | 8/1987 | Naimon et al. |
| 4,688,961 | A | 8/1987 | Shioda et al. |
| 4,705,034 | A | 11/1987 | Perkins |
| 4,744,356 | A | 5/1988 | Greenwood |
| 4,747,403 | A | 5/1988 | Gluck et al. |
| 4,753,233 | A | 6/1988 | Grimes |
| 4,773,411 | A | 9/1988 | Downs |
| 4,776,333 | A | 10/1988 | Miyamae |
| 4,782,832 | A | 11/1988 | Trimble et al. |
| 4,784,130 | A | 11/1988 | Kenyon et al. |
| 4,803,981 | A | 2/1989 | Vickery |
| 4,807,616 | A | 2/1989 | Adahan |
| 4,807,617 | A | 2/1989 | Nesti |
| 4,808,160 | A | 2/1989 | Timmons et al. |
| 4,813,431 | A | 3/1989 | Brown |
| 4,817,897 | A | 4/1989 | Kreusel |
| 4,818,320 | A | 4/1989 | Weichselbaum |
| 4,823,788 | A | 4/1989 | Smith et al. |
| 4,825,859 | A | 5/1989 | Lambert |
| 4,827,922 | A | 5/1989 | Champain et al. |
| 4,832,014 | A | 5/1989 | Perkins |
| 4,838,255 | A | 6/1989 | Lambert |
| 4,841,953 | A | 6/1989 | Dodrill |
| 4,848,333 | A | 7/1989 | Waite |
| 4,850,350 | A | 7/1989 | Jackson |
| 4,865,586 | A | 9/1989 | Hedberg |
| 4,869,718 | A | 9/1989 | Brader |
| 4,899,740 | A | 2/1990 | Napolitano |
| 4,905,688 | A | 3/1990 | Vicenzi et al. |
| 4,915,103 | A | 4/1990 | Visveshwara et al. |

| Patent | Date | Name |
|---|---|---|
| 4,915,105 A | 4/1990 | Lee |
| 4,919,128 A | 4/1990 | Kopala et al. |
| 4,919,132 A | 4/1990 | Miser |
| 4,932,401 A | 6/1990 | Perkins |
| 4,938,212 A | 7/1990 | Snook et al. |
| 4,944,310 A | 7/1990 | Sullivan |
| 4,967,743 A | 11/1990 | Lambert |
| 4,971,049 A | 11/1990 | Rotariu et al. |
| 4,982,735 A | 1/1991 | Yagata et al. |
| 4,986,269 A | 1/1991 | Hakkinen |
| 4,989,599 A | 2/1991 | Carter |
| 4,990,157 A | 2/1991 | Roberts et al. |
| 5,000,175 A | 3/1991 | Pue |
| 5,002,050 A | 3/1991 | McGinnis |
| 5,005,570 A | 4/1991 | Perkins |
| 5,018,519 A | 5/1991 | Brown |
| 5,022,394 A | 6/1991 | Chmielinski |
| 5,024,219 A | 6/1991 | Dietz |
| 5,025,805 A | 6/1991 | Nutter |
| 5,038,771 A | 8/1991 | Dietz |
| 5,042,478 A | 8/1991 | Kopala et al. |
| 5,046,491 A | 9/1991 | Derrick |
| 5,046,492 A | 9/1991 | Stackhouse et al. |
| 5,048,515 A | 9/1991 | Sanso |
| 5,048,516 A | 9/1991 | Soderberg |
| 5,052,400 A | 10/1991 | Dietz |
| 5,054,484 A | 10/1991 | Hebeler, Jr. |
| 5,058,580 A | 10/1991 | Hazard |
| 5,074,299 A | 12/1991 | Dietz |
| 5,076,267 A | 12/1991 | Pasternack |
| 5,090,408 A | 2/1992 | Spofford et al. |
| 5,097,827 A | 3/1992 | Izumi |
| 5,099,836 A | 3/1992 | Rowland et al. |
| 5,099,837 A | 3/1992 | Russel, Sr. et al. |
| 5,101,820 A | 4/1992 | Christopher |
| 5,103,815 A | 4/1992 | Siegel et al. |
| 5,105,807 A | 4/1992 | Kahn et al. |
| 5,107,830 A | 4/1992 | Younes |
| 5,107,831 A | 4/1992 | Halpern et al. |
| 5,113,857 A | 5/1992 | Dickerman et al. |
| 5,117,818 A | 6/1992 | Palfy |
| 5,117,819 A | 6/1992 | Servidio et al. |
| 5,127,400 A | 7/1992 | DeVries et al. |
| 5,134,995 A | 8/1992 | Gruenke et al. |
| 5,134,996 A | 8/1992 | Bell |
| 5,140,045 A | 8/1992 | Askanazi et al. |
| 5,148,802 A | 9/1992 | Sanders et al. |
| 5,161,525 A | 11/1992 | Kimm et al. |
| 5,165,397 A | 11/1992 | Arp |
| 5,181,509 A | 1/1993 | Spofford et al. |
| 5,184,610 A | 2/1993 | Marten et al. |
| 5,186,167 A | 2/1993 | Kolobow |
| 5,193,532 A | 3/1993 | Moa et al. |
| 5,193,533 A | 3/1993 | Body et al. |
| 5,199,424 A | 4/1993 | Sullivan et al. |
| 5,211,170 A | 5/1993 | Press |
| 5,217,008 A | 6/1993 | Lindholm |
| 5,233,978 A | 8/1993 | Callaway |
| 5,233,979 A | 8/1993 | Strickland |
| 5,239,994 A | 8/1993 | Atkins |
| 5,239,995 A | 8/1993 | Estes et al. |
| 5,243,972 A | 9/1993 | Huang |
| 5,245,995 A | 9/1993 | Sullivan et al. |
| 5,255,675 A | 10/1993 | Kolobow |
| 5,258,027 A | 11/1993 | Berghaus |
| 5,269,296 A | 12/1993 | Landis |
| 5,271,388 A | 12/1993 | Whitwam et al. |
| 5,271,391 A | 12/1993 | Graves |
| 5,275,159 A | 1/1994 | Griebel |
| 5,279,288 A | 1/1994 | Christopher |
| 5,287,852 A | 2/1994 | Arkinstall et al. |
| 5,303,698 A | 4/1994 | Tobia et al. |
| 5,303,700 A | 4/1994 | Weismann et al. |
| 5,318,019 A | 6/1994 | Celaya |
| 5,331,995 A | 7/1994 | Westfall et al. |
| 5,335,656 A | 8/1994 | Bowe et al. |
| 5,339,809 A | 8/1994 | Beck, Jr. et al. |
| 5,349,946 A | 9/1994 | McComb |
| 5,368,017 A | 11/1994 | Sorenson et al. |
| 5,370,112 A | 12/1994 | Perkins |
| 5,373,842 A | 12/1994 | Olsson et al. |
| 5,375,593 A | 12/1994 | Press |
| 5,388,575 A | 2/1995 | Taube |
| 5,394,870 A | 3/1995 | Johansson |
| 5,398,676 A | 3/1995 | Press et al. |
| 5,398,682 A | 3/1995 | Lynn |
| 5,400,778 A | 3/1995 | Jonson et al. |
| 5,419,314 A | 5/1995 | Christopher |
| 5,438,979 A | 8/1995 | Johnson, Jr. et al. |
| 5,438,980 A | 8/1995 | Phillips |
| 5,443,075 A | 8/1995 | Holscher |
| 5,460,174 A | 10/1995 | Chang |
| 5,460,613 A | 10/1995 | Ulrich et al. |
| 5,474,062 A | 12/1995 | DeVires et al. |
| 5,477,852 A | 12/1995 | Landis et al. |
| 5,485,850 A | 1/1996 | Dietz |
| 5,490,502 A | 2/1996 | Rapoport et al. |
| 5,503,146 A | 4/1996 | Froehlich et al. |
| 5,503,497 A | 4/1996 | Dudley et al. |
| 5,507,282 A | 4/1996 | Younes |
| 5,509,409 A | 4/1996 | Weatherholt |
| 5,513,628 A | 5/1996 | Coles et al. |
| 5,513,631 A | 5/1996 | McWilliams |
| 5,513,635 A | 5/1996 | Bedi |
| 5,522,382 A | 6/1996 | Sullivan et al. |
| 5,526,806 A | 6/1996 | Sansoni |
| 5,529,060 A | 6/1996 | Salmon et al. |
| 5,533,506 A | 7/1996 | Wood |
| 5,535,738 A | 7/1996 | Estes et al. |
| 5,537,997 A | 7/1996 | Mechlenburg et al. |
| 5,538,002 A | 7/1996 | Boussignac et al. |
| 5,542,415 A | 8/1996 | Brody |
| 5,546,935 A | 8/1996 | Champeau |
| 5,549,106 A | 8/1996 | Gruenke et al. |
| 5,551,419 A | 9/1996 | Froehlich et al. |
| 5,558,086 A | 9/1996 | Smith et al. |
| 5,564,416 A | 10/1996 | Jones |
| 5,575,282 A | 11/1996 | Knoch et al. |
| 5,582,164 A | 12/1996 | Sanders |
| 5,593,143 A | 1/1997 | Ferrarin |
| 5,595,174 A | 1/1997 | Gwaltney |
| 5,598,837 A | 2/1997 | Sirianne, Jr. et al. |
| 5,598,840 A | 2/1997 | Iund et al. |
| 5,603,315 A | 2/1997 | Sasso, Jr. |
| 5,605,148 A | 2/1997 | Jones |
| 5,626,131 A | 5/1997 | Chua et al. |
| 5,632,269 A | 5/1997 | Zdrojkowski |
| 5,636,630 A | 6/1997 | Miller et al. |
| 5,645,053 A | 7/1997 | Remmers et al. |
| 5,645,054 A | 7/1997 | Cotner et al. |
| 5,647,351 A | 7/1997 | Weismann et al. |
| 5,669,377 A | 9/1997 | Fenn |
| 5,669,380 A | 9/1997 | Garry et al. |
| 5,676,132 A | 10/1997 | Tillotson et al. |
| 5,676,135 A | 10/1997 | McClean |
| 5,682,878 A | 11/1997 | Ogden |
| 5,682,881 A | 11/1997 | Winthrop et al. |
| 5,687,713 A | 11/1997 | Bahr et al. |
| 5,687,714 A | 11/1997 | Kolobow et al. |
| 5,687,715 A | 11/1997 | Landis et al. |
| 5,690,097 A | 11/1997 | Howard et al. |
| 5,692,497 A | 12/1997 | Schnitzer et al. |
| 5,697,364 A | 12/1997 | Chua et al. |
| 5,704,345 A | 1/1998 | Berthon-Jones |
| 5,711,296 A | 1/1998 | Kolobow |
| 5,715,812 A | 2/1998 | Deighan et al. |
| 5,715,815 A | 2/1998 | Lorenzen et al. |
| 5,720,278 A | 2/1998 | Lachmann et al. |
| 5,735,268 A | 4/1998 | Chua et al. |
| 5,735,272 A | 4/1998 | Dillon et al. |
| 5,740,796 A | 4/1998 | Skog |
| 5,752,511 A | 5/1998 | Simmons et al. |
| 5,762,638 A | 6/1998 | Shikani et al. |
| 5,791,337 A | 8/1998 | Coles et al. |
| 5,819,723 A | 10/1998 | Joseph |
| 5,826,579 A | 10/1998 | Remmers et al. |
| 5,845,636 A | 12/1998 | Gruenke et al. |
| 5,865,173 A | 2/1999 | Froehlich |

| | | | | | | |
|---|---|---|---|---|---|---|
| 5,865,174 | A | 2/1999 | Kloeppel | 6,418,928 | B1 | 7/2002 | Bordewick et al. |
| 5,881,723 | A | 3/1999 | Wallace et al. | 6,422,240 | B1 | 7/2002 | Levitsky et al. |
| 5,904,648 | A | 5/1999 | Arndt et al. | 6,423,001 | B1 | 7/2002 | Abreu |
| 5,906,204 | A | 5/1999 | Beran et al. | 6,427,690 | B1 | 8/2002 | McCombs et al. |
| 5,911,756 | A | 6/1999 | Debry | 6,431,172 | B1 | 8/2002 | Bordewick |
| 5,915,379 | A | 6/1999 | Wallace et al. | 6,439,228 | B1 | 8/2002 | Hete et al. |
| 5,915,381 | A | 6/1999 | Nord | 6,439,229 | B1 | 8/2002 | Du et al. |
| 5,918,597 | A | 7/1999 | Jones et al. | 6,439,234 | B1 | 8/2002 | Curti et al. |
| 5,921,238 | A | 7/1999 | Bourdon | 6,439,235 | B1 | 8/2002 | Larquet et al. |
| 5,921,942 | A | 7/1999 | Remmers et al. | 6,450,164 | B1 | 9/2002 | Banner et al. |
| 5,921,952 | A | 7/1999 | Desmond, III et al. | 6,450,166 | B1 | 9/2002 | McDonald et al. |
| 5,927,276 | A | 7/1999 | Rodriguez | 6,457,472 | B1 | 10/2002 | Schwartz et al. |
| 5,928,189 | A | 7/1999 | Phillips et al. | 6,467,477 | B1 | 10/2002 | Frank et al. |
| 5,931,160 | A | 8/1999 | Gilmore et al. | 6,478,026 | B1 | 11/2002 | Wood |
| 5,931,162 | A | 8/1999 | Christian | 6,494,202 | B2 | 12/2002 | Farmer |
| 5,937,853 | A | 8/1999 | Strom | 6,494,206 | B1 | 12/2002 | Bergamaschi et al. |
| 5,937,855 | A | 8/1999 | Zdrojkowski et al. | 6,505,623 | B1 | 1/2003 | Hansen |
| 5,938,118 | A | 8/1999 | Cooper | 6,505,624 | B1 | 1/2003 | Campbell, Sr. |
| 5,954,050 | A | 9/1999 | Christopher | 6,516,801 | B2 | 2/2003 | Boussignac |
| 5,957,136 | A | 9/1999 | Magidson et al. | 6,520,176 | B1 | 2/2003 | Dubois et al. |
| 5,964,223 | A | 10/1999 | Baran | 6,520,183 | B2 | 2/2003 | Amar |
| 5,975,077 | A | 11/1999 | Hofsteffer et al. | 6,530,373 | B1 | 3/2003 | Patron et al. |
| 5,975,081 | A | 11/1999 | Hood et al. | 6,532,958 | B1 | 3/2003 | Buan et al. |
| 5,979,440 | A | 11/1999 | Honkonen et al. | 6,532,960 | B1 | 3/2003 | Yurko |
| 5,989,193 | A | 11/1999 | Sullivan | 6,536,432 | B2 | 3/2003 | Truschel |
| 6,000,396 | A | 12/1999 | Melker et al. | 6,536,436 | B1 | 3/2003 | McGlothen |
| 6,019,101 | A | 2/2000 | Cotner et al. | 6,550,478 | B2 | 4/2003 | Remmers et al. |
| 6,039,696 | A | 3/2000 | Bell | 6,553,992 | B1 | 4/2003 | Berthon-Jones et al. |
| 6,050,260 | A | 4/2000 | Daniell et al. | 6,561,188 | B1 | 5/2003 | Ellis |
| 6,076,519 | A | 6/2000 | Johnson | 6,561,193 | B1 | 5/2003 | Noble |
| 6,085,747 | A | 7/2000 | Axe et al. | 6,564,797 | B1 | 5/2003 | Mechlenburg et al. |
| 6,091,973 | A | 7/2000 | Colla et al. | 6,564,800 | B1 | 5/2003 | Olivares |
| 6,093,169 | A | 7/2000 | Cardoso | 6,568,391 | B1 | 5/2003 | Tatarek et al. |
| 6,105,575 | A | 8/2000 | Estes et al. | 6,571,794 | B1 | 6/2003 | Hansen |
| 6,109,264 | A | 8/2000 | Sauer | 6,571,796 | B2 * | 6/2003 | Banner et al. ............ 128/204.26 |
| 6,112,746 | A | 9/2000 | Kwok et al. | 6,571,798 | B1 | 6/2003 | Thornton |
| 6,119,694 | A | 9/2000 | Correa et al. | 6,575,159 | B1 | 6/2003 | Frye et al. |
| 6,120,460 | A | 9/2000 | Abreu | 6,575,944 | B1 | 6/2003 | McNary et al. |
| 6,123,668 | A | 9/2000 | Abreu | 6,584,973 | B1 | 7/2003 | Biondi et al. |
| 6,131,571 | A | 10/2000 | Lampotang et al. | 6,588,422 | B1 | 7/2003 | Berthon-Jones et al. |
| 6,135,970 | A | 10/2000 | Kadhiresan et al. | 6,588,423 | B1 | 7/2003 | Sinderby |
| 6,152,132 | A | 11/2000 | Psaros | 6,591,834 | B1 | 7/2003 | Colla et al. |
| 6,152,134 | A | 11/2000 | Webber et al. | 6,591,835 | B1 | 7/2003 | Blanch |
| 6,158,432 | A | 12/2000 | Biondi et al. | 6,595,207 | B1 | 7/2003 | McDonald et al. |
| 6,192,883 | B1 | 2/2001 | Miller, Jr. | 6,595,215 | B2 | 7/2003 | Wood |
| 6,203,502 | B1 | 3/2001 | Hilgendorf et al. | 6,609,517 | B1 | 8/2003 | Estes et al. |
| 6,213,119 | B1 | 4/2001 | Brydon et al. | 6,622,726 | B1 | 9/2003 | Du |
| 6,213,955 | B1 | 4/2001 | Karakasoglu et al. | 6,626,174 | B1 | 9/2003 | Genger et al. |
| 6,220,244 | B1 | 4/2001 | Mclaughlin | 6,626,175 | B2 | 9/2003 | Jafari et al. |
| 6,224,560 | B1 | 5/2001 | Gazula et al. | 6,629,525 | B2 | 10/2003 | Hill et al. |
| 6,227,200 | B1 | 5/2001 | Crump et al. | 6,629,527 | B1 | 10/2003 | Estes et al. |
| 6,247,470 | B1 | 6/2001 | Ketchedjian | 6,629,529 | B2 | 10/2003 | Arnott |
| 6,269,811 | B1 | 8/2001 | Duff et al. | 6,631,919 | B1 | 10/2003 | West et al. |
| 6,269,812 | B1 | 8/2001 | Wallace et al. | 6,634,356 | B1 | 10/2003 | O'Dea et al. |
| 6,273,859 | B1 | 8/2001 | Remmers et al. | 6,635,021 | B1 | 10/2003 | Sullivan et al. |
| 6,286,508 | B1 | 9/2001 | Remmers et al. | 6,640,806 | B2 | 11/2003 | Yurko |
| D449,376 | S | 10/2001 | McDonald et al. | 6,644,305 | B2 | 11/2003 | MacRae et al. |
| D449,883 | S | 10/2001 | McDonald et al. | 6,644,311 | B1 | 11/2003 | Truitt et al. |
| 6,298,850 | B1 | 10/2001 | Argraves | 6,644,315 | B2 | 11/2003 | Ziaee |
| 6,305,374 | B1 | 10/2001 | Zdrojkowski et al. | 6,651,653 | B1 | 11/2003 | Honkonen et al. |
| 6,314,957 | B1 | 11/2001 | Boissin et al. | 6,651,656 | B2 | 11/2003 | Demers et al. |
| 6,315,739 | B1 | 11/2001 | Merilainen et al. | 6,651,658 | B1 | 11/2003 | Hill et al. |
| D451,598 | S | 12/2001 | McDonald et al. | 6,655,382 | B1 | 12/2003 | Kolobow |
| 6,328,038 | B1 | 12/2001 | Kessler et al. | 6,655,385 | B1 | 12/2003 | Curti et al. |
| 6,328,753 | B1 | 12/2001 | Zammit | 6,666,208 | B1 | 12/2003 | Schumacher et al. |
| 6,332,463 | B1 | 12/2001 | Farrugia et al. | 6,668,828 | B1 | 12/2003 | Figley et al. |
| 6,345,619 | B1 | 2/2002 | Finn | 6,668,829 | B1 | 12/2003 | Biondi et al. |
| 6,357,438 | B1 | 3/2002 | Hansen | 6,669,712 | B1 | 12/2003 | Cardoso |
| 6,357,440 | B1 | 3/2002 | Hansen et al. | 6,675,796 | B2 | 1/2004 | McDonald |
| 6,360,741 | B2 | 3/2002 | Truschel | 6,675,801 | B2 | 1/2004 | Wallace et al. |
| 6,360,745 | B1 | 3/2002 | Wallace et al. | 6,679,265 | B2 | 1/2004 | Strickland et al. |
| 6,363,933 | B1 | 4/2002 | Berthon-Jones | 6,681,764 | B1 | 1/2004 | Honkonen et al. |
| 6,367,474 | B1 | 4/2002 | Berthon-Jones et al. | 6,684,883 | B1 | 2/2004 | Burns |
| 6,369,838 | B1 | 4/2002 | Wallace et al. | 6,691,702 | B2 | 2/2004 | Appel et al. |
| 6,371,114 | B1 | 4/2002 | Schmidt et al. | 6,691,707 | B1 | 2/2004 | Gunaratnam et al. |
| 6,378,520 | B1 | 4/2002 | Davenport | 6,694,973 | B1 | 2/2004 | Dunhao et al. |
| 6,390,091 | B1 | 5/2002 | Banner et al. | 6,694,978 | B1 | 2/2004 | Bennarsten |
| 6,394,088 | B1 | 5/2002 | Frye et al. | 6,698,423 | B1 | 3/2004 | Honkonen et al. |
| 6,398,739 | B1 | 6/2002 | Sullivan et al. | 6,705,314 | B1 | 3/2004 | O'dea |

| | | | | | | |
|---|---|---|---|---|---|---|
| 6,705,315 B2 | 3/2004 | Sullivan et al. | | 7,121,277 B2 | 10/2006 | Ström |
| 6,722,360 B2 | 4/2004 | Doshi | | 7,128,578 B2 | 10/2006 | Lampotang et al. |
| 6,722,362 B2 | 4/2004 | Hete et al. | | 7,152,598 B2 | 12/2006 | Morris et al. |
| 6,742,517 B1 | 6/2004 | Frye et al. | | 7,152,604 B2 | 12/2006 | Hickle et al. |
| 6,745,768 B2 | 6/2004 | Colla et al. | | 7,156,090 B2 | 1/2007 | Nomori Hiroaki |
| 6,752,150 B1 | 6/2004 | Remmers et al. | | 7,156,097 B2 | 1/2007 | Cardoso |
| 6,752,151 B2 | 6/2004 | Hill | | 7,162,296 B2 | 1/2007 | Leonhardt et al. |
| 6,752,152 B2 | 6/2004 | Gale et al. | | 7,168,429 B2 | 1/2007 | Matthews et al. |
| 6,755,193 B2 | 6/2004 | Berthon-Jones et al. | | 7,188,621 B2 | 3/2007 | DeVries et al. |
| 6,758,217 B1 | 7/2004 | Younes | | 7,188,624 B2 | 3/2007 | Wood |
| 6,761,172 B2 | 7/2004 | Boussignac et al. | | 7,195,016 B2 | 3/2007 | Loyd et al. |
| 6,763,832 B1 | 7/2004 | Kirsch et al. | | 7,195,018 B1 | 3/2007 | Goldstein |
| 6,769,432 B1 | 8/2004 | Keifer | | 7,201,169 B2 | 4/2007 | Wilkie et al. |
| 6,776,162 B2 | 8/2004 | Wood | | 7,201,269 B2 | 4/2007 | Buscher et al. |
| 6,776,163 B2 | 8/2004 | Dougill et al. | | D542,912 S | 5/2007 | Gunaratnam et al. |
| 6,789,539 B2 | 9/2004 | Martinez | | 7,222,623 B2 | 5/2007 | Devries et al. |
| 6,796,305 B1 | 9/2004 | Banner et al. | | 7,225,811 B2 | 6/2007 | Ruiz et al. |
| 6,799,575 B1 | 10/2004 | Carter | | 7,234,465 B2 | 6/2007 | Wood |
| 6,805,126 B2 | 10/2004 | Dutkiewicz | | 7,237,205 B2 | 6/2007 | Sarel |
| 6,807,966 B2 | 10/2004 | Wright | | 7,246,620 B2 | 7/2007 | Conroy, Jr. |
| 6,807,967 B2 | 10/2004 | Wood | | D549,323 S | 8/2007 | Kwok et al. |
| 6,810,876 B2 | 11/2004 | Berthon-jones | | 7,255,103 B2 | 8/2007 | Bassin |
| 6,814,073 B2 | 11/2004 | Wickham | | 7,255,107 B1 | 8/2007 | Gomez |
| 6,814,077 B1 | 11/2004 | Eistert | | 7,267,122 B2 | 9/2007 | Hill |
| 6,823,866 B2 | 11/2004 | Jafari et al. | | 7,267,123 B2 | 9/2007 | Aylsworth et al. |
| 6,827,340 B2 | 12/2004 | Austin et al. | | 7,270,126 B2 | 9/2007 | Wallace et al. |
| 6,837,238 B2 | 1/2005 | McDonald | | 7,270,128 B2 | 9/2007 | Berthon-Jones et al. |
| 6,840,240 B1 | 1/2005 | Berthon-Jones et al. | | 7,296,569 B2 | 11/2007 | Frye et al. |
| 6,843,247 B2 | 1/2005 | Frye et al. | | 7,296,573 B2 | 11/2007 | Estes et al. |
| 6,848,446 B2 | 2/2005 | Noble | | D557,802 S | 12/2007 | Miceli, Jr. et al. |
| 6,854,462 B2 | 2/2005 | Berthon-Jones et al. | | 7,302,950 B2 | 12/2007 | Berthon-Jones et al. |
| 6,863,069 B2 | 3/2005 | Wood | | 7,305,987 B2 | 12/2007 | Scholler et al. |
| 6,866,041 B2 | 3/2005 | Hardy, Jr. et al. | | 7,318,437 B2 | 1/2008 | Gunaratnam et al. |
| 6,877,511 B2 | 4/2005 | Devries et al. | | 7,320,321 B2 | 1/2008 | Pranger et al. |
| 6,880,556 B2 | 4/2005 | Uchiyama et al. | | 7,328,703 B1 | 2/2008 | Tiep |
| 6,910,480 B1 | 6/2005 | Berthon-Jones | | 7,353,826 B2 | 4/2008 | Sleeper et al. |
| 6,910,482 B2 | 6/2005 | Bliss et al. | | 7,367,337 B2 | 5/2008 | Berthon-Jones et al. |
| 6,910,510 B2 | 6/2005 | Gale et al. | | 7,370,652 B2 | 5/2008 | Matula, Jr. et al. |
| 6,913,601 B2 | 7/2005 | St. Goar et al. | | 7,373,939 B1 | 5/2008 | DuBois et al. |
| 6,915,803 B2 | 7/2005 | Berthon-Jones et al. | | 7,406,966 B2 | 8/2008 | Wondka |
| 6,920,875 B1 | 7/2005 | Hill et al. | | 7,418,965 B2 | 9/2008 | Fukunaga et al. |
| 6,920,877 B2 | 7/2005 | Remmers et al. | | 7,422,015 B2 | 9/2008 | Delisle et al. |
| 6,920,878 B2 | 7/2005 | Sinderby et al. | | 7,431,035 B2 | 10/2008 | Mizuta et al. |
| 6,932,084 B2 | 8/2005 | Estes et al. | | 7,451,762 B2 | 11/2008 | Chua et al. |
| 6,938,619 B1 | 9/2005 | Hickle | | 7,455,717 B2 | 11/2008 | Sprinkle |
| 6,938,620 B2 | 9/2005 | Payne, Jr. | | 7,461,656 B2 | 12/2008 | Gunaratnam et al. |
| 6,941,950 B2 | 9/2005 | Wilson et al. | | 7,468,040 B2 | 12/2008 | Hartley et al. |
| 6,948,497 B2 | 9/2005 | Zdrojkowski et al. | | 7,469,697 B2 | 12/2008 | Lee et al. |
| 6,951,217 B2 | 10/2005 | Berthon-Jones | | 7,472,702 B2 | 1/2009 | Beck et al. |
| 6,971,382 B1 | 12/2005 | Corso | | 7,478,641 B2 | 1/2009 | Rousselet |
| 6,986,353 B2 | 1/2006 | Wright | | 7,481,219 B2 | 1/2009 | Lewis et al. |
| 6,994,089 B2 | 2/2006 | Wood | | 7,481,221 B2 | 1/2009 | Kullik et al. |
| 6,997,177 B2 | 2/2006 | Wood | | 7,487,774 B2 | 2/2009 | Acker |
| 6,997,881 B2 | 2/2006 | Greene et al. | | 7,487,778 B2 | 2/2009 | Freitag |
| 7,000,612 B2 | 2/2006 | Jafari et al. | | 7,490,605 B2 | 2/2009 | Frye et al. |
| 7,004,170 B1 | 2/2006 | Gillstrom | | D588,258 S | 3/2009 | Judson et al. |
| 7,007,692 B2 | 3/2006 | Aylsworth et al. | | D589,139 S | 3/2009 | Guney et al. |
| 7,011,091 B2 | 3/2006 | Hill et al. | | 7,500,482 B2 | 3/2009 | Biederman |
| 7,013,892 B2 | 3/2006 | Estes et al. | | 7,509,957 B2 | 3/2009 | Duquette et al. |
| 7,013,898 B2 | 3/2006 | Rashad et al. | | D591,419 S | 4/2009 | Chandran et al. |
| 7,017,574 B2 | 3/2006 | Biondi et al. | | 7,533,670 B1 | 5/2009 | Freitag et al. |
| 7,017,575 B2 | 3/2006 | Yagi et al. | | 7,556,038 B2 | 7/2009 | Kirby et al. |
| 7,024,945 B2 | 4/2006 | Wallace | | 7,559,327 B2 | 7/2009 | Hernandez |
| 7,036,504 B2 | 5/2006 | Wallace et al. | | 7,562,657 B2 | 7/2009 | Blanch et al. |
| 7,044,129 B1 | 5/2006 | Truschel et al. | | 7,562,659 B2 | 7/2009 | Matarasso |
| 7,047,969 B2 | 5/2006 | Noble | | 7,578,294 B2 | 8/2009 | Pierro et al. |
| 7,047,974 B2 | 5/2006 | Strickland et al. | | 7,588,033 B2 | 9/2009 | Wondka |
| 7,051,735 B2 | 5/2006 | Mechlenburg et al. | | 7,591,265 B2 | 9/2009 | Lee et al. |
| 7,055,522 B2 | 6/2006 | Berthon-Jones | | 7,631,642 B2 | 12/2009 | Freitag et al. |
| 7,059,328 B2 | 6/2006 | Wood | | 7,640,934 B2 | 1/2010 | Zollinger et al. |
| 7,066,173 B2 | 6/2006 | Banner et al. | | 7,658,189 B2 | 2/2010 | Davidson et al. |
| 7,066,178 B2 | 6/2006 | Gunaratnam et al. | | D614,288 S | 4/2010 | Judson et al. |
| 7,077,132 B2 | 7/2006 | Berthon-Jones | | 7,721,733 B2 | 5/2010 | Hughes et al. |
| 7,077,133 B2 | 7/2006 | Yagi et al. | | 7,721,736 B2 | 5/2010 | Urias et al. |
| 7,080,645 B2 | 7/2006 | Genger et al. | | 7,740,013 B2 | 6/2010 | Ishizaki et al. |
| 7,080,646 B2 | 7/2006 | Wiesmann et al. | | 7,743,770 B2 | 6/2010 | Curti et al. |
| 7,100,607 B2 | 9/2006 | Zdrojkowski et al. | | 7,762,253 B2 | 7/2010 | Acker et al. |
| 7,100,609 B2 | 9/2006 | Berthon-Jones et al. | | 7,766,009 B2 | 8/2010 | Frye et al. |
| 7,117,438 B2 | 10/2006 | Wallace et al. | | 7,787,946 B2 | 8/2010 | Stahmann et al. |

| | | | | | | |
|---|---|---|---|---|---|---|
| 7,814,906 B2 | 10/2010 | Moretti | | 2002/0157673 A1 | 10/2002 | Kessler et al. |
| 7,819,120 B2 | 10/2010 | Taylor et al. | | 2002/0159323 A1 | 10/2002 | Makabe et al. |
| D626,646 S | 11/2010 | Lubke et al. | | 2002/0179090 A1 | 12/2002 | Boussignac |
| D627,059 S | 11/2010 | Wood et al. | | 2003/0000522 A1 | 1/2003 | Lynn et al. |
| 7,832,400 B2 | 11/2010 | Curti et al. | | 2003/0047185 A1 | 3/2003 | Olsen et al. |
| 7,837,761 B2 | 11/2010 | Bliss et al. | | 2003/0069489 A1 | 4/2003 | Abreu |
| 7,841,343 B2 | 11/2010 | Deane et al. | | 2003/0079749 A1 | 5/2003 | Strickland et al. |
| 7,845,350 B1 | 12/2010 | Kayyali et al. | | 2003/0094178 A1 | 5/2003 | McAuley et al. |
| 7,849,854 B2 | 12/2010 | DeVries et al. | | 2003/0111081 A1 | 6/2003 | Gupta |
| 7,856,982 B2 | 12/2010 | Matula, Jr. et al. | | 2003/0116163 A1 | 6/2003 | Wood |
| 7,866,318 B2 | 1/2011 | Bassin | | 2003/0121519 A1 | 7/2003 | Estes et al. |
| 7,874,290 B2 | 1/2011 | Chalvignac | | 2003/0145852 A1 | 8/2003 | Schmidt et al. |
| 7,874,291 B2 | 1/2011 | Ging et al. | | 2003/0145853 A1 | 8/2003 | Muellner |
| 7,874,293 B2 | 1/2011 | Gunaratnam et al. | | 2003/0145856 A1 | 8/2003 | Zdrojkowski et al. |
| 7,878,980 B2 | 2/2011 | Ricciardelli | | 2003/0150455 A1 | 8/2003 | Bliss et al. |
| 7,882,834 B2 | 2/2011 | Gradon et al. | | 2003/0159696 A1 | 8/2003 | Boussignac et al. |
| 7,886,740 B2 | 2/2011 | Thomas et al. | | 2003/0159697 A1 | 8/2003 | Wallace |
| 7,891,353 B2 | 2/2011 | Chalvignac | | 2003/0168067 A1 | 9/2003 | Dougill et al. |
| 7,891,357 B2 | 2/2011 | Carron et al. | | 2003/0213488 A1 | 11/2003 | Remmers et al. |
| 7,896,958 B2 | 3/2011 | Sermet et al. | | 2003/0221687 A1 | 12/2003 | Kaigler |
| 7,900,627 B2 | 3/2011 | Aylsworth et al. | | 2003/0230308 A1 | 12/2003 | Linden |
| 7,900,628 B2 | 3/2011 | Matula, Jr. et al. | | 2004/0020493 A1 | 2/2004 | Wood |
| 7,900,635 B2 | 3/2011 | Gunaratnam et al. | | 2004/0025881 A1 | 2/2004 | Gunaratnam et al. |
| 7,901,361 B2 | 3/2011 | Rapoport et al. | | 2004/0035431 A1 | 2/2004 | Wright |
| 7,905,231 B2 | 3/2011 | Chalvignac | | 2004/0040560 A1 | 3/2004 | Euliano et al. |
| 7,913,691 B2 | 3/2011 | Farrugia | | 2004/0050387 A1 | 3/2004 | Younes |
| 7,914,459 B2 | 3/2011 | Green et al. | | 2004/0074494 A1 | 4/2004 | Frater |
| 7,918,226 B2 | 4/2011 | Acker et al. | | 2004/0159323 A1 | 8/2004 | Schmidt et al. |
| 7,926,486 B2 | 4/2011 | Childers | | 2004/0206352 A1 | 10/2004 | Conroy |
| 7,926,487 B2 | 4/2011 | Drew et al. | | 2004/0221848 A1 | 11/2004 | Hill |
| 7,931,023 B2 | 4/2011 | Berthon-Jones et al. | | 2004/0221854 A1 | 11/2004 | Hete et al. |
| 7,934,499 B2 | 5/2011 | Berthon-Jones | | 2004/0226566 A1 | 11/2004 | Gunaratnam et al. |
| 7,938,114 B2 | 5/2011 | Matthews et al. | | 2004/0231674 A1 | 11/2004 | Tanaka |
| 7,942,150 B2 | 5/2011 | Guney et al. | | 2004/0237963 A1 | 12/2004 | Berthon-Jones |
| 7,942,380 B2 | 5/2011 | Bertinetti et al. | | 2004/0254501 A1 | 12/2004 | Mault |
| 7,958,892 B2 | 6/2011 | Kwok et al. | | 2004/0255943 A1 | 12/2004 | Morris et al. |
| 7,975,694 B2 | 7/2011 | Ho | | 2005/0005936 A1 | 1/2005 | Wondka |
| 7,980,245 B2 | 7/2011 | Rice et al. | | 2005/0005938 A1 | 1/2005 | Berthon-Jones et al. |
| 7,987,847 B2 | 8/2011 | Wickham et al. | | 2005/0010125 A1 | 1/2005 | Joy et al. |
| 7,987,850 B2 | 8/2011 | Zollinger et al. | | 2005/0011524 A1 | 1/2005 | Thomlinson et al. |
| 7,987,851 B2 | 8/2011 | Blom et al. | | 2005/0016534 A1 | 1/2005 | Ost |
| 7,992,557 B2 | 8/2011 | Nadjafizadeh et al. | | 2005/0033247 A1 | 2/2005 | Thompson |
| 7,997,270 B2 | 8/2011 | Meier | | 2005/0034721 A1 | 2/2005 | Freitag |
| 7,997,271 B2 | 8/2011 | Hickle et al. | | 2005/0034724 A1 | 2/2005 | O'Dea |
| 7,997,272 B2 | 8/2011 | Isaza | | 2005/0061322 A1 | 3/2005 | Freitag |
| 8,001,967 B2 | 8/2011 | Wallace et al. | | 2005/0061326 A1 | 3/2005 | Payne |
| D645,557 S | 9/2011 | Scheiner et al. | | 2005/0072430 A1 | 4/2005 | Djupesland |
| 8,011,365 B2 | 9/2011 | Douglas et al. | | 2005/0081849 A1 | 4/2005 | Warren |
| 8,011,366 B2 | 9/2011 | Knepper | | 2005/0087190 A1 | 4/2005 | Jafari et al. |
| 8,015,971 B2 | 9/2011 | Kwok | | 2005/0098179 A1 | 5/2005 | Burton et al. |
| 8,015,974 B2 | 9/2011 | Christopher et al. | | 2005/0103343 A1 | 5/2005 | Gosweiler |
| 8,020,558 B2 | 9/2011 | Christopher et al. | | 2005/0121033 A1 | 6/2005 | Starr et al. |
| 8,025,052 B2 | 9/2011 | Matthews et al. | | 2005/0121037 A1 | 6/2005 | Wood |
| RE42,843 E | 10/2011 | Strickland et al. | | 2005/0121038 A1 | 6/2005 | Christopher |
| 8,042,535 B2 | 10/2011 | Kenyon et al. | | 2005/0150498 A1 | 7/2005 | McDonald |
| 8,042,537 B2 | 10/2011 | Mechlenburg et al. | | 2005/0161049 A1 | 7/2005 | Wright |
| 8,042,539 B2 | 10/2011 | Chandran et al. | | 2005/0166924 A1 | 8/2005 | Thomas et al. |
| 8,042,546 B2 | 10/2011 | Gunaratnam et al. | | 2005/0199242 A1 | 9/2005 | Matula et al. |
| 8,061,354 B2 | 11/2011 | Schneider et al. | | 2005/0205096 A1 | 9/2005 | Matula et al. |
| 8,066,004 B2 | 11/2011 | Morris et al. | | 2005/0247308 A1 | 11/2005 | Frye et al. |
| 2001/0035185 A1 | 11/2001 | Christopher | | 2005/0257793 A1 | 11/2005 | Tatsumoto |
| 2001/0035186 A1 | 11/2001 | Hill | | 2005/0274381 A1 | 12/2005 | Deane et al. |
| 2001/0042548 A1 | 11/2001 | Boussignac | | 2006/0005834 A1 | 1/2006 | Aylsworth et al. |
| 2002/0014241 A1 | 2/2002 | Gradon et al. | | 2006/0005842 A1 | 1/2006 | Rashad et al. |
| 2002/0017300 A1 | 2/2002 | Hickle et al. | | 2006/0011199 A1 | 1/2006 | Rashad et al. |
| 2002/0020930 A1 | 2/2002 | Austin et al. | | 2006/0027234 A1 | 2/2006 | Gradon et al. |
| 2002/0026941 A1 | 3/2002 | Biondi et al. | | 2006/0048781 A1 | 3/2006 | Nawata |
| 2002/0043264 A1 | 4/2002 | Wickham | | 2006/0054169 A1 | 3/2006 | Han et al. |
| 2002/0046751 A1 | 4/2002 | MacRae et al. | | 2006/0070625 A1 | 4/2006 | Ayappa et al. |
| 2002/0046755 A1 | 4/2002 | De Voss | | 2006/0079799 A1 | 4/2006 | Green et al. |
| 2002/0046756 A1 | 4/2002 | Laizzo et al. | | 2006/0096596 A1 | 5/2006 | Occhialini et al. |
| 2002/0053346 A1 | 5/2002 | Curti et al. | | 2006/0107958 A1 | 5/2006 | Sleeper |
| 2002/0055685 A1 | 5/2002 | Levitsky et al. | | 2006/0112959 A1 | 6/2006 | Mechlenburg et al. |
| 2002/0059935 A1 | 5/2002 | Wood | | 2006/0124131 A1 | 6/2006 | Chandran et al. |
| 2002/0066452 A1 | 6/2002 | Kessler et al. | | 2006/0124134 A1 | 6/2006 | Wood |
| 2002/0078957 A1 | 6/2002 | Remmers et al. | | 2006/0137690 A1 | 6/2006 | Gunaratnam et al. |
| 2002/0092527 A1 | 7/2002 | Wood | | 2006/0144396 A1 | 7/2006 | DeVries et al. |
| 2002/0112730 A1 | 8/2002 | Dutkiewicz | | 2006/0149144 A1 | 7/2006 | Lynn et al. |
| 2002/0153010 A1 | 10/2002 | Rozenberg et al. | | 2006/0150972 A1 | 7/2006 | Mizuta et al. |

| Pub. No. | Date | Name |
|---|---|---|
| 2006/0150973 A1 | 7/2006 | Chalvignac |
| 2006/0150982 A1 | 7/2006 | Wood |
| 2006/0174877 A1 | 8/2006 | Jagger et al. |
| 2006/0180149 A1 | 8/2006 | Matarasso |
| 2006/0185669 A1 | 8/2006 | Bassovitch |
| 2006/0201504 A1 | 9/2006 | Singhal et al. |
| 2006/0213518 A1 | 9/2006 | DeVries et al. |
| 2006/0213519 A1 | 9/2006 | Schmidt et al. |
| 2006/0225737 A1 | 10/2006 | Iobbi |
| 2006/0237013 A1 | 10/2006 | Kwok |
| 2006/0243278 A1 | 11/2006 | Hamilton et al. |
| 2006/0249155 A1 | 11/2006 | Gambone |
| 2006/0266361 A1 | 11/2006 | Hernandez |
| 2007/0000490 A1 | 1/2007 | DeVries et al. |
| 2007/0000495 A1 | 1/2007 | Matula et al. |
| 2007/0017515 A1 | 1/2007 | Wallace et al. |
| 2007/0056590 A1 | 3/2007 | Wolfson |
| 2007/0062529 A1 | 3/2007 | Choncholas et al. |
| 2007/0068528 A1 | 3/2007 | Bohm et al. |
| 2007/0074724 A1 | 4/2007 | Duquette et al. |
| 2007/0089743 A1 | 4/2007 | Hoffman |
| 2007/0089745 A1 | 4/2007 | Gabriel et al. |
| 2007/0095347 A1 | 5/2007 | Lampotang et al. |
| 2007/0107728 A1 | 5/2007 | Ricciardelli et al. |
| 2007/0107732 A1 | 5/2007 | Dennis et al. |
| 2007/0107737 A1 | 5/2007 | Landis et al. |
| 2007/0113850 A1 | 5/2007 | Acker et al. |
| 2007/0113856 A1 | 5/2007 | Acker et al. |
| 2007/0125379 A1 | 6/2007 | Pierro et al. |
| 2007/0137653 A1 | 6/2007 | Wood |
| 2007/0163600 A1 | 7/2007 | Hoffman |
| 2007/0173705 A1 | 7/2007 | Teller et al. |
| 2007/0181125 A1 | 8/2007 | Mulier |
| 2007/0193705 A1 | 8/2007 | Hsu |
| 2007/0199568 A1 | 8/2007 | Diekens et al. |
| 2007/0209662 A1 | 9/2007 | Bowen et al. |
| 2007/0215156 A1 | 9/2007 | Kwok |
| 2007/0232950 A1 | 10/2007 | West |
| 2007/0240716 A1 | 10/2007 | Marx |
| 2007/0251528 A1 | 11/2007 | Seitz et al. |
| 2007/0272249 A1 | 11/2007 | Chandran et al. |
| 2008/0000475 A1 | 1/2008 | Hill |
| 2008/0006271 A1 | 1/2008 | Aylsworth et al. |
| 2008/0011298 A1 | 1/2008 | Mazar et al. |
| 2008/0011301 A1 | 1/2008 | Qian |
| 2008/0041371 A1 | 2/2008 | Freitag |
| 2008/0041386 A1 | 2/2008 | Dodier et al. |
| 2008/0045815 A1 | 2/2008 | Derchak et al. |
| 2008/0047559 A1 | 2/2008 | Fiori |
| 2008/0051674 A1 | 2/2008 | Davenport et al. |
| 2008/0053438 A1 | 3/2008 | DeVries et al. |
| 2008/0053447 A1 | 3/2008 | Ratajczak et al. |
| 2008/0060646 A1 | 3/2008 | Isaza |
| 2008/0060657 A1 | 3/2008 | McAuley et al. |
| 2008/0066753 A1 | 3/2008 | Martin et al. |
| 2008/0072902 A1 | 3/2008 | Setzer et al. |
| 2008/0078392 A1 | 4/2008 | Pelletier et al. |
| 2008/0078407 A1 | 4/2008 | Sherman |
| 2008/0092904 A1 | 4/2008 | Gunarathnam et al. |
| 2008/0092905 A1 | 4/2008 | Gunarathnam et al. |
| 2008/0092906 A1 | 4/2008 | Gunarathnam et al. |
| 2008/0099024 A1 | 5/2008 | Gunarathnam et al. |
| 2008/0099027 A1 | 5/2008 | Gunaratnam et al. |
| 2008/0105264 A1 | 5/2008 | Gunarathnam et al. |
| 2008/0110462 A1 | 5/2008 | Chekal et al. |
| 2008/0121230 A1 | 5/2008 | Cortez et al. |
| 2008/0142019 A1 | 6/2008 | Lewis et al. |
| 2008/0161653 A1 | 7/2008 | Lin et al. |
| 2008/0173304 A1 | 7/2008 | Zaiser et al. |
| 2008/0178880 A1 | 7/2008 | Christopher et al. |
| 2008/0178881 A1 | 7/2008 | Whitcher et al. |
| 2008/0178882 A1 | 7/2008 | Christopher et al. |
| 2008/0185002 A1 | 8/2008 | Berthon-Jones et al. |
| 2008/0185007 A1 | 8/2008 | Sleeper et al. |
| 2008/0190429 A1 | 8/2008 | Tatarek |
| 2008/0190436 A1 | 8/2008 | Jaffe et al. |
| 2008/0196715 A1 | 8/2008 | Yamamori |
| 2008/0196723 A1 | 8/2008 | Tilley |
| 2008/0196728 A1 | 8/2008 | Ho |
| 2008/0202528 A1 | 8/2008 | Carter et al. |
| 2008/0216834 A1 | 9/2008 | Easley et al. |
| 2008/0216838 A1 | 9/2008 | Wondka |
| 2008/0216841 A1 | 9/2008 | Grimes et al. |
| 2008/0223369 A1 | 9/2008 | Warren |
| 2008/0245369 A1 | 10/2008 | Matula et al. |
| 2008/0251079 A1 | 10/2008 | Richey |
| 2008/0264417 A1 | 10/2008 | Manigel et al. |
| 2008/0283060 A1 | 11/2008 | Bassin |
| 2008/0295846 A1 | 12/2008 | Han et al. |
| 2008/0302364 A1 | 12/2008 | Garde et al. |
| 2008/0308104 A1 | 12/2008 | Blomberg et al. |
| 2009/0007911 A1 | 1/2009 | Cleary et al. |
| 2009/0020121 A1 | 1/2009 | Bassin |
| 2009/0044808 A1 | 2/2009 | Guney et al. |
| 2009/0056708 A1 | 3/2009 | Stenzler et al. |
| 2009/0078255 A1 | 3/2009 | Bowman et al. |
| 2009/0078258 A1 | 3/2009 | Bowman et al. |
| 2009/0095298 A1 | 4/2009 | Gunaratnam et al. |
| 2009/0095300 A1 | 4/2009 | McMorrow |
| 2009/0095303 A1 | 4/2009 | Sher et al. |
| 2009/0099471 A1 | 4/2009 | Broadley et al. |
| 2009/0101147 A1 | 4/2009 | Landis et al. |
| 2009/0101154 A1 | 4/2009 | Mutti et al. |
| 2009/0107502 A1 | 4/2009 | Younes |
| 2009/0118632 A1 | 5/2009 | Goepp |
| 2009/0120437 A1 | 5/2009 | Oates et al. |
| 2009/0126739 A1 | 5/2009 | Ng et al. |
| 2009/0133699 A1 | 5/2009 | Nalagatla et al. |
| 2009/0139527 A1 | 6/2009 | Ng et al. |
| 2009/0145435 A1 | 6/2009 | White et al. |
| 2009/0151719 A1 | 6/2009 | Wondka et al. |
| 2009/0151724 A1 | 6/2009 | Wondka et al. |
| 2009/0151726 A1 | 6/2009 | Freitag |
| 2009/0151729 A1 | 6/2009 | Judson et al. |
| 2009/0156953 A1 | 6/2009 | Wondka et al. |
| 2009/0165799 A1 | 7/2009 | Duquette et al. |
| 2009/0173347 A1 | 7/2009 | Berthon-Jones |
| 2009/0173349 A1 | 7/2009 | Hernandez et al. |
| 2009/0183739 A1 | 7/2009 | Wondka |
| 2009/0199855 A1 | 8/2009 | Davenport |
| 2009/0205662 A1 | 8/2009 | Kwok et al. |
| 2009/0241947 A1 | 10/2009 | Bedini et al. |
| 2009/0241951 A1 | 10/2009 | Jafari et al. |
| 2009/0250066 A1 | 10/2009 | Daly |
| 2009/0255533 A1 | 10/2009 | Freitag et al. |
| 2009/0260625 A1 | 10/2009 | Wondka |
| 2009/0277452 A1 | 11/2009 | Lubke et al. |
| 2009/0293877 A1 | 12/2009 | Blanch et al. |
| 2009/0301495 A1 | 12/2009 | Pierro et al. |
| 2009/0308395 A1 | 12/2009 | Lee et al. |
| 2009/0320851 A1 | 12/2009 | Selvarajan et al. |
| 2010/0043786 A1 | 2/2010 | Freitag et al. |
| 2010/0071693 A1 | 3/2010 | Allum et al. |
| 2010/0071697 A1 | 3/2010 | Jafari et al. |
| 2010/0083968 A1 | 4/2010 | Wondka et al. |
| 2010/0108073 A1 | 5/2010 | Zollinger et al. |
| 2010/0132716 A1 | 6/2010 | Selvarajan et al. |
| 2010/0132717 A1 | 6/2010 | Davidson et al. |
| 2010/0163043 A1 | 7/2010 | Hart et al. |
| 2010/0170512 A1 | 7/2010 | Kuypers et al. |
| 2010/0170513 A1 | 7/2010 | Bowditch et al. |
| 2010/0192957 A1 | 8/2010 | Hobson et al. |
| 2010/0218766 A1 | 9/2010 | Milne |
| 2010/0224196 A1 | 9/2010 | Jablons |
| 2010/0252037 A1 | 10/2010 | Wondka et al. |
| 2010/0252039 A1 | 10/2010 | Cipollone et al. |
| 2010/0252040 A1 | 10/2010 | Kapust et al. |
| 2010/0252041 A1 | 10/2010 | Kapust et al. |
| 2010/0252042 A1 | 10/2010 | Kapust et al. |
| 2010/0252043 A1 | 10/2010 | Freitag |
| 2010/0252044 A1 | 10/2010 | Duquette et al. |
| 2010/0269834 A1 | 10/2010 | Freitag et al. |
| 2010/0275920 A1 | 11/2010 | Tham et al. |
| 2010/0275921 A1 | 11/2010 | Schindhelm et al. |
| 2010/0282251 A1 | 11/2010 | Calluaud et al. |
| 2010/0282810 A1 | 11/2010 | Hawes |
| 2010/0288279 A1 | 11/2010 | Seiver et al. |
| 2010/0288289 A1 | 11/2010 | Nasir |

| Publication No. | Date | Inventor |
|---|---|---|
| 2010/0300445 A1 | 12/2010 | Chatburn et al. |
| 2010/0300446 A1 | 12/2010 | Nicolazzi et al. |
| 2010/0307487 A1 | 12/2010 | Dunsmore et al. |
| 2010/0307495 A1 | 12/2010 | Kepler et al. |
| 2010/0307499 A1 | 12/2010 | Eger et al. |
| 2010/0307500 A1 | 12/2010 | Armitstead |
| 2010/0307502 A1 | 12/2010 | Rummery et al. |
| 2010/0313891 A1 | 12/2010 | Veliss et al. |
| 2010/0313898 A1 | 12/2010 | Richard et al. |
| 2010/0319703 A1 | 12/2010 | Hayman et al. |
| 2010/0326441 A1 | 12/2010 | Zucker et al. |
| 2010/0326446 A1 | 12/2010 | Behlmaier |
| 2011/0000489 A1 | 1/2011 | Laksov et al. |
| 2011/0009763 A1 | 1/2011 | Levitsky et al. |
| 2011/0011402 A1 | 1/2011 | Berthon-Jones |
| 2011/0023878 A1 | 2/2011 | Thiessen |
| 2011/0023881 A1 | 2/2011 | Thiessen |
| 2011/0034819 A1 | 2/2011 | Desforges et al. |
| 2011/0036352 A1 | 2/2011 | Estes et al. |
| 2011/0041850 A1 | 2/2011 | Vandine et al. |
| 2011/0041855 A1 | 2/2011 | Gunaratnam et al. |
| 2011/0061647 A1 | 3/2011 | Stahmann et al. |
| 2011/0067704 A1 | 3/2011 | Kooij et al. |
| 2011/0067709 A1 | 3/2011 | Doshi et al. |
| 2011/0071444 A1 | 3/2011 | Kassatly et al. |
| 2011/0073107 A1 | 3/2011 | Rodman et al. |
| 2011/0073116 A1 | 3/2011 | Genger et al. |
| 2011/0087123 A9 | 4/2011 | Choncholas et al. |
| 2011/0088690 A1 | 4/2011 | Djupesland et al. |
| 2011/0094518 A1 | 4/2011 | Cipollone et al. |
| 2011/0100365 A1 | 5/2011 | Wedler et al. |
| 2011/0114098 A1 | 5/2011 | McAuley et al. |
| 2011/0125052 A1 | 5/2011 | Davenport et al. |
| 2011/0126841 A1 | 6/2011 | Matula, Jr. et al. |
| 2011/0132363 A1 | 6/2011 | Chalvignac |
| 2011/0139153 A1 | 6/2011 | Chalvignac |
| 2011/0146687 A1 | 6/2011 | Fukushima |
| 2011/0155140 A1 | 6/2011 | Ho et al. |
| 2011/0162650 A1 | 7/2011 | Miller et al. |
| 2011/0162655 A1 | 7/2011 | Gunaratnam et al. |
| 2011/0178419 A1 | 7/2011 | Wood et al. |
| 2011/0180068 A1 | 7/2011 | Kenyon et al. |
| 2011/0197885 A1 | 8/2011 | Wondka et al. |
| 2011/0209705 A1 | 9/2011 | Freitag |
| 2011/0214676 A1 | 9/2011 | Allum et al. |
| 2011/0220105 A1 | 9/2011 | Meier |
| 2011/0232642 A1 | 9/2011 | Bliss et al. |
| 2011/0247625 A1 | 10/2011 | Boussignac |
| 2011/0253147 A1 | 10/2011 | Gusky et al. |
| 2011/0259327 A1 | 10/2011 | Wondka et al. |
| 2011/0265796 A1 | 11/2011 | Amarasinghe et al. |
| 2011/0277765 A1 | 11/2011 | Christopher et al. |
| 2011/0284003 A1 | 11/2011 | Douglas et al. |

FOREIGN PATENT DOCUMENTS

| | | |
|---|---|---|
| DE | 19626924 | 1/1998 |
| DE | 19841070 | 5/2000 |
| DE | 19849571 | 5/2000 |
| DE | 10337138.9 | 3/2005 |
| DE | 10 2006 023 637.8 | 11/2007 |
| EP | 0125424 | 11/1984 |
| EP | 04762494.5 | 11/1984 |
| EP | 0692273 | 1/1996 |
| EP | 0778035 | 6/1997 |
| EP | 1359961 | 11/2003 |
| GB | 2174609 | 11/1986 |
| GB | 2201098 | 8/1988 |
| GB | 1055148 | 6/1989 |
| GB | 2338420 | 12/1999 |
| IN | 317/KOLNP/06 | 3/2008 |
| JP | S63-57060 | 3/1998 |
| JP | 2002-204830 | 7/2002 |
| JP | 2006/522883 | 10/2006 |
| JP | 2006/522883 | 3/2009 |
| WO | WO-92/11054 | 7/1992 |
| WO | WO-98/01176 | 1/1998 |
| WO | WO-99/04841 | 2/1999 |
| WO | WO-00/64521 | 11/2000 |
| WO | WO-01-76655 | 10/2001 |
| WO | WO-02/062413 | 8/2002 |
| WO | WO-2004/009169 | 1/2004 |
| WO | WO-2005-014091 | 2/2005 |
| WO | WO-2005014091 | 2/2005 |
| WO | WO-2005/018524 | 3/2005 |
| WO | PCT-US06036600 | 8/2006 |
| WO | WO-2006/138580 | 12/2006 |
| WO | PCT-US07-017400 | 3/2007 |
| WO | WO-2007-035804 | 3/2007 |
| WO | WO-2007035804 | 3/2007 |
| WO | WO-2007/139531 | 12/2007 |
| WO | WO-2007142812 | 12/2007 |
| WO | WO-2008/014543 | 2/2008 |
| WO | WO-2008/019102 | 2/2008 |
| WO | WO-2008/052534 | 5/2008 |
| WO | WO-2008/112474 | 9/2008 |
| WO | WO-2008/138040 | 11/2008 |
| WO | WO-2008/144589 | 11/2008 |
| WO | WO-2008/144669 | 11/2008 |
| WO | WO-2009/042973 | 4/2009 |
| WO | WO-2009/042974 | 4/2009 |
| WO | WO-2009/059353 | 5/2009 |
| WO | WO-2009/064202 | 5/2009 |
| WO | WO-2009/074160 | 6/2009 |
| WO | WO-2009/082295 | 7/2009 |
| WO | WO-2009/087607 | 7/2009 |
| WO | WO-2009/092057 | 7/2009 |
| WO | WO-2009/103288 | 8/2009 |
| WO | WO-2009/109005 | 9/2009 |
| WO | WO-2009/115944 | 9/2009 |
| WO | WO-2009/115948 | 9/2009 |
| WO | WO-2009/115949 | 9/2009 |
| WO | WO-2009/129506 | 10/2009 |
| WO | WO-2009/136101 | 11/2009 |
| WO | WO-2009/139647 | 11/2009 |
| WO | WO-2009/149353 | 12/2009 |
| WO | WO-2009/149355 | 12/2009 |
| WO | WO-2009/149357 | 12/2009 |
| WO | WO-2009/151344 | 12/2009 |
| WO | WO-2009/151791 | 12/2009 |
| WO | WO-2010/000135 | 1/2010 |
| WO | WO-2010/021556 | 2/2010 |
| WO | WO-2010/022363 | 2/2010 |
| WO | WO-2010/039989 | 4/2010 |
| WO | WO-2010/041966 | 4/2010 |
| WO | WO-2010/044034 | 4/2010 |
| WO | WO-2010/057268 | 5/2010 |
| WO | WO-2010/059049 | 5/2010 |
| WO | WO-2010/060422 | 6/2010 |
| WO | WO-2010/068356 | 6/2010 |
| WO | WO-2010/070493 | 6/2010 |
| WO | WO-2010/070497 | 6/2010 |
| WO | WO-2010/070498 | 6/2010 |
| WO | WO-2010/076711 | 7/2010 |
| WO | WO-2010/081223 | 7/2010 |
| WO | WO-2010/091157 | 8/2010 |
| WO | WO-2010/099375 | 9/2010 |
| WO | WO-2010/102094 | 9/2010 |
| WO | WO-2010/115166 | 10/2010 |
| WO | WO-2010/115168 | 10/2010 |
| WO | WO-2010/115169 | 10/2010 |
| WO | WO-2010/115170 | 10/2010 |
| WO | WO-2010/116275 | 10/2010 |
| WO | WO-2010/132853 | 11/2010 |
| WO | WO-2010/136923 | 12/2010 |
| WO | WO-2010/139014 | 12/2010 |
| WO | WO-2010/150187 | 12/2010 |
| WO | WO-2011/002608 | 1/2011 |
| WO | WO-2011/004274 | 1/2011 |
| WO | WO-2011/006184 | 1/2011 |
| WO | WO-2011/006199 | 1/2011 |
| WO | WO-2011/014931 | 2/2011 |
| WO | WO-2011/017033 | 2/2011 |
| WO | WO-2011/017738 | 2/2011 |
| WO | WO-2011/021978 | 2/2011 |
| WO | WO-2011/022779 | 3/2011 |
| WO | WO-2011/024383 | 3/2011 |
| WO | WO-2011/029073 | 3/2011 |
| WO | WO-2011/029074 | 3/2011 |

| WO | WO-2011/035373 | 3/2011 |
| --- | --- | --- |
| WO | WO-2011/038950 | 4/2011 |
| WO | WO-2011/038951 | 4/2011 |
| WO | WO-2011/044627 | 4/2011 |
| WO | WO-2011/057362 | 5/2011 |
| WO | WO 2011/059346 | 5/2011 |
| WO | WO-2011/061648 | 5/2011 |
| WO | WO-2011/062510 | 5/2011 |
| WO | WO-2011/086437 | 7/2011 |
| WO | WO-2011/086438 | 7/2011 |
| WO | WO-2011/112807 | 9/2011 |

OTHER PUBLICATIONS

U.S. Appl. No. 60/960,370 (co-pending), filed Sep. 26, 2007, Wondka et al.
U.S. Appl. No. 60/960,392 (co-pending), filed Sep. 26, 2007, Wondka et al.
International Search Report for WO 2005/014091 (Application No. PCT/DE04/1646), filed Jan. 17, 2005.
Christopher, et al., "Transtracheal Oxygen Therapy for Refractory Hypoxemia," *JAMA*, 1986, vol. 256, No. 4, pp. 494-497.
Fink, J.B., "Helium-Oxygen: An Old Therapy Creates New Interest," *J Resp Care Pract now RT for Decision Makers in Respiratory Care*, Apr./May 1999, pp. 71-76.
Haenel, et al., "Efficacy of Selective Intrabronchial Air Insufflation in Acute Lobar Colapse," *Am J Surg*, 1992, vol. 164, No. 5, pp. 501-505.
"AARC Clinical Practice Guideline: Oxygen Therapy in the Home or Extended Care Facility," *Respiratory Care*, Aug. 1992, vol. 37, No. 8, pp. 918-922.
MacIntyre, N. R., "Long-Term Oxygen Therapy: Conference Summary," *Respiratory Care*, Feb. 2000, vol. 45, No. 2, pp. 237-245.
*VHA/DOD Clinical Practice Guideline*, "Management of Chronic Obstructive Pulmonary Disease," Ver. 1.1a, Aug. 1999, Updated Nov. 1999.
Blanch, L. L., "Clinical Studies of Tracheal Gas Insufflation," *Respiratory Care*, Feb. 2001, vol. 46, No. 2, pp. 158-166.
Gregoretti, et al., "Transtracheal Open Ventilation in Acute Respiratory Failure Secondary to Severe Chronic Obstructive Pulmonary Disease Exacerbation," *Am J Respir Crit Care Med*, 2006, vol. 173, No. 8, pp. 877-881.
Christopher, et al., "Preliminary Observations of Transtracheal Augmented Ventilation for Chronic Severe Respiratory Disease," *Respiratory Care*, Jan. 2001, vol. 46, No. 1, pp. 15-25.
Chang, et al., "Reduced Inspiratory Muscle endurance Following Successful Weaning From Prolonged Mechanical Ventilation," *Chest*, 2005, vol. 128, No. 2, pp. 553-559.
Gaughan, et al., "A Comparison in a Lung Model of Low- and High-Flow Regulators for Transtracheal Jet Ventilation," *Anesthesiology*, 1992, vol. 77, No. 1, pp. 189-199.
Menon, et al., "Tracheal Perforation. A Complication Associated with Transtracheal Oxygen Therapy," *Chest*, 1993, vol. 104, No. 2, pp. 636-637.
Rothe, et al., "Near Fatal Complication of Transtracheal Oxygen Therapy with the SCOOP(R) System," *Pneumologie*, 1996, vol. 50, No. 10, pp. 700-702. (English Abstract provided).
International Search Report and Opinion for Application No. PCT/US07/17400, dated Apr. 28, 2008.
Ambrosino, "Weaning and Respiratory Muscle Dysfunction: The Egg Chicken Dilemma," Chest, 2005, vol. 128(2), pp. 481-483.
Messinger et al., "Using Tracheal Pressure to Trigger the Ventilator and Control Airway Pressure During Continuous Positive Airway Pressure Decreases Work of Breathing," Chest, 1995, vol. 108, No. 2, pp. 509-514.
Messinger et al., "Tracheal pressure triggering a demand flow CPAP system decreases work of breathing," Anesthesiology, 1994, vol. 81, A272.
Koska et al., "Evaluation of a fiberoptic system for airway pressure monitoring," J. Clin Monit, 1993, vol. 10, No. 4, pp. 247-250.
Banner et al., "Imposed work of breathing and methods of triggering demand-flow, continuous positive airway pressure system," Critical Care Medicine, 1993, vol. 21, No. 2, pp. 183-190.
Banner et al., "Site of pressure measurement during spontaneous breathing with continuous positive airway pressure: Effect on calculating imposed work of breathing," Critical Care, 1992, vol. 20, No. 4, pp. 528-533.
Sinderby et al., "Neural control of mechanical ventilation in respiratory failure", Nat Med., 1999; 5:1433-1436.
Tiep et al., "Pulsed nasal and transtracheal oxygen delivery," *Chest*, 1990, vol. 97, pp. 364-368.
Yaeger et al., "Oxygen Therapy Using Pulse and Continuous Flow With a Transtracheal Catheter and a Nasal Cannula," *Chest*, 1994, vol. 106, pp. 854-860.
Passy-Muir Inc., "Clinical Inservice Outline", Aug. 1997, revised Apr. 2004, 19 pages.
Charlotte Regional Medical Center, "Application of the Passy-Muir Tracheostomy and Ventilator", Speech-Language Pathology Department, Jan. 1995, 8 pages.
"Passy-Muir Speaking Valves," Speech Pathology Department, Nov. 13, 1998, revised May 29, 2002, 7 pages.
Prigent et al., "Comparative Effects of Two Ventilatory Modes on Speech in Tracheostomized Patients with Neuromuscular Disease," *Am J Respir Crit Care Med*, 2003, vol. 167, No. 8, pp. 114-119.
International Search Report and Written Opinion for PCT/US07/12108, issued Aug. 8, 2008.
U.S. Appl. No. 11/798,965 (co-pending), Lutz Freitag.
U.S. Appl. No. 11/523,519 (co-pending), Freitag.
U.S. Appl. No. 11/523,518 (co-pending), Freitag et al.
U.S. Appl. No. 10/870,849 (co-pending), Anthony Wondka.
U.S. Appl. No. 10/771,803 (co-pending), Freitag.
U.S. Appl. No. 10/567,746 (co-pending), Freitag.
U.S. Appl. No. 11/882,530 (co-pending), Lutz Freitag.
U.S. Appl. No. 11/523,519 (co-pending)-A1, Freitag.
U.S. Appl. No. 11/494,530 (co-pending), Ryan Werber et al.
U.S. Appl. No. 11/438,848 (co-pending), Ryan Werber et al.
U.S. Appl. No. 11/438,761 (co-pending), Ryan Werber et al.
European Search Report issued Oct. 19, 2007 in co-pending EP 04762494.
In the U.S. Patent and Trademark Office, Supplemental Notice of Allowance dated in re: U.S. Appl. No. 10/771,803, dated Dec. 2, 2008, 2 pages.
In the U.S. Patent and Trademark Office, Supplemental Notice of Allowance dated in re: U.S. Appl. No. 10/771,803, dated Nov. 7, 2008, 2 pages.
In the U.S. Patent and Trademark Office, Examiner's Interview Summary in re: U.S. Appl. No. 10/771,803, dated Oct. 31, 2008, 4 pages.
In the U.S. Patent and Trademark Office, Notice of Allowance dated in re: U.S. Appl. No. 10/771,803, dated Oct. 20, 2008, 8 pages.
In the U.S. Patent and Trademark Office, Examiner's Interview Summary in re: U.S. Appl. No. 10/771,803, dated Nov. 2, 2007, 2 pages.
In the U.S. Patent and Trademark Office, Office Action in re: U.S. Appl. No. 10/771,803, dated Jun. 14, 2007, 12 pages.
In the U.S. Patent and Trademark Office, Restriction Requirement in re: U.S. Appl. No. 12/271,484, dated Feb. 9, 2011, 5 pages.
In the U.S. Patent and Trademark Office, Restriction Requirement in re: U.S. Appl. No. 12/754,437, dated Aug. 16, 2011, 5 pages.
In the U.S. Patent and Trademark Office, Non-Final Office Action dated in re: U.S. Appl. No. 10/567,746, dated Oct. 5, 2009, 9 pages.
In the U.S. Patent and Trademark Office, Notice of Allowance and Examiner's Interview Summary in re: U.S. Appl. No. 11/523,519, dated Jan. 16, 2009, 10 pages.
In the U.S. Patent and Trademark Office, Examiner's Interview Summary in re: U.S. Appl. No. 11/523,519, dated Jan. 13, 2009, 4 pages.
In the U.S. Patent and Trademark Office, Final Office Action in re: U.S. Appl. No. 11/523,519, dated Jul. 11, 2008, 13 pages.
In the U.S. Patent and Trademark Office, Examiner's Interview Summary in re: U.S. Appl. No. 11/523,519, dated Apr. 10, 2008, 3 pages.
In the U.S. Patent and Trademark Office, Final Office Action in re: U.S. Appl. No. 11/523,519, dated Nov. 26, 2007, 14 pages.
In the U.S. Patent and Trademark Office, Office Action in re: U.S. Appl. No. 11/523,519, dated Mar. 7, 2007, 11 pages.
In the U.S. Patent and Trademark Office, Restriction Requirement in re: U.S. Appl. No. 11/523,518, dated Dec. 30, 2009, 4 pages.

In the U.S. Patent and Trademark Office, Supplemental Notice of Allowance in re: U.S. Appl. No. 11/798,965, dated Aug. 21, 2009, 4 pages.
In the U.S. Patent and Trademark Office, Notice of Allowance in re: U.S. Appl. No. 11/798,965, dated Jul. 17, 2009, 5 pages.
In the U.S. Patent and Trademark Office, Final Office Action in re: U.S. Appl. No. 11/798,965, dated Apr. 9, 2009, 6 pages.
In the U.S. Patent and Trademark Office, Office Action in re: U.S. Appl. No. 11/798,965, dated Jul. 29, 2008, 12 pages.
In the U.S. Patent and Trademark Office, Office Action in re: U.S. Appl. No. 12/578,283, dated Oct. 19, 2011, 5 pages.
In the U.S. Patent and Trademark Office, Restriction/Election Requirement in re: U.S. Appl. No. 11/882,530, dated Apr. 27, 2011, 5 pages.
In the U.S. Patent and Trademark Office, Supplemental Notice of Allowance in re: U.S. Appl. No. 10/870,849, dated Jun. 16, 2009, 2 pages.
In the U.S. Patent and Trademark Office, Notice of Allowance in re: U.S. Appl. No. 10/870,849, dated Jun. 3, 2009, 4 pages.
In the U.S. Patent and Trademark Office, Notice of Allowance in re: U.S. Appl. No. 10/870,849, dated May 14, 2009, 8 pages.
In the U.S. Patent and Trademark Office, Restriction in re: U.S. Appl. No. 10/870,849, dated Nov. 16, 2007, 5 pages.
In the U.S. Patent and Trademark Office, Examiner's Interview Summary in re: U.S. Appl. No. 10/870,849, dated Jul. 27, 2007, 2 pages.
In the U.S. Patent and Trademark Office, Office Action in re: U.S. Appl. No. 10/870,849, dated Feb. 22, 2007, 13 pages.
In the U.S. Patent and Trademark Office, Restriction/Election Requirement in re: U.S. Appl. No. 12/493,677, dated Aug. 5, 2011, 5 pages.
In the U.S. Patent and Trademark Office, Restriction/Election Requirement in re: U.S. Appl. No. 12/153,423, dated Oct. 6, 2011, 8 pages.
In the U.S. Patent and Trademark Office, Notice of Allowance in re: U.S. Appl. No. 10/922,054, dated Feb. 12, 2008, 6 pages.
In the U.S. Patent and Trademark Office, Final Office Action in re: U.S. Appl. No. 10/922,054, dated Nov. 27, 2007, 9 pages.
In the U.S. Patent and Trademark Office, Office Action in re: U.S. Appl. No. 10/922,054, dated Mar. 14, 2007, 14 pages.
In the U.S. Patent and Trademark Office, Office Action in re: U.S. Appl. No. 10/922,054, dated Sep. 7, 2006, 21 pages.
In the U.S. Patent and Trademark Office, Restriction Requirement in re: U.S. Appl. No. 10/922,054, dated May 17, 2006, 5 pages.
In the U.S. Patent and Trademark Office, Notice of Allowance and Examiner's Interview Summary in re: U.S. Appl. No. 12/076,062, dated Nov. 2, 2011, 8 pages.
In the U.S. Patent and Trademark Office, Office Action in re: U.S. Appl. No. 12/076,062, dated Jan. 13, 2011, 14 pages.
In the U.S. Patent and Trademark Office, Office Action in re: U.S. Appl. No. 12/355,753, dated Sep. 28, 2011, 32 pages.
In the U.S. Patent and Trademark Office, Ex Parte Quayle Office Action in re: U.S. Appl. No. 29/388,700, dated Oct. 7, 2011, 5 pages.
"ATS Statement: Guidelines for the Six-Minute Walk Test," *Am. J. Respir. Crit. Care Med.*, 2002: 166, pp. 111-117.
Book—Walsh, "McGraw Hill Pocket reference Machinists' and Metalworker' Pocket Reference," *New York McGraw-Hill*, 2000, pp. 3-67, submitting 3 pages.
Ambrosino, "Exercise and noninvasive ventilatory support," *Monaldi Arch Chest Dis.*, 2000: 55(3): 242-246.
Bach et al., "Intermittent Positive Pressure Ventilation via Nasal Access in The Management of Respiratory Insufficiency," *Chest*, 1987: 92(1), pp. 168-170.
Banner et al., "Extubating at a Pressure Support Ventilation Level Corresponding to Zero Imposed Work of Breathing," *Anesthesiology*, Sep. 1994: 81(3A), p. A271.
Barakat et al., "Effect of noninvasive ventilatory support during exercise of a program in pulmonary rehabilitation in patients with COPD," *Int. J. Chron. Obstruct. Pulmon. Dis.*, 2007: 2(4), pp. 585-591.
Barreiro et al., "Noninvasive ventilation," *Crit Care Clin.*, 2007; 23(2): 201-22.
Bauer et al., "ADAM Nasal CPAP Circuit Adaptation: A Case Report," *Sleep*, 1991: 14(3), pp. 272-273.

Borghi-Silva et al., "Non-invasive ventilation improves peripheral oxygen saturation and reduces fatigability of quadriceps in patients with COPD," Respirology, 2009, 14:537-546.
Bossi et al., "Continuous Positive Airway Pressure in the Spontaneously Breathing Newborn by Means of Bilateral Nasal Cannulation," *Monatsschr Kinderheilkd*, 1975: 123(4), pp. 141-146.
Boussarsar et al., "Relationship between ventilatory settings and barotrauma in the acute respiratory distress syndrome," Intensive Care Med., 2002: 28(4): 406-13.
Ciccolella et al.; "Administration of High-Flow, Vapor-phased, Humidified Nasal Cannula Air (HF-HNC) Decreases Work of Breathing (WOB) in Healthy Subjects During Exercise," *AmJRCCM*, Apr. 2001: 163(5), Part 2, pp. A622. (Abstract Only).
Clini et al., "The Italian multicentre study on noninvasive ventilation in chronic obstructive pulmonary disease patients," *Eur. Respir. J.*, 2002, 20(3): 529-538.
Costa et al., "Influence of noninvasive ventilation by BiPAP® on exercise tolerance and respiratory muscle strength in chronic obstructive pulmonary disease patients (COPD)," *Rev. Lat. Am. Enfermagem.*, 2006: 14(3), pp. 378-382.
Díaz et al., "Breathing Pattern and Gas Exchange at Peak Exercise in COPD Patients With and Without Tidal Flow Limitation at Rest," *European Respiratory Journal*, 2001: 17, pp. 1120-1127.
Enright, "The six-minute walk test," *Resp. Care*, 2003: 8, pp. 783-785.
Ferreira et al., "Trigger Performance of Mid-level ICU Mechanical Ventilators During Assisted Ventilation: A Bench Study," *Intensive Care Medicine*, 2008,34:1669-1675.
Keilty et al., "Effect of inspiratory pressure support on exercise tolerance and breathlessness in patients with severe stable chronic obstructive pulmonary disease," *Thorax*, 1994, 49(10): 990-994.
Köhnlein et al., "Noninvasive ventilation in pulmonary rehabilitation of COPD patients," *Respir. Med.*, 2009, 103: 1329-1336.
Lewis, "Breathless No More, Defeating Adult Sleep Apnea," *FDA Consumer Magazine*, Jun. 1992, pp. 33-37.
Limberg et al., "Changes in Supplemental Oxygen Prescription in Pulmonary Rehabilitation," *Resp. Care*, 2006:51(11), p. 1302.
MacIntyre et al., "Acute exacerbations and repiratory failure in chronic obstructive pulmonary disease," *Proc. Am. Thorac. Soc.*, 2008: 5(4), pp. 530-535.
Massie et al., "Clinical Outcomes Related to Interface Type in Patients With Obstructive Sleep Apnea/Hypopnea Syndrome Who Are Using Continuous Positive Airway Pressure," *Chest*, 2003: 123(4), pp. 1112-1118.
McCoy, "Oxygen Conservation Techniques and Devices," *Resp. Care*, 2000: 45(1), pp. 95-104.
McGinley, "A nasal cannula can be used to treat obstructive sleep apnea"; *Am. J. Resp. Crit. Care Med.*, 2007: 176(2), pp. 194-200.
Menadue et al., "Non-invasive ventilation during arm exercise and ground walking in patients with chronic hypercapnic respiratory failure," *Respirology*, 2009, 14(2): 251-259.
Mettey, "Use of CPAP Nasal Cannula for Aids of the Newborns in Tropical Countries," *Medecine Tropicale*, 1985: 45(1), pp. 87-90.
Nahmias et al., "Treatment of the Obstructive Sleep Apnea Syndrome Using a Nasopharyngeal Tube", *Chest*, 1988:94(6), pp. 1142-1147.
Nava et al., "Non-invasive ventilation," *Minerva Anestesiol.*, 2009: 75(1-2), pp. 31-36.
Peters et al., "Combined Physiological Effects of Bronchodilators and Hyperoxia on Exertional Dyspnea in Normoxic COPD," *Thorax*, 2006: 61, pp. 559-567.
Polkey et al., "Inspiratory pressure support reduces slowing of inspiratory muscle relations rate during exhaustive treadmill walking in sever COPD," *Am. J. Resp. Crit. Care Med.*, 1996: 154(4, 10), pp. 1146-1150.
Porta et al., "Mask proportional assist vs pressure support ventilation in patients in clinically stable condition with chronic venilatory failure," *Chest*, 2002: 122(2), pp. 479-488.
Puente-Maestu et al., "Dyspnea, Ventilatory Pattern, and Changes in Dynamic Hyperinflation Related to the Intensity of Constant Work Rate Exercise in COPD," *Chest*, 2005: 128(2), pp. 651-656.
Ram et al., "Non-invasive positive pressure ventilation for treatment of respiratory failure due to exacerbations of chroic obstructive pulmonary disease," *Cochrane Database Syst Rev.*, 2004(3):1-72.

Rothfleisch et al., "Facilitation of fiberoptic nasotracheal intubation in a morbidly obese patient by simultaneous use of nasal CPAP," *Chest*, 1994, 106(1): 287-288.

Sanders et al., "CPAP Via Nasal Mask: A Treatment for Occlusive Sleep Apnea," *Chest*, 1983: 83(1), pp. 144-145.

Somfay et al., "Dose-Response Effect of Oxygen on Hyperinflation and Exercise Endurance in Nonhypoxaemic COPD Patients," *Eur. Resp. J.*, 2001: 18, pp. 77-84.

Sullivan et al., "Reversal of Obstructive Sleep Apnoea by Continuous Positive Airway Pressure Applied Through the Nares," *The Lancet*, 1981: 1(8225), pp. 862-865.

Sullivan, "Home treatment of obstructive sleep apnoea with continuous positive airway pressure applied through a nose-mask," *Bull Eur Physiopathol Respir.*, 1984: 20(1), pp. 49-54.

Tsuboi et al., "Ventilatory Support During Exercise in Patients With Pulmonary Tuberculosis Sequelae," *Chest*, 1997: 112(4), pp. 1000-1007.

Wijkstra et al., "Nocturnal non-invasive positive pressure ventilation for stable chronic obstructive pulmonary disease," *Cochrane Database Syst. Rev.*, 2002, 3: 1-22.

International Search Report and Written Opinion for PCT/US04/26800 issued Jun. 22, 2006.

International Search Report and Written Opinion for PCT/US08/64015, dated Sep. 26, 2008.

International Search Report and Written Opinion for PCT/US08/64164, dated Sep. 29, 2008.

International Search Report and Written Opinion for PCT/US08/78031, dated Nov. 24, 2008.

International Search Report and Written Opinion for PCT/US08/78033, dated Dec. 3, 2008.

International Search Report and Written Opinion for PCT/US09/054673, dated Oct. 8, 2009.

International Search Report and Written Opinion for PCT/US09/41027, dated Dec. 14, 2009.

International Search Report and Written Opinion for PCT/US09/59272, dated Dec. 2, 2009.

International Search Report and Written Opinion for PCT/US2006/036600, dated Apr. 3, 2007.

International Search Report and Written Opinion for PCT/US2009/031355 issued Mar. 11, 2009.

International Search Report and Written Opinion for PCT/US2009/041034, dated Jun. 10, 2009.

International Search Report and Written Opinion for PCT/US2010/029871, dated Jul. 12, 2010.

International Search Report and Written Opinion for PCT/US2010/029873, dated Jun. 28, 2010.

International Search Report and Written Opinion for PCT/US2010/029874, dated Jul. 12, 2010.

International Search Report and Written Opinion for PCT/US2010/029875, dated Jul. 12, 2010.

International Search Report and Written Opinion for PCT/US2010/047920, dated Nov. 1, 2010.

International Search Report and Written Opinion for PCT/US2010/047921, dated Jan. 27, 2011.

International Search Report for PCT/DE2004/001646, dated Jan. 17, 2005.

U.S. Appl. No. 60/924,514 (co-pending), May 18, 2007, Wondka et al.

U.S. Appl. No. 60/960,370 (co-pending), Sep. 26, 2007, Wondka et al.

U.S. Appl. No. 60/960,392 (co-pending), Sep. 26, 2007, Wondka et al.

* cited by examiner

FIG. 10a
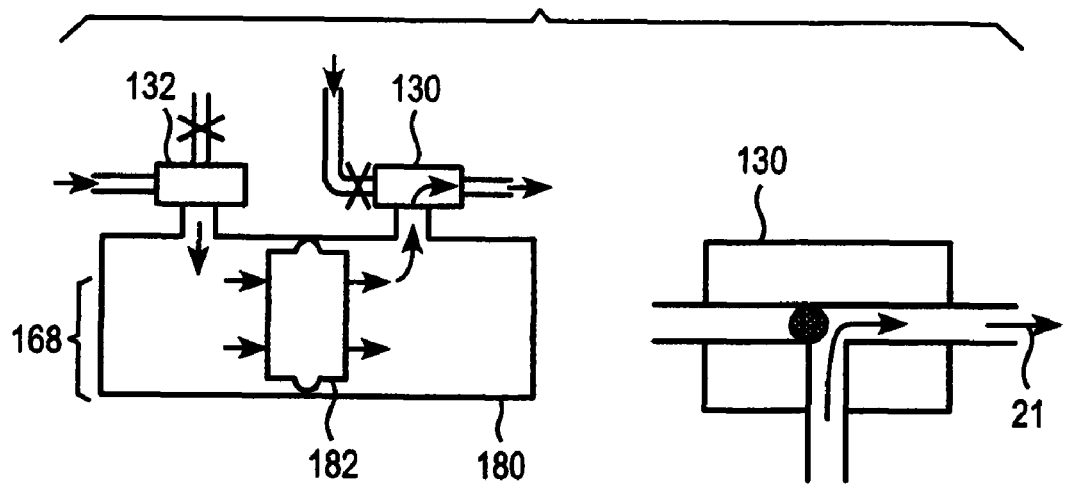
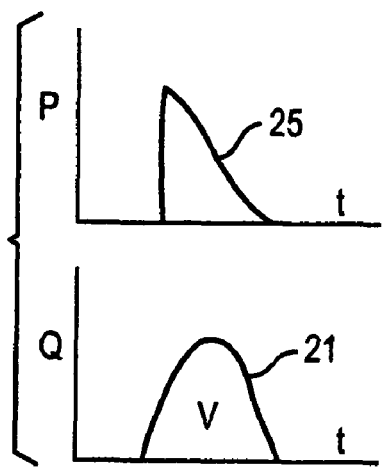
FIG. 10b
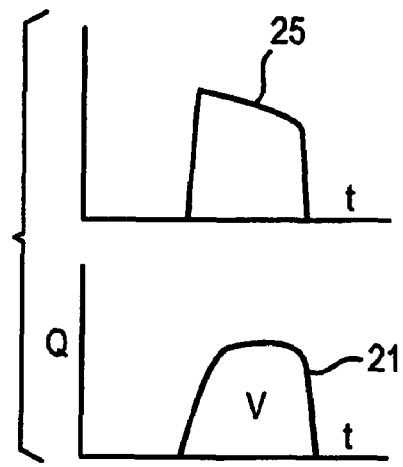
FIG. 10c

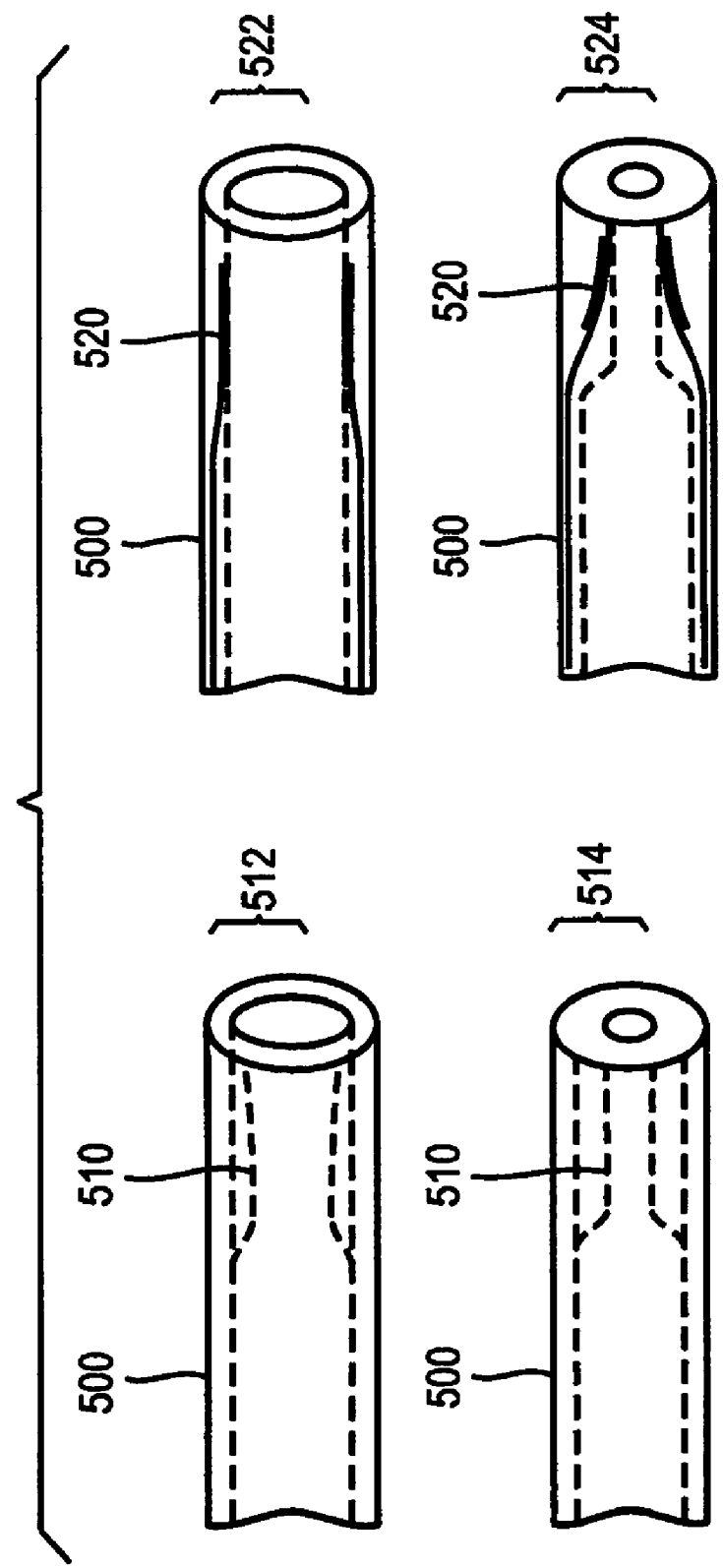

FIG. 14a
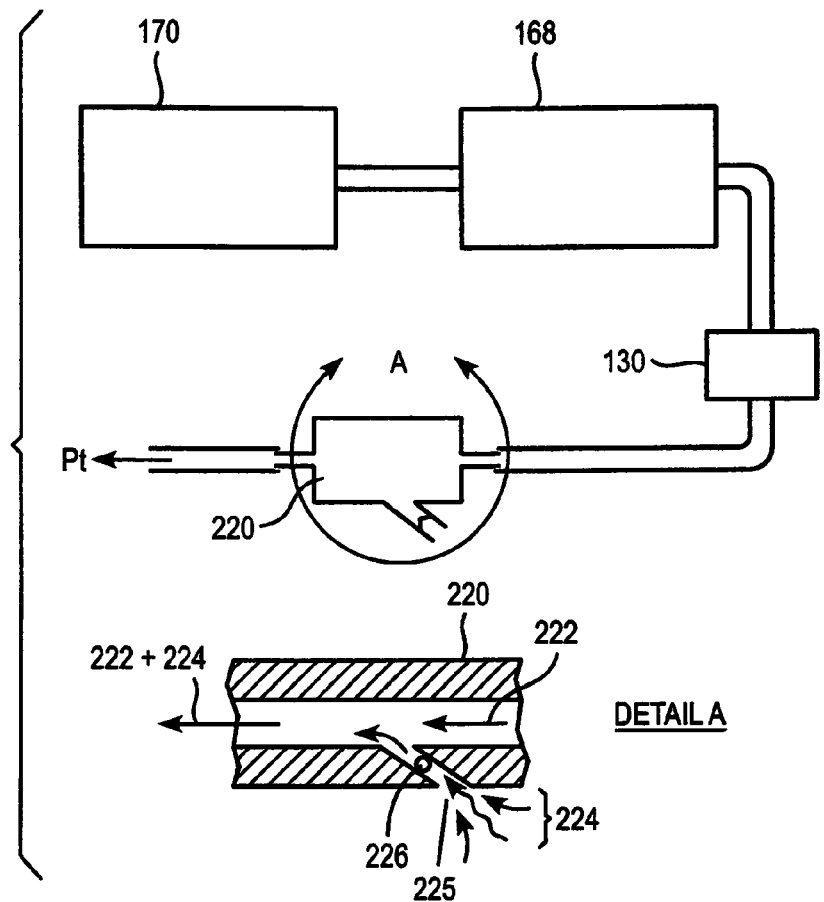
DETAIL A
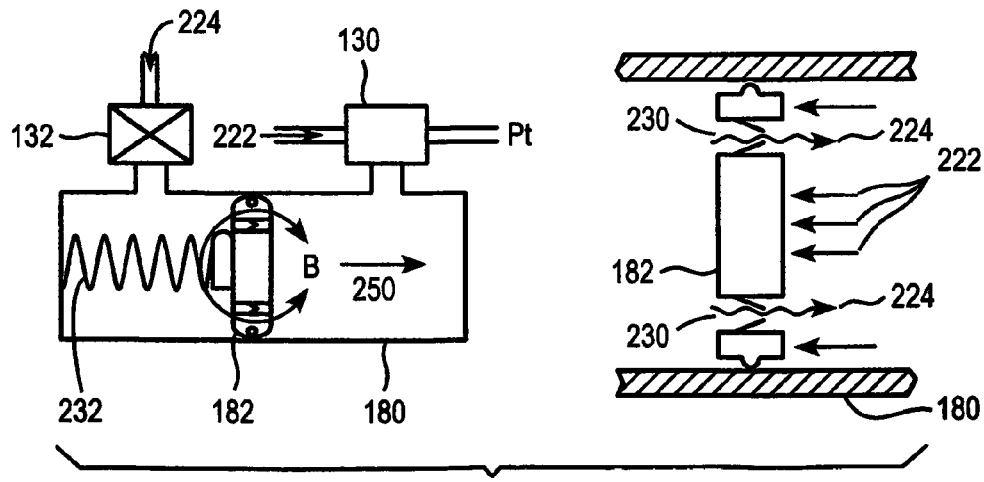
FIG. 14b

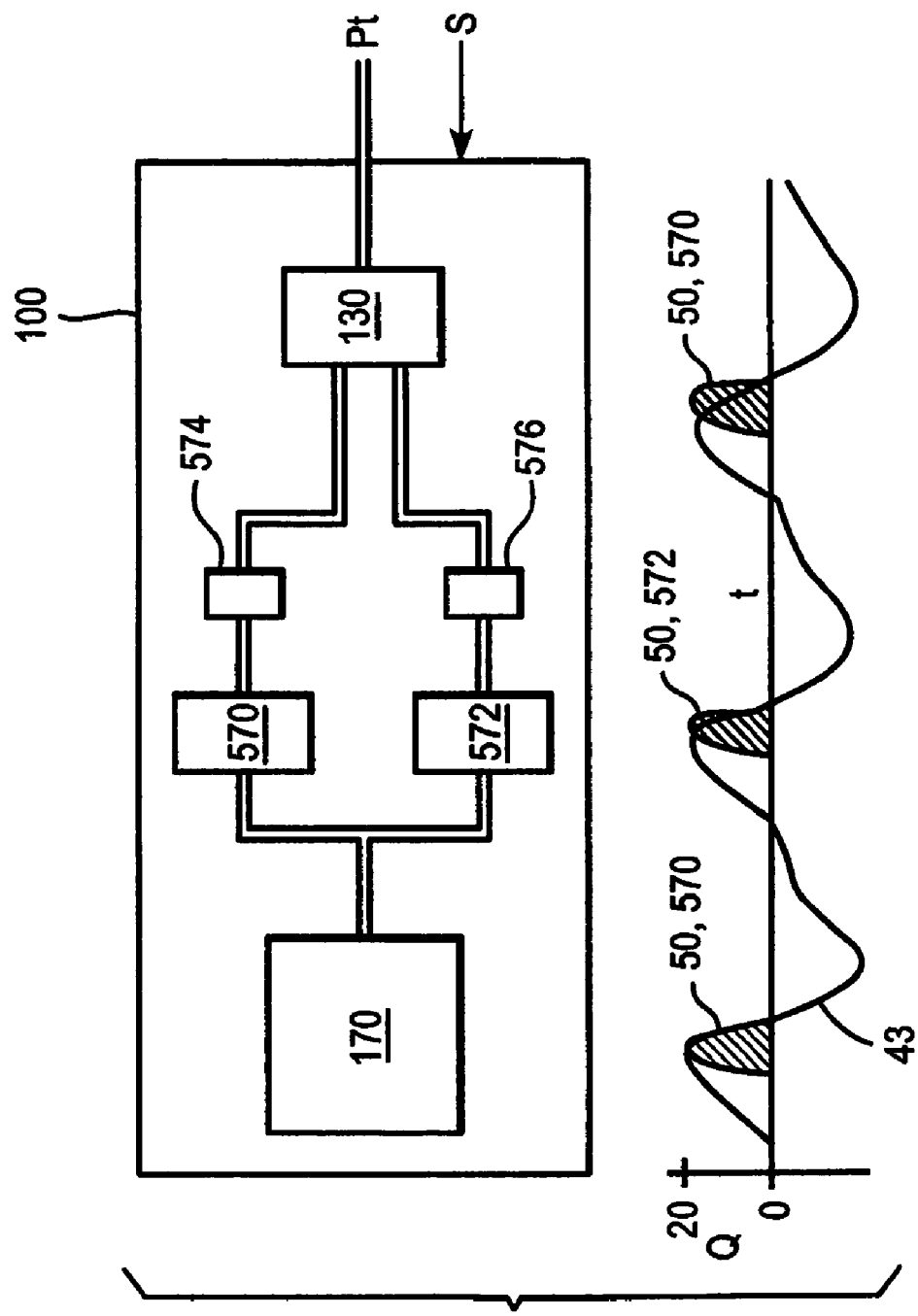

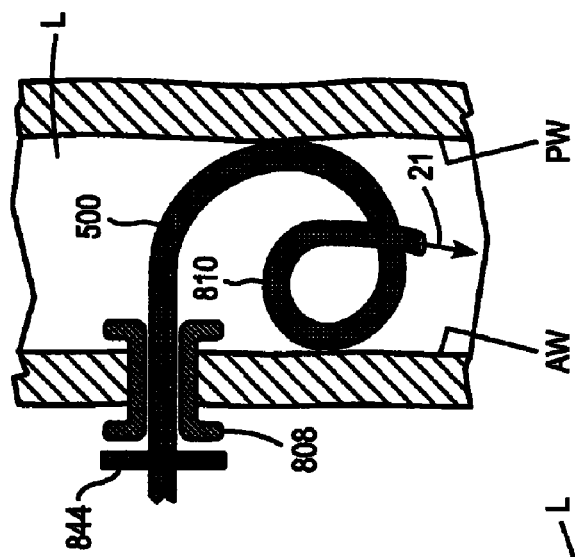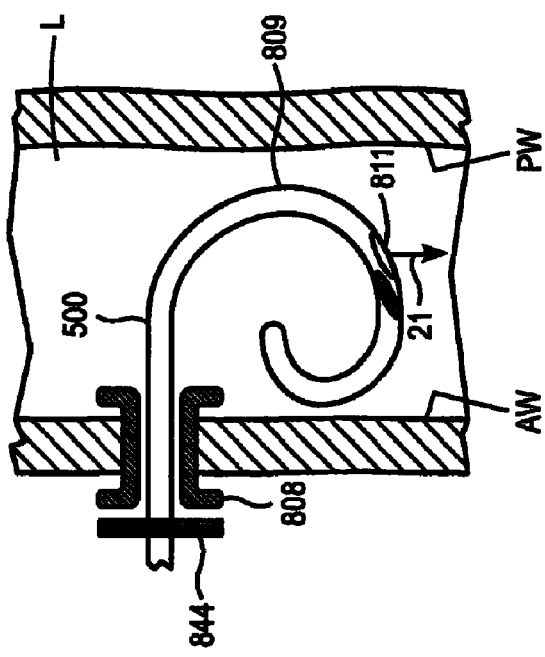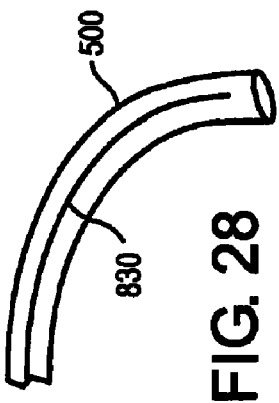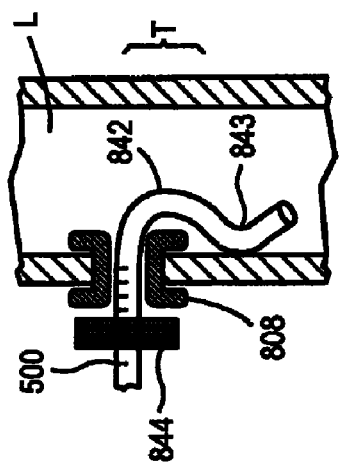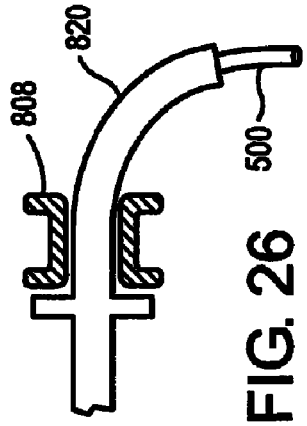

METHODS AND DEVICES FOR MINIMALLY INVASIVE RESPIRATORY SUPPORT

PRIORITY CLAIM

This application is a continuation-in-part of U.S. patent application Ser. No. 10/870,849, entitled "Methods, Systems and Devices for Improving Ventilation in a Lung Area", filed Jun. 17, 2004, which claims priority to U.S. provisional patent application Ser. No. 60/479,213, filed Jun. 18, 2003, the disclosures of each of which are incorporated herein by reference in their entireties.

This application is also a continuation-in-part of US. patent application Ser. No. 10/771,803, entitled "Tracheal Catheter and Prosthesis and Method of Respiratory Support of a Patient", filed Feb. 4, 2004, which claims priority to German patent application Serial Number 10337138.9, filed Aug. 11, 2003, the disclosures of each of which are incorporated herein byreference in their entireties.

This application is also a continuation-in-part of US. patent application Ser. No. 10/567,746, entitled "Tracheal Catheter and Prosthesis and Method of Respiratory Support of a Patient Airway Prosthesis and Catheter", filed Feb. 10, 2006, which is a national stage application of PCT patent application PCT/DE2004/001646, entitled "Method and Arrangement for Respiratory Support for a Patient Airway Prosthesis and Catheter ", filed Jul. 23, 2004, and which in turn claims priority to German patent application Serial Number 103 37 189.9, filed Aug. 11, 2003, the disclosures of which are incorporated herein byreference in their entireties.

This application also claims priority to U.S. provisional application Ser. No. 60/835,066, entitled "Methods and Devices for Minimally Invasive Respiratory Support", filed Aug. 3, 2006, the disclosure of which is incorporated herein by reference in its entirety.

FIELD OF THE INVENTION

This invention relates to ventilation therapy and oxygen therapy for persons suffering from respiratory impairment, such as chronic obstructive pulmonary disease (COPD), pulmonary fibrosis, and acute respiratory distress syndrome (ARDS).

BACKGROUND OF THE INVENTION

The following documents may be considered related art:
Patent Application PCT/DE2004/001646, Freitag, L; Method and arrangement for respiratory support for a patient airway prosthesis and catheter
U.S. Patent Application 20050005936, Wondka; Methods, systems and devices for improving ventilation in a lung area
U.S. Pat. No. 5,419,314, Christopher; Method and apparatus for weaning ventilator-dependent patients
U.S. Patent Application 20050247308, Frye, Mark R.; High efficiency liquid oxygen system
U.S. Pat. No. 4,938,212, Snook; Inspiration oxygen saver
Transtracheal Open Ventilation in Acute Respiratory Failure Secondary to Severe Chronic Obstructive Pulmonary Disease Exacerbation *American Journal of Respiratory and Critical Care Medicine* Vol 173. pp. 877-881, (2006), Cesare Gregoretti
Preliminary observations of transtracheal augmented ventilation for chronic severe respiratory disease. *Respir Care.* 2001 January; 46(1):15-25, Christopher K L Reduced inspiratory muscle endurance following successful weaning from prolonged mechanical ventilation. Chest. 2005 August; 128(2):553-9 *Chest.* 2005 August; 128(2): 481-3. Chang A T
A comparison in a lung model of low- and high-flow regulators for transtracheal jet ventilation. *Anesthesiology.* 1992 July; 77(1):189-99. Gaughan S D, Benumof J L
Tracheal perforation. A complication associated with transtracheal oxygen therapy. Menon A S—*Chest*—1 Aug. 1993; 104(2): 636-7
Dangerous complication of transtracheal oxygen therapy with the SCOOP® system. Rothe T B—*Pneumologie*—1 Oct. 1996; 50(10): 700-2

Patients suffering from respiratory impairment are underoxygenated due to deteriorating lung structure and are fatigued due to the strenuous work required to get air in and out of their compromised lungs. This work leads to patients becoming dormant to reduce their oxygen consumption to reduce their work of breathing (WOB) and in turn this dormancy leads to other health problems. Long term oxygen therapy (LTOT) is a gold standard therapy widely used for decades to assist patients suffering from respiratory impairment. Typically patients are provided 1-6 LPM of continuous oxygen flow into the nose via an oxygen nasal cannula. The supplemental oxygen increases the concentration of oxygen in the lung and alveolii therefore increasing the oxygen delivered to the body thus compensating for the patient's poor lung function. Improvements to LTOT have been more recently introduced such as transtracheal oxygen therapy (TTOT) and demand oxygen delivery (DOD). TTOT (U.S. Pat. No. 5,419, 314) is a potential improvement over LTOT in that the oxygen is delivered directly to the trachea thus closer to the lung and thus the oxygen is not wasted in the upper airway and nasal cavity. DOD systems (U.S. Pat. No. 4,938,212) have been devised to sense when the patient is inspiring and deliver oxygen only during inspiration in order to conserve the source of oxygen, a concern in the home care or ambulatory setting although not a concern in the hospital setting where the oxygen source is plentiful. LTOT, TTOT and DOD are useful in improving diffusion of oxygen into the tissues by increasing the oxygen level in the lung and bloodstream, but these therapies all have the drawback of not providing any real ventilatory support for the patient and the excessive WOB is not relieved, especially during the types of simple exertion which occur during normal daily activities, like walking or climbing stairs.

Continuous Positive Airway Pressure (CPAP) ventilation has been used extensively to provide ventilatory support for patients when LTOT alone is insufficient to compensate for a patient's respiratory impairment. However, CPAP is non-portable and is obtrusive to patients because of the nasal mask that must be worn. Further, CPAP can inadvertently train the respiratory muscles to become lazy since the neuromuscular system gets acclimated to the artificial respiratory support, a syndrome known within the respiratory medical community.

Transtracheal High Frequency Jet Ventilation (TTHFJV) as described by Benumof has also been used, for example for emergency ventilation, typically using a small gauge catheter introduced into the trachea. Frequencies are typically 60 cycles per minute or greater, driving pressures are typically around 40 psi, and flow rates are typically greater than 10 LMP therefore requiring a blended oxygen air mixture and heated humidification. TTHFJV is not a portable therapy and is not appropriate as a ventilation assist therapy for an ambulatory, spontaneously breathing, alert, non-critical patient.

Transtracheal Open Ventilation (TOV) as described by Gregoretti has been used as an alternative to mechanical ventilation which uses an endotracheal tube. The purpose of TOV is to reduce the negative side effects of invasive ventilation such as ventilator associated pneumonia. Typically a 4 mm catheter is inserted into a tracheostomy tube already in the patient and the other end of the catheter is attached to a conventional mechanical ventilator which is set in assisted pressure control mode and mechanical breaths are delivered into the trachea synchronized with the patients breath rate. However because the ventilator delivers a predetermined mechanical breath set by the user the ventilator is breathing for the patient and is not truly assisting the patient. TOV is non-portable and is designed to provide a high level or complete support of a patients respiration.

Transtracheal Augmented Ventilation (TAV) as described by Christopher is a therapy in which high flow rates typically greater than 10 LPM of a humidified oxygen/air blend are delivered continuously into the trachea or can be delivered intermittently or synchronized with the patients' breathing pattern. TAV is a good therapy to provide ventilatory support for patients with severe respiratory insufficiency, however TAV is not suitable for an ambulatory portable therapy because of the high flow and humidification requirement.

Current oxygen delivery therapies or ventilation therapies are either too obtrusive, or are not sufficiently compact or mobile, or are limited in their efficacy and are therefore not useful for the vast population of patients with respiratory insufficiency that want to be ambulatory and active while receiving respiratory support. Specifically a therapy does not exist which both (1) oxygen delivery to increase oxygen diffusion into the blood stream, and (2) ventilation support to relieve the WOB in a mobile device. The invention disclosed herein provides unique and novel solutions to this problem by providing an unobtrusive, ultra compact and mobile, clinically effective system that provides both oxygen diffusion support and ventilation support to address respiratory insufficiency.

SUMMARY OF THE INVENTION

The invention described herein includes s a method and devices wherein both oxygen delivery and ventilatory support are provided by percutaneous, transtracheal, inspiratory-synchronized jet-augmented ventilation (TIJV). The therapy is provided by an ultra compact wearable ventilator and a small gauge indwelling delivery catheter.

Additional features, advantages, and embodiments of the invention may be set forth or apparent from consideration of the following detailed description, drawings, and claims. Moreover, it is to be understood that both the foregoing summary of the invention and the following detailed description are exemplary and intended to provide further explanation without limiting the scope of the invention as claimed.

BRIEF DESCRIPTION OF THE FIGURES

The accompanying drawings, which are included to provide a further understanding of the invention and are incorporated in and constitute a part of this specification, illustrate preferred embodiments of the invention and together with the detail description serve to explain the principles of the invention. In the drawings:

FIG. 10 describes a piston and cylinder for amplifying the volume output of the present invention and for achieving a higher mean output pressure.

FIG. 13 describes adjusting the amplitude of the Venturi effect by catheter mechanisms.

FIG. 14 describes oxygen-air blending techniques to deliver different oxygen concentrations to the patient.

FIG. 16 describes a dual chamber system which alternates chambers for delivering gas to the patient.

FIG. 24 describes a 360 degree curved ventilation catheter tip to position gas delivery orifice in the center of the tracheal lumen.

FIG. 25 describes a 540 degree curved ventilation catheter tip to position the gas delivery tip in the center of the tracheal lumen.

FIG. 26 describes a thin wall outer cannula, stomal sleeve and inner cannula which is the ventilation catheter.

FIG. 27 describes a ventilation catheter with a bend shape to position the catheter against the anterior tracheal wall and the tip orifice at a distance from the anterior wall.

FIG. 28 describes a soft ventilation catheter with a stiffening or shaping member inside the catheter.

Figure 1A:
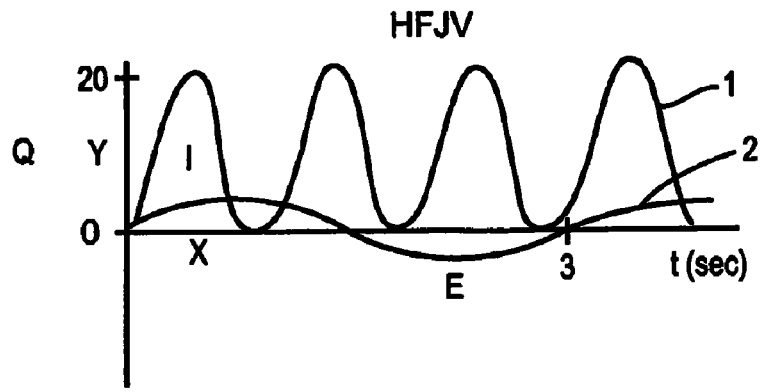
FIG. 1 describes graphically the difference between the present invention and the prior art.

| Reference Numerals |
| --- |
| Q: Flow rate in LPM |
| t: time in seconds |
| y: y-axis |
| x: x-axis |
| I: Inspiratory phase |
| E: Expiratory phase |
| V: Volume |
| Pt: Patient |
| S: sensor signal |
| P: lung or airway pressure |
| T: Trachea |
| L: Tracheal Lumen |
| W: Tracheal Wall |
| C: Carina |
| LL: Left Lung |
| RL: Right Lung |
| AW: Anterior Tracheal Wall |
| PW: Posterior Tracheal Wall |
| PTCr: positive temperature coefficient reference thermistor |
| PTC: positive temperature coefficient thermistor |
| NTCr: negative temperature coefficient reference thermistor |
| NTC: negative temperature coefficient thermistor |
| R: resistor |
| Prox: Proximal |
| Dist: Distal |
| LPM: liters per minute |
| L: liters |
| m/s: meters per second |
| cwp: centimeters of water pressure |
| cmH2O: centimeters of water pressure |
| cl: centerline |
|   1: HFJV flow curve |
|   2: Patient breathing flow curve |
|   10: High flow O2 therapy flow curve |
|   14: Long term oxygen therapy (LTOT)continuous flow |
|   15: Long term transtracheal oxygen therapy continuous flow curve |
|   16: LTOT pulse demand oxygen delivery (DOD) flow curve |
|   18: Mechanical Ventilator flow curve |
|   20: Patient spontaneous breath effort flow curve |
|   24: Continuous Positive Airway Pressure (CPAP) flow curve |
|   21: Transtracheal inspiratory augmentation ventilation (TIJV) flow curve |
|   25: Transtracheal inspiratory augmentation ventilation lung pressure curve |
|   30: Primary Breath sensor |
|   32: Dampened breath sensor |
|   34: Signal difference between primary breath sensor and dampened breath sensor |
|   36: Prior art pressure or flow sensor signal. |

| -continued |
| --- |
| Reference Numerals |
|   38: Drift in 36 |
|   40: Artifact in 36 |
|   42: First order differential of 34 |
|   43: Patient volume curve |
|   44: LTOT volume curve |
|   46: LTOT DOD volume curve |
|   50: TIJV volume curve |
|   52: Increase in TIJV amplitude |
|   54: Adjustment of TIJV timing to earlier |
|   56: Adjustment of TIJV timing to later |
|   58: Secondary TIJV volume curve |
|   60: Secondary ventilation gas flow |
| 100: Ventilator |
| 101: Battery |
| 102: Counterflow delivery valve |
| 103: Gas evacuation delivery valve |
| 104: Medicant delivery unit |
| 105: Biofeedback signal |
| 110: Liquid Oxygen (LOX) unit |
| 112: LOX reservoir |
| 114: Vacuum chamber |
| 116: LOX exit tube |
| 120: Heater |
| 122: Check valve |
| 124: Heat Exchanger |
| 126: Pressure regulator |
| 127: $2^{nd}$ Pressure regulator |
| 128: Oxygen gas reservoir |
| 129: Toggle switch |
| 130: Outlet On/Off valve |
| 131: Pressure regulator manifold |
| 132: Reservoir/accumulator inlet valve |
| 140: O2 gas cylinder output regulator with >0.1" diameter orifice |
| 160: Oxygen concentrator unit |
| 162: Pump |
| 164: Pressure amplifier |
| 166: Pressure regulator |
| 168: Gas reservoir/accumulator |
| 170: Gas supply |
| 180: Cylinder |
| 182: Piston |
| 183: Valve ball |
| 210: Insufflation gas flow |
| 220: Venturi mixing valve |
| 222: Ventilation Gas |
| 224: Ambient Air |
| 225: Venturi inlet port |
| 226: Venturi check valve |
| 230: Piston check valve |
| 500: catheter |
| 501: Breath sensor |
| 502: catheter ventilation gas exit port |
| 504: catheter insufflation gas exit port |
| 506: gas exit nozzle |
| 510: Nozzle restrictor element |
| 512: Nozzle restrictor element in low Jet position |
| 514: Nozzle restrictor element in high Jet position |
| 520: Nozzle restrictor slide |
| 522: Nozzle restrictor slide in low Jet position |
| 524: Nozzle restrictor slide in high Jet position |
| 530: Reservoir inlet check valve |
| 540: Pressure amplifier inlet stage |
| 542: Pressure amplifier inlet gas drive pressure |
| 544: Pressure amplifier outlet stage |
| 546: Pressure amplifier outlet pressure |
| 548: Pressure amplifier gas supply |
| 550: Pressure amplifier filter |
| 552: Pressure amplifier gas supply regulator |
| 554: Pressure amplifier gas drive inlet |
| 556: Pressure amplifier gas supply inlet |
| 558: Pressure amplifier gas supply outlet |
| 570: Accumulator A1 |
| 572: Accumulator A2 |
| 574: Accumulator A1 outlet valve |
| 576: Accumulator A2 outlet valve |
| 590: Volume Control valve gas inlet |
| 591: Volume Control valve variable orifice |
| 592: Volume Control valve body |

-continued

| Reference Numerals |
|---|
| 593: Volume Control Valve needle |
| 594: Volume Control valve outlet |
| 596: Volume Control valve outlet pressure sensor |
| 598: Volume Control valve adjustment signal |
| 600: Accumulator inlet check valves |
| 602: Accumulator A |
| 604: Accumulator B |
| 606: Accumulator C |
| 608: Valve A |
| 610: Valve B |
| 612: Valve C |
| 614: Manifold |
| 616: Orifice 1 |
| 618: Orifice 2 |
| 620: Orifice 3 |
| 640: Piston Outlet Chamber |
| 650: Moving End Cap |
| 652: Thread system |
| 654: Adjustment Knob and screw |
| 656: Adjustment drive belt |
| 658: Rotational position sensor |
| 660: End Cap position sensor |
| 232: Piston Augmentation stroke spring |
| 250: Augmentation Stroke |
| 252: Refill Stroke 662: Pneumatic adjustment line |
| 720: Exhalation counter-flow flow curve |
| 722: Increased exhaled flow |
| 724: Oscillatory counter-flow curve |
| 726: sine wave counter-flow curve |
| 728: Short pulse counter-flow curve |
| 730: Ascending counter-flow curve |
| 732: Multiple pulse counter-flow curve |
| 734: Descending counter-flow curve |
| 760: Non-uniform velocity profile |
| 762: Non-diffuse gas exit |
| 764: Uniform velocity profile |
| 766: Diffuse gas exit |
| 780: Gas evacuation flow curve |
| 800: Concave accumulator/reservoir |
| 802: Accumulator cylinder array |
| 804: Ventilator enclosure |
| 805: Hollow bilayer casing |
| 806: Conduit Accumulator |
| 808: Stomal Sleeve |
| 809: Catheter 360 degree bend |
| 810: Catheter 540 degree bend |
| 811: Gas exit port |
| 820: Guiding Cannula |
| 830: Stiffening member |
| 840: Anterior wall spacer |
| 842: Catheter anterior curve |
| 843: Catheter posterior curve |
| 844: Adjustable Flange |
| 850: Centering/anchoring basket |
| 860: Short Trach Tube |
| 864: Catheter 90 degree bend |
| 870: Stomal seal |
| 900: external catheter section |
| 902: internal catheter section |
| 904: non-Jet catheter |
| 906: Jet catheter |
| 908: Signature tag |
| 910: Recognition tag |
| 920: Sleeve external flange |
| 922: Sleeve unfolded internal flange |
| 924: Folded internal flange |
| 930: Flange release cord |
| 952: signal output 1 |
| 954: signal output 2 |
| 960: Wheatstone bridge circuit |
| 962: Thermistors arrangement exposed to inhaled or exhaled flow |
| 964: Thermistors arrangement exposed and less exposed to airflow |
| 980: Exhalation Counterflow unit |
| 982: Gas evacuation unit |
| 984: Medicant delivery unit |
| 986: Biofeedback signal |
| 988: Auxiliary Flow |

DETAILED DESCRIPTION OF PREFERRED EMBODIMENTS

FIG. 1 and Tables 1 and 2 describe the ventilation therapy of the present invention in contrast to conventional therapies. In a main embodiment of the invention a ventilation method is described in which a patient's respiration is augmented by certain ventilation-oxygen delivery parameters, delivered directly into the trachea with an indwelling percutaneous transtracheal catheter coupled to a highly compact light weight portable ventilation apparatus worn or carried by the patient, subsequently referred to as Transtracheal inspiratory-synchronized jet-augmented ventilation (TIJV). Jet pulses of gas are delivered into the trachea in synchrony with the patient's inspiratory phase.

Figure 1B:
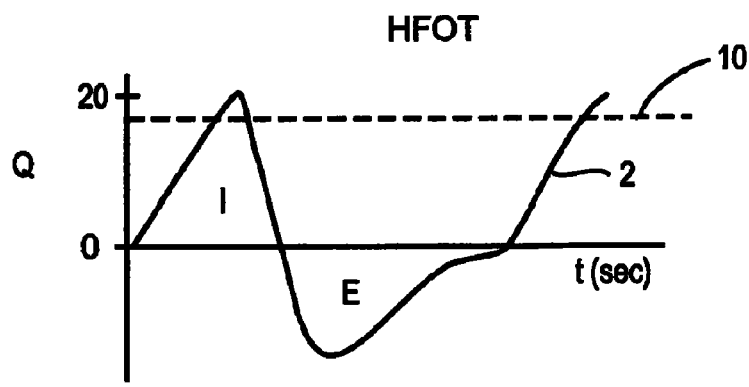
Figure 1C:
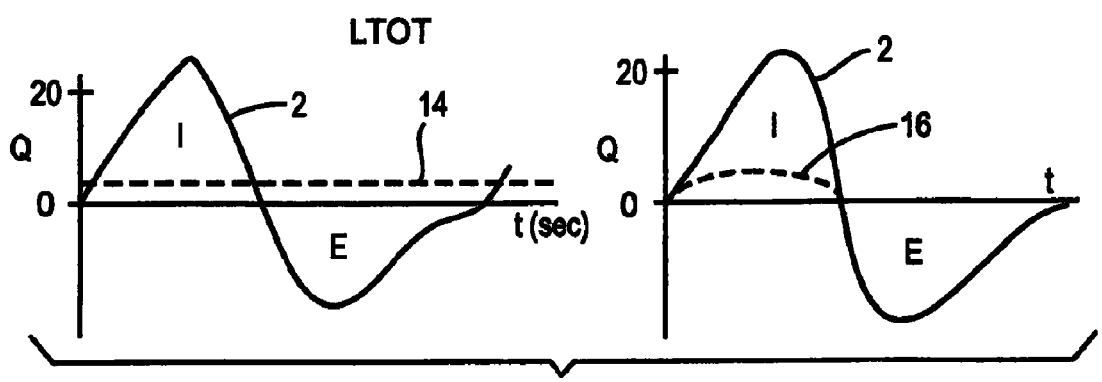
Figure 1D:
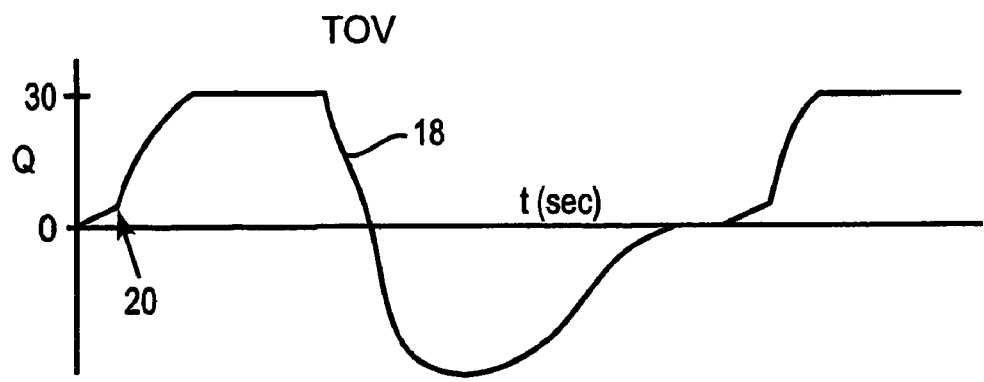
Figure 1E:
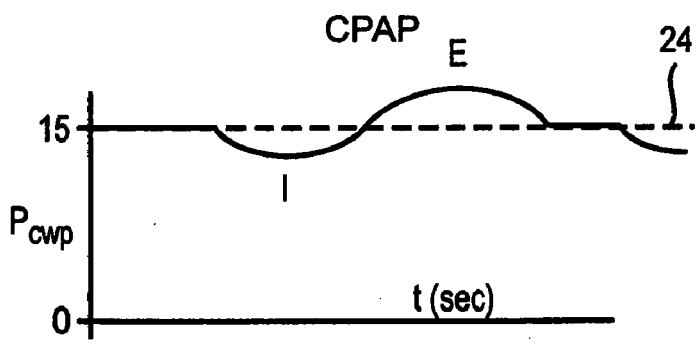
Figure 1F:
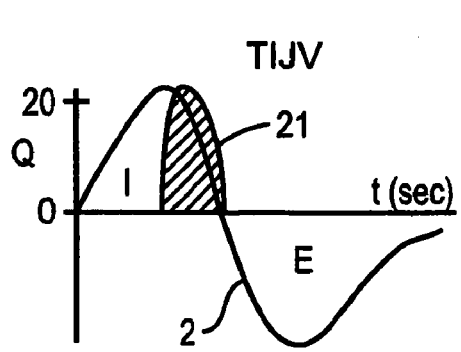
Figure 1G:
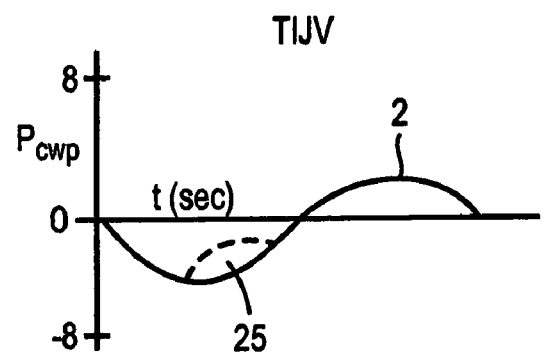

FIGS. 1f and 1g describe TIJV and for comparison FIGS. 1a-1e describe the conventional therapies. In FIG. 1a, HFJV is shown, indicating the patient breathing flow curve 2 at around 20 breaths per minute. The Jet Ventilator flow curve 1 is asynchronous with the patient's breath cycle and cycling at a rate of around 60 cycles per minute. FIG. 1b describes high flow oxygen therapy (HFOT). HFOT gas source flow is applied to the patient continuously as seen by the HFOT flow curve 10. FIG. 1c describes Transtracheal Oxygen Therapy (TTOT) and Pulse Demand Oxygen Delivery (DOD) therapy and the respective flow curves 14 and 16. TTOT applies continuous flow 14 to the patient, typically 1-6 LPM and DOD delivers a low flow pulse oxygen flow 16 during inspiratory phase I. FIG. 1d describes Transtracheal Open Ventilation (TOV) in which a mechanical breath 18 is delivered from a conventional intensive care ventilator when a patient breath effort 20 is detected. FIG. 1e describes Continuous Positive Airway Pressure (CPAP) ventilation in which the lung pressure P of the patient is elevated to the CPAP pressure setting 24.

Now referring to FIGS. 1f and 1g, the TIJV flow curve 21 is shown to be in synchrony with the patient's inspiratory phase I and more pronounced than DOD. As can be seen by the change in lung pressure due to TIJV 25, the therapy increases the lung pressure in the patient, thus helping the patient's respiratory muscles and showing that TIJV ventilation gas is penetrating deep in the lung.

The gas is delivered at a frequency that matches the patient's breath frequency, typically 12-30 cycles per minute, thus at a relatively low frequency compared to HFJV which is typically 60 cycles per minute. A low minute volume of gas is delivered relative to CPAP, HFJV and HFOT, typically 25 ml-150 ml per breath, or typically 10-25% of the patient's tidal volume requirement. The gas source supply flow rate is relatively low compared to CPAP, HFJV and HFOT, typically 4-8 lpm, and the incoming pressure requirement for the ventilator is relatively low relative to CPAP, HFJV and HFOT, typically 10-30 psi. The gas can typically be delivered to the patient without adding artificial humidification as opposed to CPAP, HFJV and HFOT which requires heated humidification.

The gas delivery velocity, typically 25-400 meters/second, is fast relative to LTOT and DOD which are typically around 10 meters/second. The jet effect allows for better penetration of oxygen into the lungs. The relatively fast gas exit velocity also causes a Venturi effect at the catheter gas exit point which entrains and pulls into the lung gas volume from above the catheter which is typically 5-100% of the volume delivered by the catheter. This entrained gas is naturally humidified and has a beneficial effect of adding to the mechanically delivered gas to extend the benefit of the therapy but without risking drying the lower airways and without risking inadvertent aspiration of saliva from the mouth or gastric contents from the esophagus into the airway due to the relatively low frequency compared to HFJV. In HFJV therapy, 50-75% gas volume (as a percentage of the delivered gas) is entrained from the upper airway but at 60 cycles per minute risking aspiration and compromising speech. HFJV is only useful in acute critical situations.

The gas source supply in TIJV is typically either a liquid oxygen source (LOX), a compressed oxygen source, or an oxygen generation source. The system is an ultra compact portable system, lasting typically 2-8 hours depending on the size of the gas source, to maximize the mobility of the patient. With the unique TIJV parameters therefore, the pulsed gas delivery is designed to augment the patient's bulk ventilatory gas exchange, assist the respiratory muscles in breathing but without making them lazy, as well as to improve oxygen delivery, thus positively effecting both ventilation and diffusion.

In DOD therapy, gas is always delivered in slow low volume pulses (<6 LPM) into the airway typically through the nasal route, thus effecting diffusion but not ventilation. Thus the invention herein is different from DOD therapy in that the gas pulses are delivered in a faster and higher volume pulse and at 12-30 LPM volumetric flow rate compared to 1-6 LPM volumetric flow rate in DOD, and therefore provides both ventilation and diffusion improvement, rather than just diffusion improvement as in DOD.

It should be noted that conventional volume controlled or pressure controlled ICU-type ventilators have the ability to deliver assisted breaths upon sensing inspiration from the patient as described by Gregoretti in transtracheal open ventilation (TOV). However, in TOV, the ventilator delivers a full or substantially full mechanical breath to the patient and dominates the patient's breathing mechanics rather than truly assisting the patient. Although not yet described in the medical community, these ventilators could be set to deliver the same pressure or volume as in TIJV. However, these types of mechanical ventilators are designed for the patient to both receive mechanical breaths and exhale that breath volume back through the large bore breathing circuit attached to the ventilator. In TIJV, there is no exhalation by the patient out through the jet catheter to the ventilator, rather all the exhale gas exits the natural breath routes. If using a conventional ventilator which by design expects to detect exhaled gas exiting the breathing circuit, the ventilator would suspect a leak in the system since there would be no exhaled gas detected and a fault condition would be triggered and the ventilator function interrupted. Therefore, conventional ventilators can not be used to deliver TIJV therapy. In fact, there would be numerous alarms and ventilator inoperative conditions triggered if attempting to use a conventional ICU ventilator to deliver the therapeutic parameters through a small bore ventilation catheter. It is neither clear or obvious how these traditional ventilators could be modified to perform TIJV, and as such, a whole new ventilator design is required to perform TIJV. Further, due to their design, conventional ventilators are inherently heavy, non-compact and not suitable for ambulatory TIJV therapy. A key to TIJV is that its light weight and small size makes it conducive to ambulatory therapy. Ideally, a TIJV ventilator, including gas source and battery should be less than 5.5 lbs in order for it to be successfully embraced by users.

Table 1 describes the output of TIJV ventilation compared to oxygen therapy devices, indicating the fundamental differences in outputs.

TABLE 1

Output of Therapeutic Gas Source Systems

| Source Output | TIJV | LOX Pulse | LOX Cont. | Compressed Gas Pulse | Compressed Gas Cont. | O2 Concentrator Pulse | O2 Concentrator Cont. |
|---|---|---|---|---|---|---|---|
| Pressure Output (dead ended, no flow, psi) | 10-30 | 22 | 22 | 50 | 50 | 5 | 2 |
| Pressure Output, open to 4' 3 mm inner diameter catheter (psi) | 8-15 | <5 | <5 | 10 | 5 | 3 | 1 |
| Flow Output, open to 4' 3 mm inner catheter (lpm) | 12-30 | <6 | <4 | 1-12 | 1-12 | 4 | 2 |

Table 2 describes in more detail the output of TIJV.

TABLE 2

| Parameter | TIJV Therapy Description<br>TIJV<br>Transtracheal inspiratory-synchronized Jet-augmented ventilation |
|---|---|
| Indications | Ambulatory use for respiratory insufficiency |
| Configuration | Wear-able ventilator, fully equipped with oxygen supply and battery, with transtracheal ventilation catheter, used for open ventilation |
| Description | Patient's natural inspiration is mechanically augmented by a burst of oxygen rich gas |
| Access | Mini-trach (3-5 mm) or via existing tracheostomy tube (4-10 mm) or guiding cannula (4-10 mm) |
| Volume delivered per cycle (mililiters) | 25-250<br>5-50% of tidal volume |

TABLE 2-continued

TIJV Therapy Description

| Parameter | TIJV<br>Transtracheal inspiratory-synchronized Jet-augmented ventilation |
|---|---|
| Peak pressure in catheter (centimeters of water pressure) | 70-200 |
| Lung pressure during delivery (centimeters of water pressure) | raised but still negative |
| Peak Flow (liters per minute) | 12-50 LPM |
| Insp. Time (sec) | 0.1-0.8 |
| Rate (breaths per minute) | Patient's rate |
| Timing | Delivered at most comfortable point during patient's spontaneous breath, such as during peak inspiratory flow, or after muscles have reached maximum work, or early in inspiration |
| Synchronization | Patient decides breath pattern |
| Breath Sensing | Yes. Senses spontaneous airflow stream directly in airway |
| Gas exit Velocity (meters per second)/Entrainment (%) | 25-250/5-100 |
| Humidification | Not required |

In the main embodiment of the present invention, the breathing pattern is sensed for the purpose of timing and controlling the delivery of the TIJV augmentation volume delivery pulse. FIG. 2 describes an embodiment of using breath sensors which compensate for drift and artifacts. Various sections of the breathing curve are distinguished by analyzing the information from the breath sensors. For example, by taking the derivative of the breathing curve, different sections of the breathing curve can be discerned. For example, the change in sign would indicate the point in inspiration when the inspired flow stops increasing and starts decreasing. Or, different points between the start of inspiration and the end of inspiration could be discerned. These different characteristic points can then be used to trigger and time the delivery of the augmentation pulse.

Figure 2A:
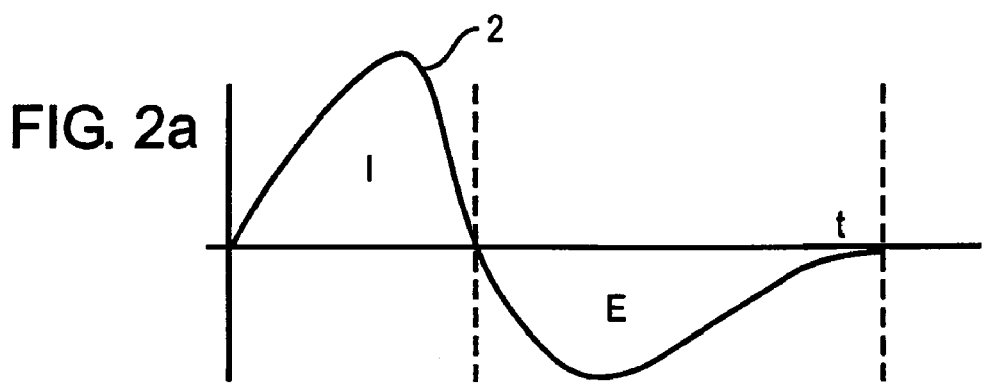
FIG. 2 describes comparing two sensors for compensating for drift and artifacts and differentiating the comparison to correlate the signal to the breathing curve.
Figure 2B:
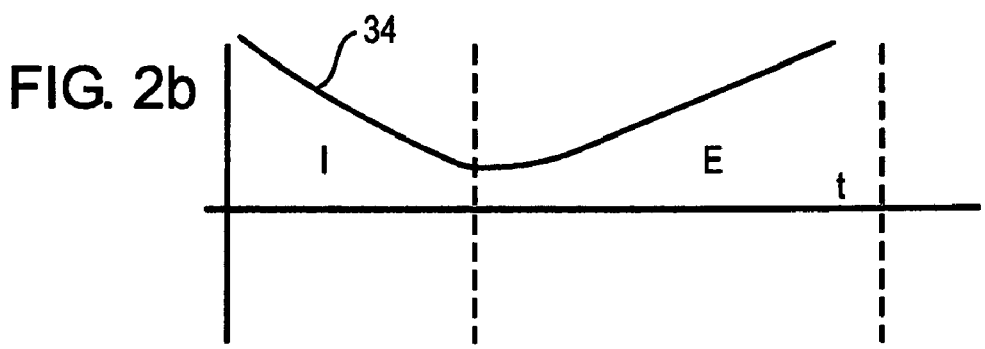
Figure 2C:
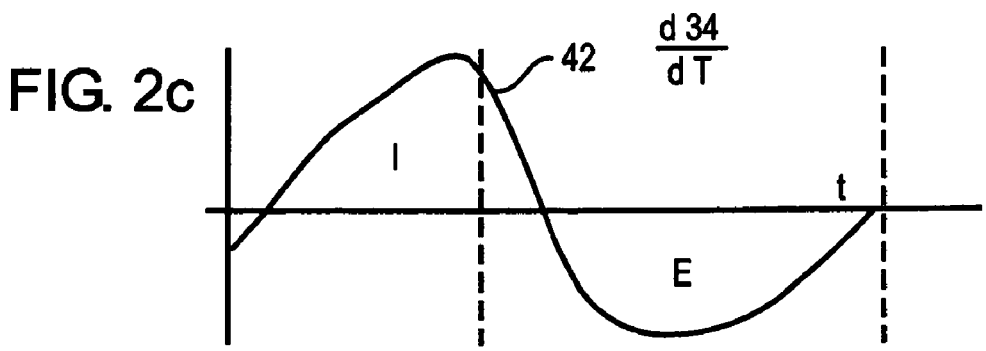
Figure 2D:
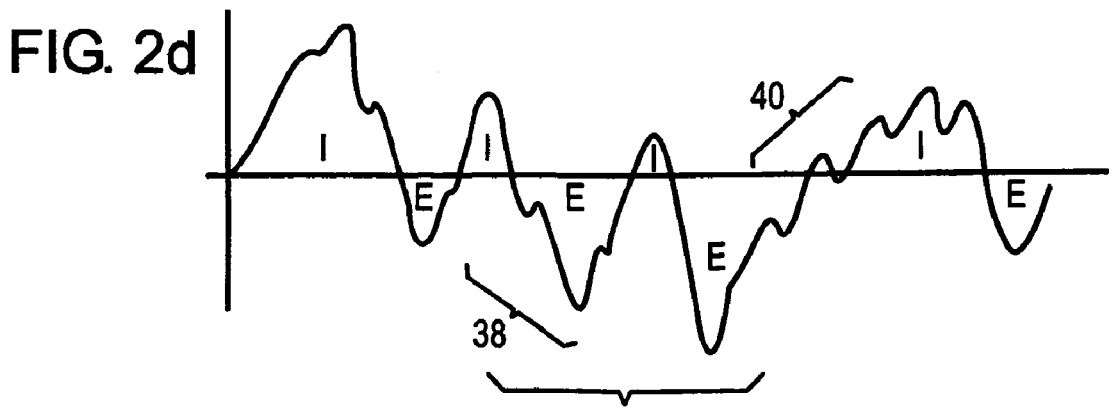

FIG. 2a describes the patient breath flow curve 2, and a primary breath sensor signal 30 which lags the patient breath flow curve, and a dampened breath sensor signal 32 which lags the primary sensor signal. In FIG. 2b, the signal delta 34 between the primary and dampened sensor signals is plotted. The delta curve 34 therefore compensates for drift 38 or artifacts 34 that can be present in a typical breath sensing systems as shown in the prior art pressure or flow sensor signal 36 shown in FIG. 2c which is derived from the typical pressure or flow sensors that are commonly used. FIG. 2d shows the curve of the first order differential 42 of the signal delta curve 34.

Figure 3:
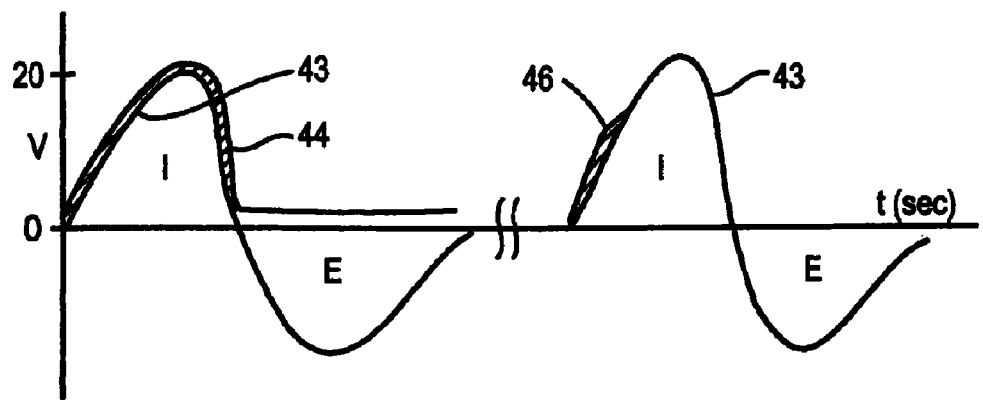
FIG. 3 graphically describes conventional oxygen therapy

In FIG. 3 conventional LTOT is described again, indicating the patient volume curve 43 and the LTOT volume curve 44. FIG. 4 describes again DOD showing the patient volume curve 43 and the DOD volume curve. DOD systems deliver the oxygen to the patient when the breath sensor senses inspiration has started. Other than the response time in the system, typically 100-200 msec., the oxygen is delivered as soon as the start of inspiration has been detected.

Figure 4A:
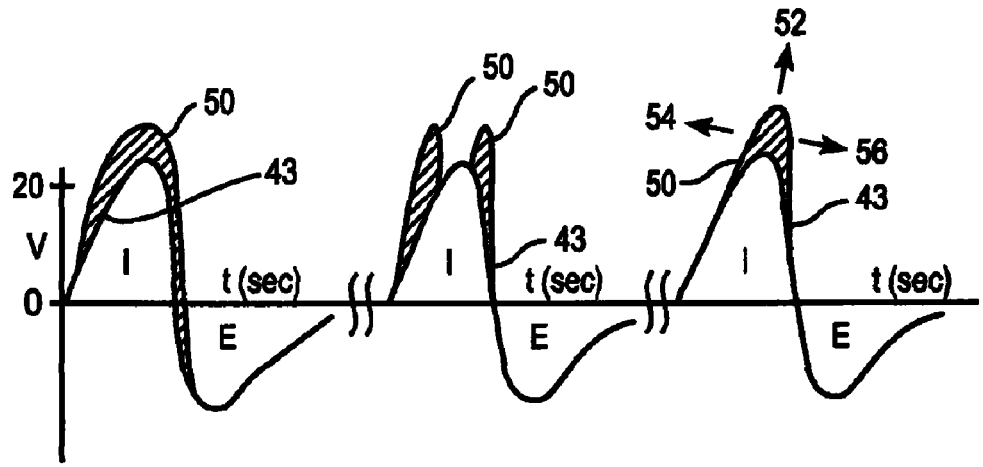
FIG. 4 graphically describes alternative ventilation delivery timing profiles for the present invention.
Figures 4B, 4C:
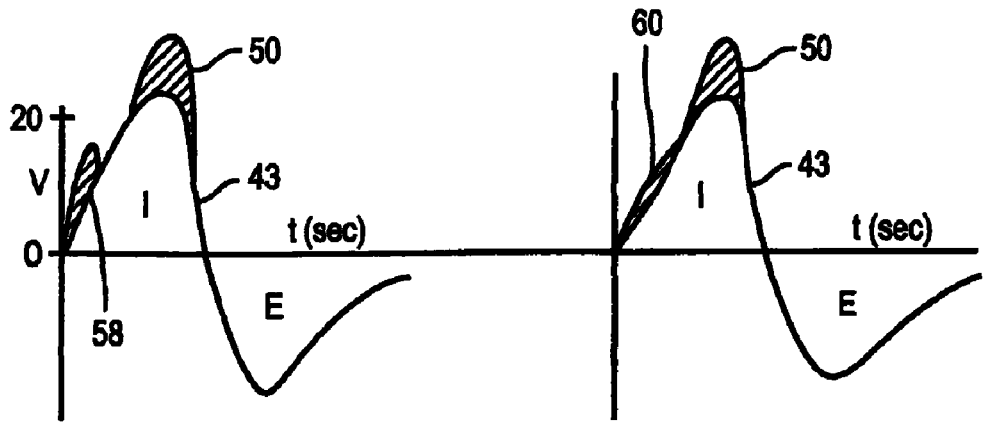

FIGS. 4a, 4b and 4c describe how the present invention is different from the existing systems in that the augmentation Volume pulse 50 pulse is more pronounced and can be delivered at any snategic time within the inspiratory phase I. For example, the augmentation pulse can be delivered in the later half of inspiration after the respiratory muscles have produced their work or most of their work which occurs in the initial "increasing flow rate" section of the inspiratory curve. When persons are ventilated while the respiratory muscles are working, it is known that these persons can neuromuscularly become lazy and will, over time, let the ventilator do more and more of the inspiratory work, thus weakening the persons inspiratory muscles which is undesirable. The present invention can avoid this problem by delivering the oxygen later in the inspiratory phase when the inspiratory muscles are not working or doing less work. Or, alternatively, the augmentation pulse can be delivered early in inspiration. For example, if the patient is under exertion, inspiratory flow is steep at the beginning of inspiration and hence a very early augmentation trigger maybe more comfortable, or if the patient is at rest, when the inspiratory flow curve is slow at the beginning of inspiration, a slight delay in the augmentation trigger time might be more comfortable. Further, in the present invention the start point of the augmented pulse delivery can be adjusted backwards and forwards in the inspiratory phase as desired, by manual adjustment or by automatic adjustment for example by a feedback from a respiratory parameter. The delivery time is typically 0.1 to 0.8 seconds, depending on the length of the person's inspiratory phase and I:E ratio. Further, in the main embodiment of the present invention, breath sensors are included on the catheter to directly measure inspiratory and expiratory air flow within the trachea, as opposed to all other prior art systems which if measuring the breathing curve measure air flow or air pressure in the catheter or breathing circuit lumen. Both flow directionality and flow amplitude are measured to discern both the phase of respiration and the depth of respiration throughout the entire breathing pattern. Prior art systems are only good at measuring the start of inspiration and no other portions of the breathing curve.

Also, in the present invention, multiple pulses can be delivered within inspiration, the pulse amplitude can be adjusted 52, the pulse can be moved earlier in inspiration 54 or moved later in inspiration 56. In addition a secondary lower volume augmentation pulse 58 can be delivered adjunctively to the augmentation volume pulse 50, or a secondary ventilation gas flow 60 can be delivered adjunctively to the augmentation volume pulse 50.

Further in the main embodiment of the present invention, FIGS. 5-19 describe unique pneumatic drive systems to provide the pressure and flow required for TIJV.

Figure 5:
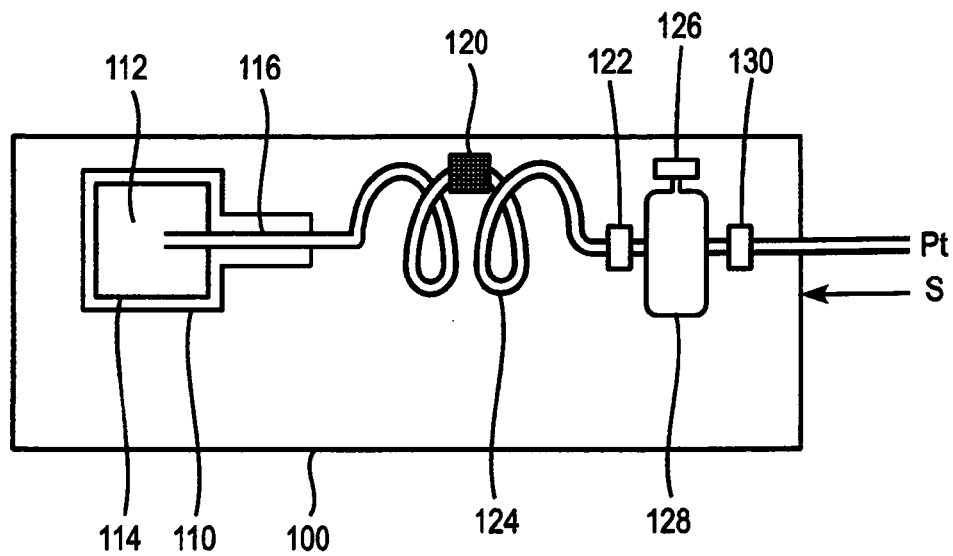
FIG. 5 describes a special liquid oxygen system for delivering the ventilation therapy of the present invention.

First, in FIG. 5 a unique LOX system is described to provide the pressure and flow required for TIJV, including a ventilator 100, LOX unit 110, LOX 112, LOX unit vacuum chamber 114, LOX outlet tube 116, heat exchanger 124, heater 120, check valve 122, oxygen gas reservoir 128, reservoir pressure regulator 126, gas outlet on/off valve 130, outlet to patient Pt and incoming breath signal S. Typical LOX systems include a liquid phase oxygen compartment and an oxygen gas phase compartment which is continually filled by the boiling of the liquid oxygen. The phase change is catalyzed by a heat exchanger unit. These systems maintain the gas phase compartment at about 23 psi by bleeding gas to atmosphere to avoid pressurization beyond 23 psi. Typical medical LOX systems have been designed specifically to conserve oxygen and as such their output is relatively weak compared to the requirements of TIJV. The compact LOX systems which are designed for portability are engineered to deliver gas at very low flow rates (<3 LPM) and low pressures (below 5 psi). The larger less portable LOX units are engineered for greater flow output however are not realistically suited for active ambulatory patients because of their larger size. The typical systems are capable of delivering oxygen gas at a continuous flow rate of below 4 liters per minute at a pressure well below 23 psi since the pressure in the gas phase compartment drops within fractions of a second when the system is opened to the patient. The gas phase compartment contains typically less than 50 ml of gas and the rate of gas creation by boiling is limited to below 4 liters per minute due to the design and construction of the heat exchanger which is typically less than 20 square inches surface area. Gas flow output to the patient is also limited by the size of the orifice in the outlet valve, typically less than 0.10" diameter, thus restricting airflow. In the present invention the heat exchanger unit 54 is designed with greater surface area, typically greater than 30 square inches, to produce gas at the rate of 6-10 liters per minute and the outlet orifice allows that flow rate output as well, typically greater than 0.15" diameter. A heater 56 may be added to increase the rate of production of gaseous 02. The gas volume of the gas phase compartment is typically above 80 ml and can be 250 ml, which typically includes a pressure regulator 60, a reservoir 58, check valve 66, on/off valve 62 and incoming breath signal 64. This unique design provides an oxygen gas output flowrate of above 6 LPM at above 20 psi continuously, thus meet the demands of the ventilation parameters required in TIJV. The unique LOX system includes a catheter and all the requisite sensing components and timing functions described earlier in order to deliver the required volume of gas at the correct pressure and at the correct time of the breathing curve.

Figure 6:
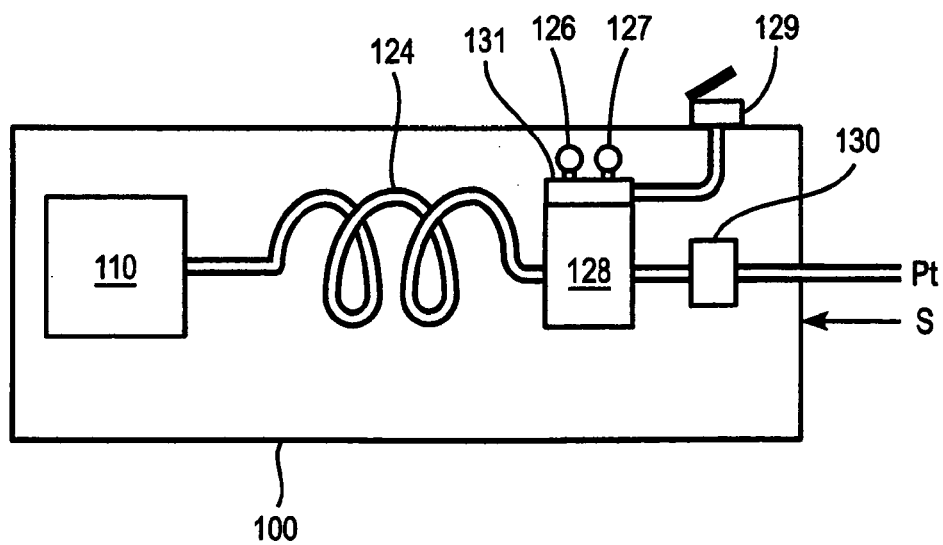
FIG. 6 describes a special liquid oxygen system with multiple outputs for delivering the ventilation therapy of the present invention.

In FIG. 6 an additional embodiment is shown comprising a, LOX system with two pressure settings. One low pressure regulator 126 with a setting of 23 psi to be used when the patient requires less powerful therapy or needs to conserve the LOX, and a higher pressure regulator 127 with a setting of for example 30-50 psi for increasing the output of the unit when needed or when conserving the LOX is not a concern. For example, when traveling on an airplane, the LOX system can be-set at the low 23 psi setting, and reset to the high setting after the flight or when arriving to the destination where there is a refill station. The two pressure regulators are configured in a manifold 131 which can be operated by a switch 129 to switch between settings. During flight, the patient can still receive the TIJV therapy but at a lower level of augmentation corresponding the to 23 psi setting, but after the flight and when the patient becomes more active again, the augmentation level can be increased because the pressure is set to the higher output setting. Two pressure settings are exemplary and it can be any number of pressure settings or even a continuous adjustment of the pressure setting between a minimum and maximum value.

Figure 7:
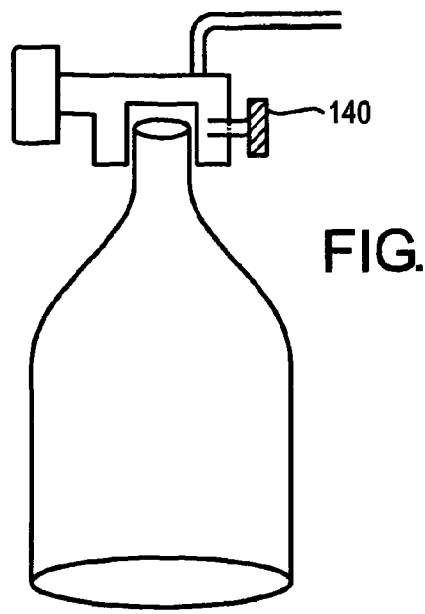
FIG. 7 describes a special compressed oxygen regulator for delivering the ventilation therapy of the present invention.

FIG. 7 describes an alternate embodiment in which a compressed oxygen gas source is combined with the TIJV ventilator features to create an integrated ventilator and gas source unit. The output regulator of the oxygen cylinder has a larger orifice than in a traditional oxygen therapy gas flow regulator, typically 0.1-0.2 inches in diameter, such that the flow output can be boosted to >6 LPM and meet the demands of TIJV.

Figure 8:
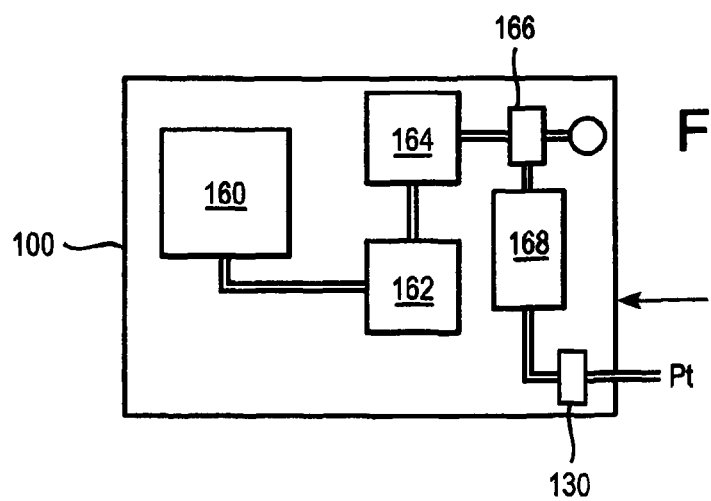
FIG. 8 describes a special high output oxygen generating system for delivering the ventilation therapy of the present invention.

In FIG. 8 an alternate embodiment to the present invention is shown comprising a unique oxygen generating device which can be used to provide the requisite ventilation parameters. An oxygen generator unit 160 is integrated into a ventilator 100 which includes a pump 162, a pressure amplifier 164, a gas reservoir/accumulator 168, a reservoir inlet regulator 166, and a reservoir outlet on/off valve 130. Typical oxygen generating devices produce a relatively weak output of oxygen (<2 LPM at <5 psi). By increasing the storage capacity and optionally including a pneumatic pressure amplifier, the output can be boosted to 4-10 LPM and 10-30 psi., thus powerful enough to meet the pressure and volume needs of TIJV. This unique oxygen generator system includes a catheter and all the requisite sensing components and timing functions described earlier in order to deliver the required volume of gas at the correct pressure and at the correct time of the breathing curve as required with TIJV therapy.

Figure 9:
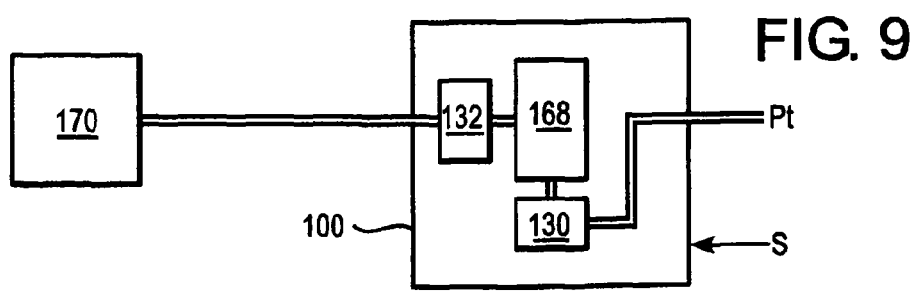
FIG. 9 describes converting conventional oxygen supplies into a ventilator for delivering the ventilation therapy of the present invention.

FIG. 9: In another main embodiment of the present invention, TIJV therapy can be accomplished by using a conventional gas source 170, such as a LOX systems, compressed gas tanks, or oxygen generator systems, but with a unique volume accumulator 168 and inlet valve 132 placed in between the gas source and the patient. The accumulator acts as a capacitor and stores a pressurized volume of gas close to the patient. The outlet of the accumulator is relatively unrestricted so that a relatively high flow rate can be delivered to the patient during the augmentation time and therefore meeting the requisite volume and pressure requirements. During the augmentation delivery period, the accumulator is depressurized to the patient through a valve which is switched open and during the non-augmentation time the accumulator is re-pressurized from the gas source by closing the patient valve and opening a valve between the accumulator and the gas source. Because the augmentation:non-augmentation time ratio is typically 1:2-1:3, the accumulator is able to be sufficiently re-pressurized in between augmentation pulses. Without the accumulator, the conventional gas supply systems do not have enough flow rate output and/or pressure output to meet the ventilation parameters of TIJV. A further benefit to this embodiment is safety; because of the valve configurations, if a valve where to fail open, only the cylinder volume could be delivered to the patient. This unique accumulator system is accompanied by all the requisite sensing components and timing functions described earlier in order to deliver the required volume of gas at the correct pressure and at the correct time of the breathing curve.

FIG. 10*a*: In another main embodiment of the present invention, TIJV therapy can be accomplished by using conventional gas sources (LOX systems, compressed gas or O2 concentrators), but with a unique cylinder and piston placed in between the gas source and the patient. Flow from the gas source 170 flows through an inlet valve 132 into a cylinder 180, moving a piston 182 while an outlet valve 130 is open to the patient Pt and closed to the gas source 170. A valve ball 183 or similar valve feature prevents the gas source from being directly connected to the patient. The cylinder stores a pressurized volume of gas similar to the accumulator system described previously in order to boost the flow rate to the patient to meet the TIJV requirements. In addition however the piston in the cylinder compresses the volume in the cylinder as the gas is being delivered to the patient, therefore reducing the pressure and flow rate decay occurring in the cylinder (due to the compression) and therefore boosting the volume delivered to the patient in a given period of time and maintaining peak pressure of the delivered gas for a longer period of time. A further benefit to this embodiment is safety, because of the valve configurations, if a valve where to fail open, only the cylinder volume could be delivered to the patient. This unique accumulator/piston system is accompanied by all the requisite sensing components and timing functions described earlier in order to deliver the required volume of gas at the correct pressure and at the correct time of the breathing curve. Comparison of FIGS. 10b which represents a cylinder 180 with no piston and FIG. 10c which represents a cylinder 180 with a piston 182, shows the increase in mean pressure output and volume caused by using the piston.

Figure 12:
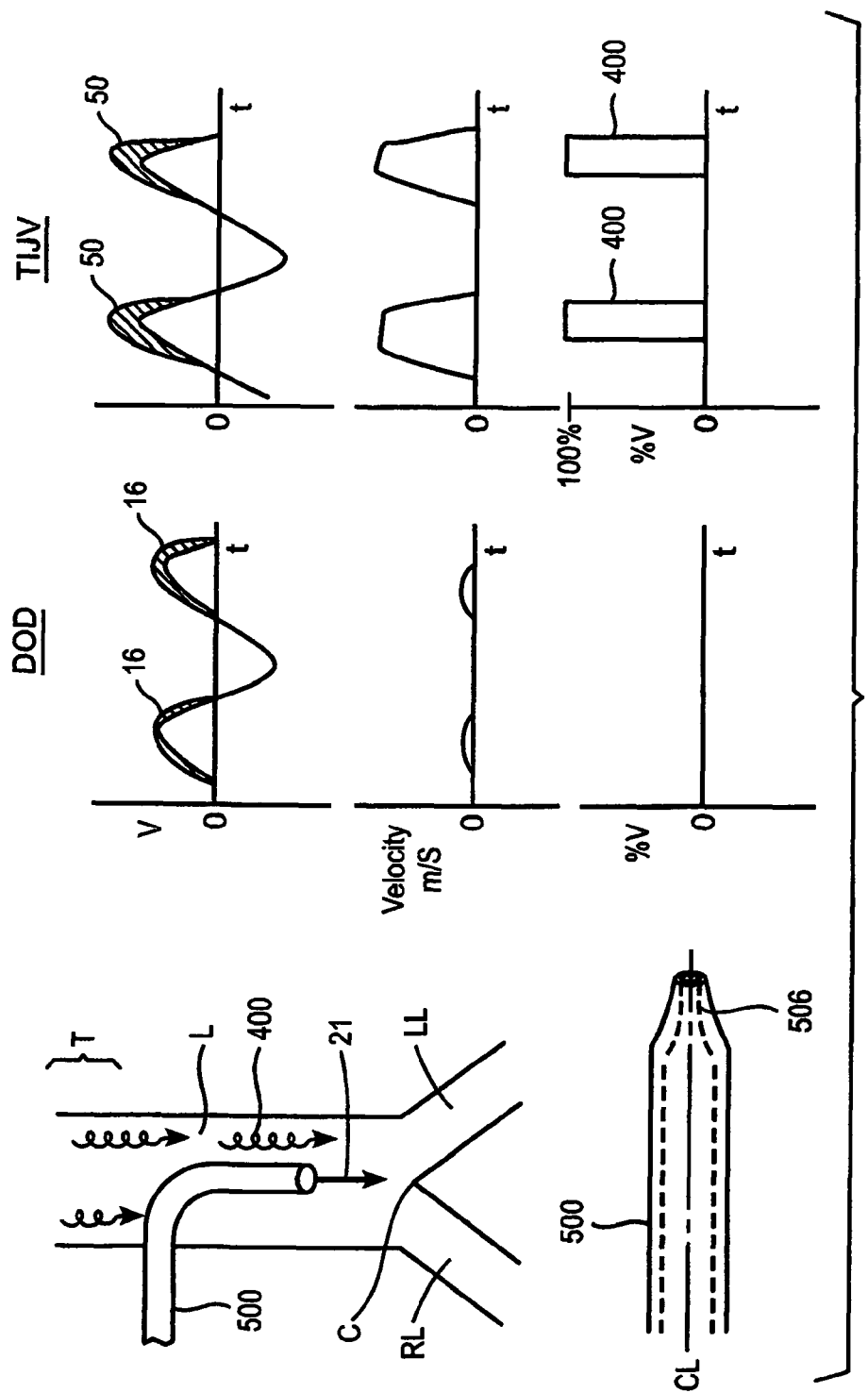
FIG. 12 describes the Venturi effect of the present invention.

FIG. 12 describes in more detail the jet effect of the invention. A unique catheter 500 is described to deliver the gas to the patient in the appropriate manner. The delivery catheter may include a nozzle 506 or diameter restriction at its distal tip (the patient end) located above the carina C in the lumen L of the trachea T. The nozzle is dimensioned so that the exit velocity of the gas is increased creating a venturi effect in the local area around the catheter tip. The venturi entrains air from the upper airway above the catheter and pulls that entrained air 400 into the left lung LL and right lung RL with the augmentation jet flow 21. Thus, the total amount of therapeutic gas provided to the patient is the TIJV augmented volume (VA) 50 being delivere from the ventilator, plus the entrained volume (VE) 400, thus adding to the ventilatory support provided by the VA alone. Since the VE is pulled from the upper airway, it is naturally humidified and in this manner, TIJV can be successful for longer periods of time without adding artificial humidification. Further, the exit velocity can be designed such that there is for example 50% entrainment, so that only half of the therapeutic volume comes from the ventilator, thus doubling the length of use of the portable oxygen supply being used. The jet can be tailored to provide 5%-100% entrainment, and if desired can even cause >100% entrainment. For comparison, the effects of TIJV are compared to DOD indicating TIJV increases entrained volume and reduces patient respiratory rate because the patient's breathing becomes less strenuous, whereas DOD does not effect these parameters.

Alternatively, as shown in FIG. 13 the nozzle dimensions at the tip of the catheter can be automatically and/or remotely adjustable, for example by moving an inner element or by inflating or deflating a element near the tip ID. For example a nozzle restrictor element 510 can be deflated 512 to produce a low jet output and can be inflated 514 to produce a high jet output. Or a nozzle restrictor slide 520 can be moved from less restricted nozzle position 522 to a more restricted position 524 to increase the jet effect. In this embodiment the nozzle would be adjusted to alter the percentage of entrained airflow, for example if the patient sensed dryness in the nasal cavity or sensed saliva being aspirated into the trachea, the amount of jet velocity could be reduced without removing the catheter in order to reduce the amount of entrained gas from above the catheter. Or if the patient needed more mechanical support then the jet could be increased. The jet adjustment could optionally be done automatically by use of physiological feedback signals.

FIGS. 14a and 14b: In a further embodiment of the present invention, ambient air can be mixed in with the oxygen gas being delivered with a low or no electrical power consuming mixing device. For example, ambient air can be mixed in with the pressurized oxygen by sucking the air in by creating a venturi effect with the pressurized flowing oxygen gas, or air can be added by the appropriate valving, or can be added by check valves in a mixing chamber, or can be added to mixing chamber with a small, low-power consumption pump. For example in FIG. 14a, a Venturi air mixing unit 220 is shown receiving oxygen rich gas 222 from a gas source, a venturi port 225 with check valve 226 for sucking in ambient air 224. Also for example in FIG. 14b a piston system is shown comprising a piston 182 with check valves 230 such that when the piston strokes 250 to deliver volume to the patient the check valves are closed, and when the piston performs a refill stroke, air enters the chamber through the check valves. Air 224 is brought into the cylinder 180 through an inlet valve 132 and oxygen rich ventilation gas 222 is brought into the cylinder through the outlet valve 130. Oxygen rich ventilation gas mixed with air is then released to the patient through the outlet valve. The addition of air into the oxygen gas extends the duration of use of the compact portable system. For example a system using a 1 liter cylinder of compressed oxygen can last 2 hours if the ventilator is delivering augmentation pulses of 100% oxygen, however if ambient air is mixed in so that the augmentation pulses are 50% oxygen and 50% nitrogen, then the 1 liter cylinder can last approximately 5 hours.

Figure 15:
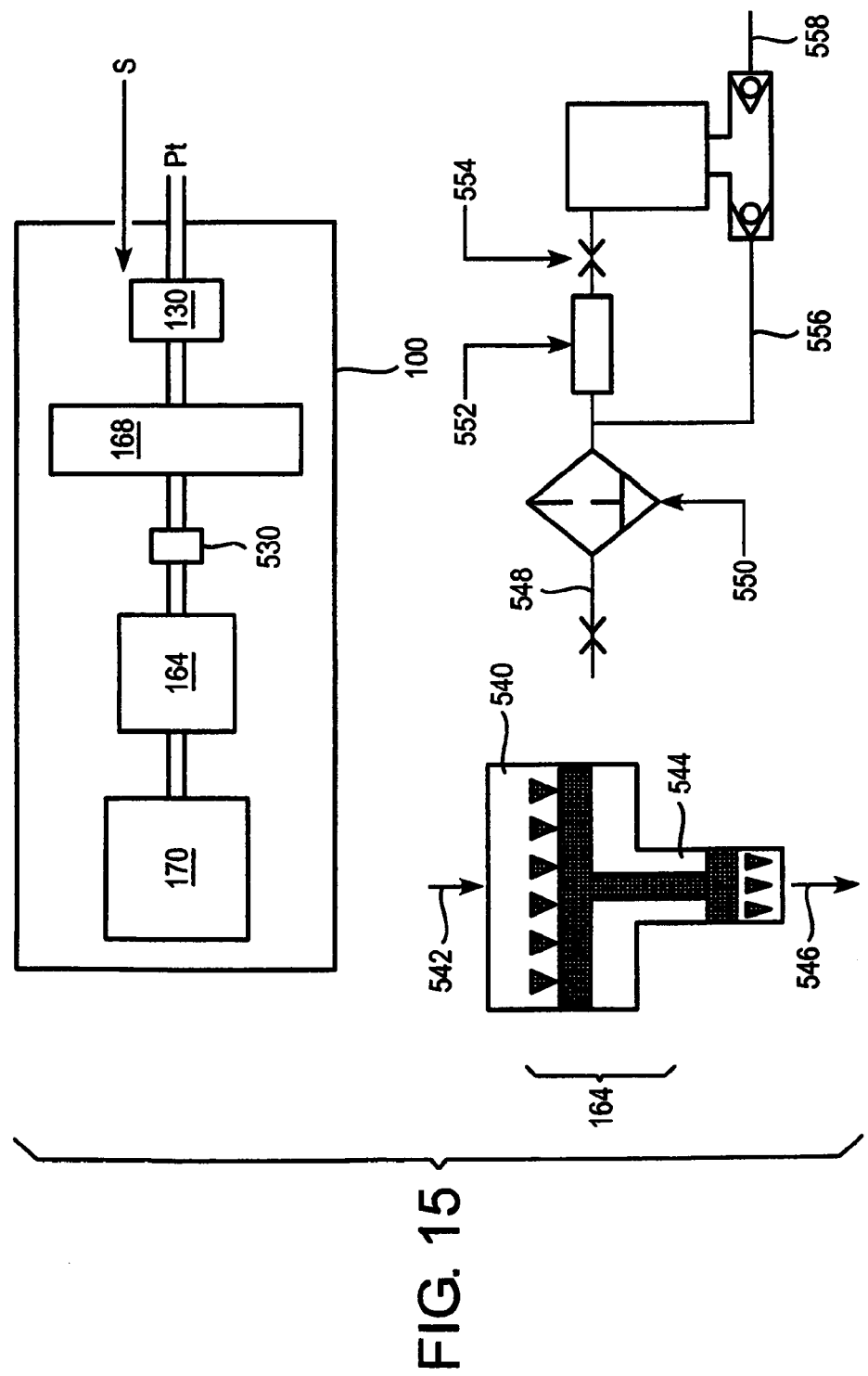
FIG. 15 describes use of a pressure amplifier to boost the pressure output of the oxygen source or ventilator.

FIG. 15: In another embodiment of the present invention a pressure amplification device is used to boost the pressure output of the system to the patient. The ventilator 100 includes a gas source 170, a pressure amplifier unit 530, a reservoir/accumulator 168, on on/off valve 130, flow to the patient Pt and an incoming breath signal S. The pressure amplifier unit includes an inlet stage 540 receiving a drive air pressure 542 and an outlet stage 544 emitting a amplified air pressure 546. Schematically the amplifier includes a gas supply 548, a filter 550, a regulator 552, a gas drive inlet 554, and a gas supply outlet 558. Incoming pressures from the gas supply can be as low as 1 psi and amplified to 10-30 psi., thus providing adequate pressure and flow to accomplish TIJV. Alternately, the output of the pressure amplifier can be stored in an accumulator which will boost the volume that can be delivered during depressurization of the accumulator during an augmentation pulse as described previously. The pressure amplifier will allow a relatively weak gas supply such as a small LOX system, an oxygen concentrator system, or a low powered electrical air pump to be used for the gas source. The pressure amplifier unit can be pneumatically powered or electro-pneumatically powered.

FIG. 16: In another embodiment of the present invention, multiple accumulators or pistons are used to store and deliver the augmentation volume. The ventilator 100 includes a gas source 170, an array of accumulators 570 and 572, with outlet valves 574 and 576 and a main outlet valve 130 to the patient Pt. The accumulators or pistons can alternate such that for example a first accumulator or piston depressurizes to the patient for a first augmentation pulse and a second accumulator or piston depressurizes to the patient in the next augmentation pulse. In this manner, each accumulator or piston has a longer re-pressurization time (twice as long compared to a system with one accumulator or piston), therefore able to deliver sufficient volume during the augmentation pulse because of starting to depressurize from a higher pressure.

This embodiment is particularly useful in fast breath rate situations for example greater than 30 breaths per minute.

Figure 17A:
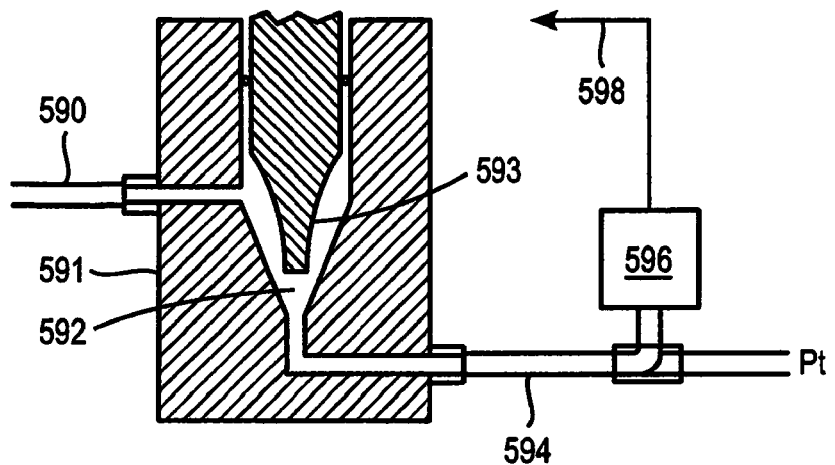
FIG. 17 describes conventional volume and timing control systems and a special timing and volume control system for delivering the ventilation therapy of the present invention in a small and low-electrically powered unit.
Figure 17B:
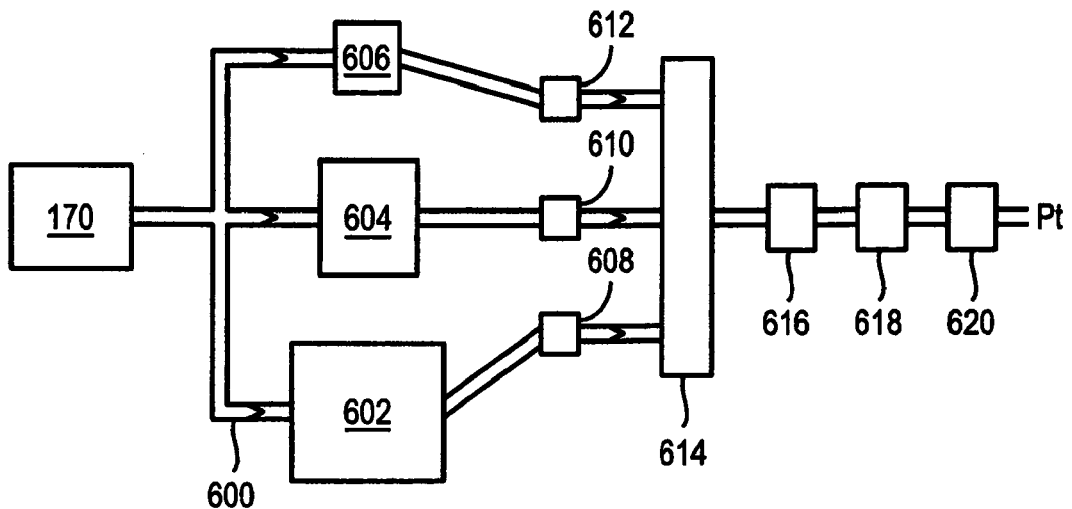

FIGS. 17*a* and 17*b*: In another embodiment of the present invention, a unique system is described to provide independent control of augmentation volume and augmentation time for delivering TIJV, but without using a pressure or volume feedback loop. FIG. 17*a* describes the conventional approach of a flow control valve with a needle, 593, a variable orifice 592, a valve body 591, a valve inlet 590 and outlet 594, a pressure or flow sensor 596 and a feedback adjustment signal 598. In the invention shown in FIG. 17*b*, an array of accumulators 602, 604 and 606 with check valves 600 and an array of orifices 616, 618, and 620 of different sizes are arranged with a valving system 608, 610, and 612 and manifold 614 such that any reasonably desired augmentation time and augmentation volume can be delivered by activating the correct combination of accumulator(s) and using the correct orifice size. This embodiment allows for independent selection of augmentation volume delivery time and augmentation volume. For example, 100ml can be delivered in 0.2 seconds or can be delivered in 0.4 seconds, depending on what is desired.

Figure 18:
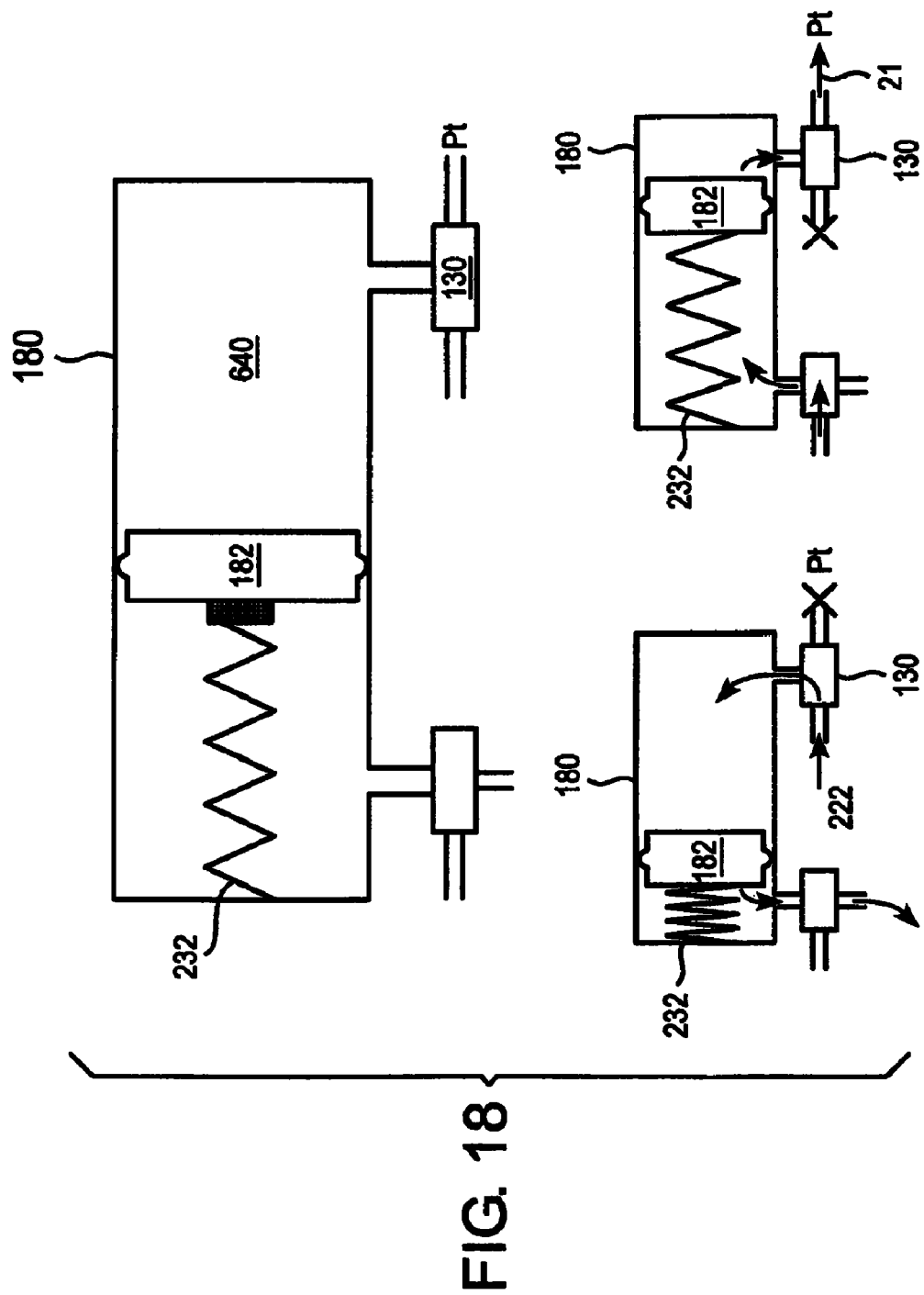
FIG. 18 describes a piston system with a spring assisted gas delivery stroke.

FIG. 18: In another embodiment of the present invention a piston with a spring is used to amplify volume delivered to the patient. The reservoir/accumulator 168 includes a cylinder 180, a moving piston 182, an outlet valve 130 to the patient PT, a pressurization and depressurization outlet chamber 640, and a spring 232. The piston strokes in one direction by the cylinder depressurizing through a valve 130 to the patient. A compressed spring 232 on the opposite side of the piston adds speed to the moving piston, thus increasing the cylinder outlet flow rate to the patient. The cylinder then re-pressurizes through the valve 130 and compresses the spring 232 and repeats the cycle for the next augmentation delivery.

Figure 19:
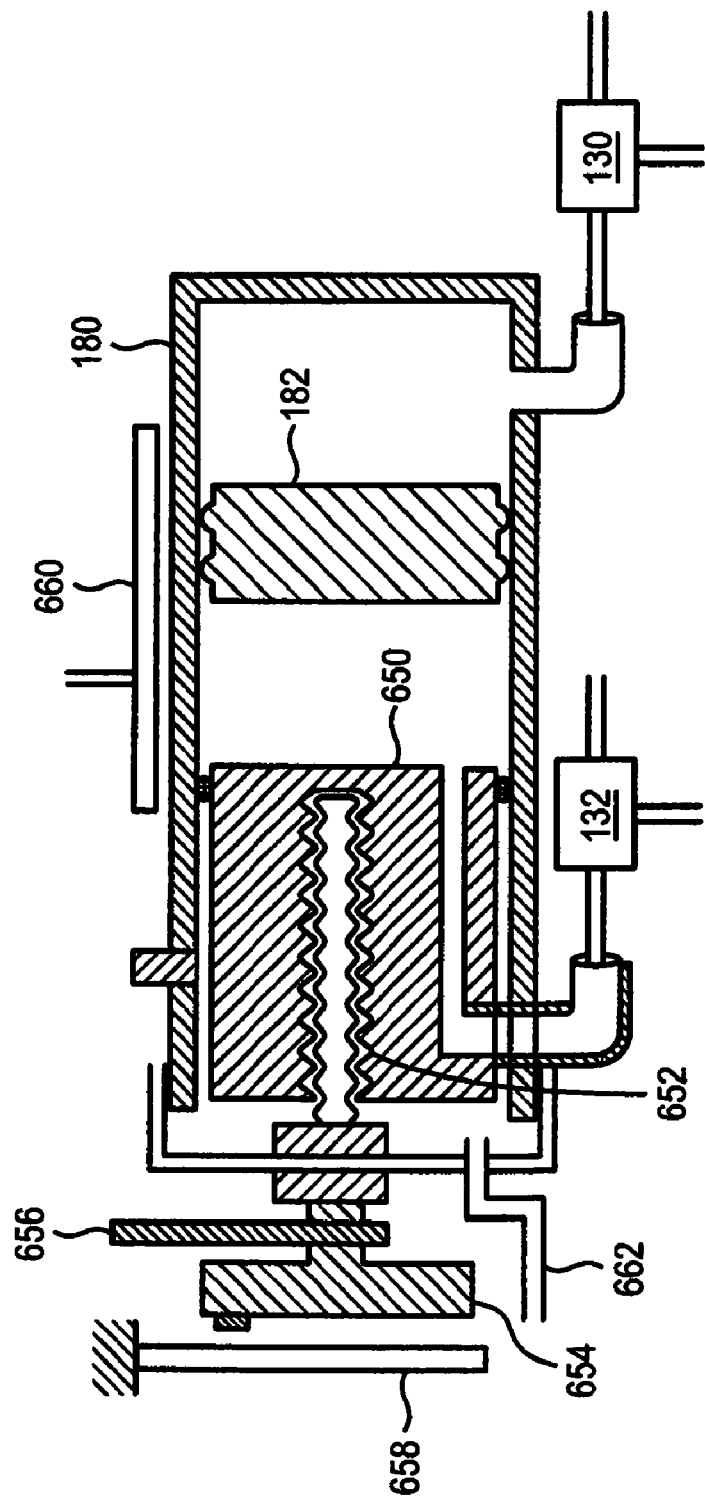
FIG. 19 describes a piston for the present invention with an adjustable volume output.

FIG. 19: In another embodiment of the present invention, an adjustable volume cylinder is used to modify volume delivery. In this embodiment shown, the piston in the cylinder stokes from side to side and each stroke sends volume to the patient while to opposite side of the chamber on the other side of the piston is re-pressurizing from the gas supply in preparation for the next stroke to the patient. The cylinder 180 includes a moveable piston 182, inlet and outlet valves on both ends of the cylinder 130 and 132, a moveable end cap 650, a thread system 652 used to move the end cap, an adjustment knob and screw 654, optionally an adjustment drive belt 656 or other drive system, optionally a knob and screw rotational position sensor 658, and optionally an end cap axial position sensor 660. The adjustment can be manual, for example by use of the knob and screw to move one end cap of the cylinder inward or outward. The changed volume will affect the volume delivered during the cylinder depressurization because of the changed capacitance of the accumulator. Alternatively, the adjustment can be electronically controlled and optionally the adjustment position can be sensed for display or control loop function by use of sensors, 660 or 658. Also, alternatively the same adjustment mechanisms can be applied to the piston embodiments described previously.

Figure 20:
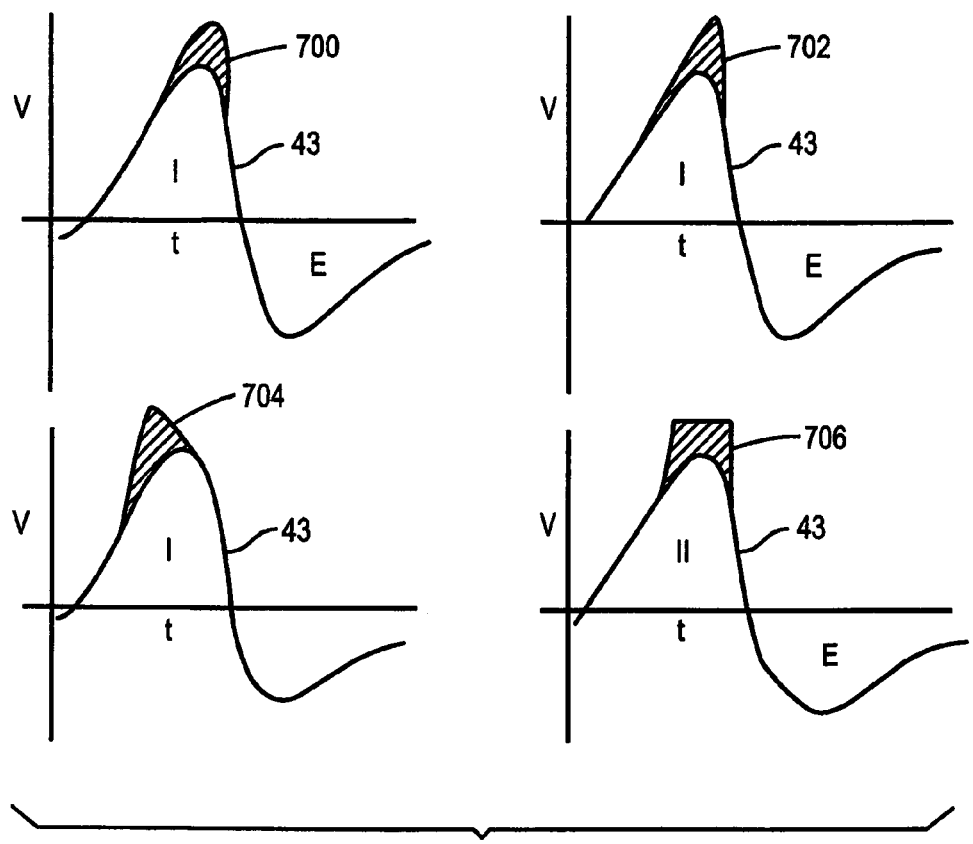
FIG. 20 describes graphically the effect of an augmentation waveform adjustment of the present invention.

FIG. 20: In another embodiment of the present invention, the augmentation pulse can be shaped in a desired waveform. This is accomplished for example by control of the piston stroke speed which can be controlled with a variable orifice on the outlet of the cylinder, or gas source pressure or stoke speed. For example as shown in the graphs the TIJV volume 50 can be a sine wave, square wave, descending wave or ascending wave.

Figure 21:
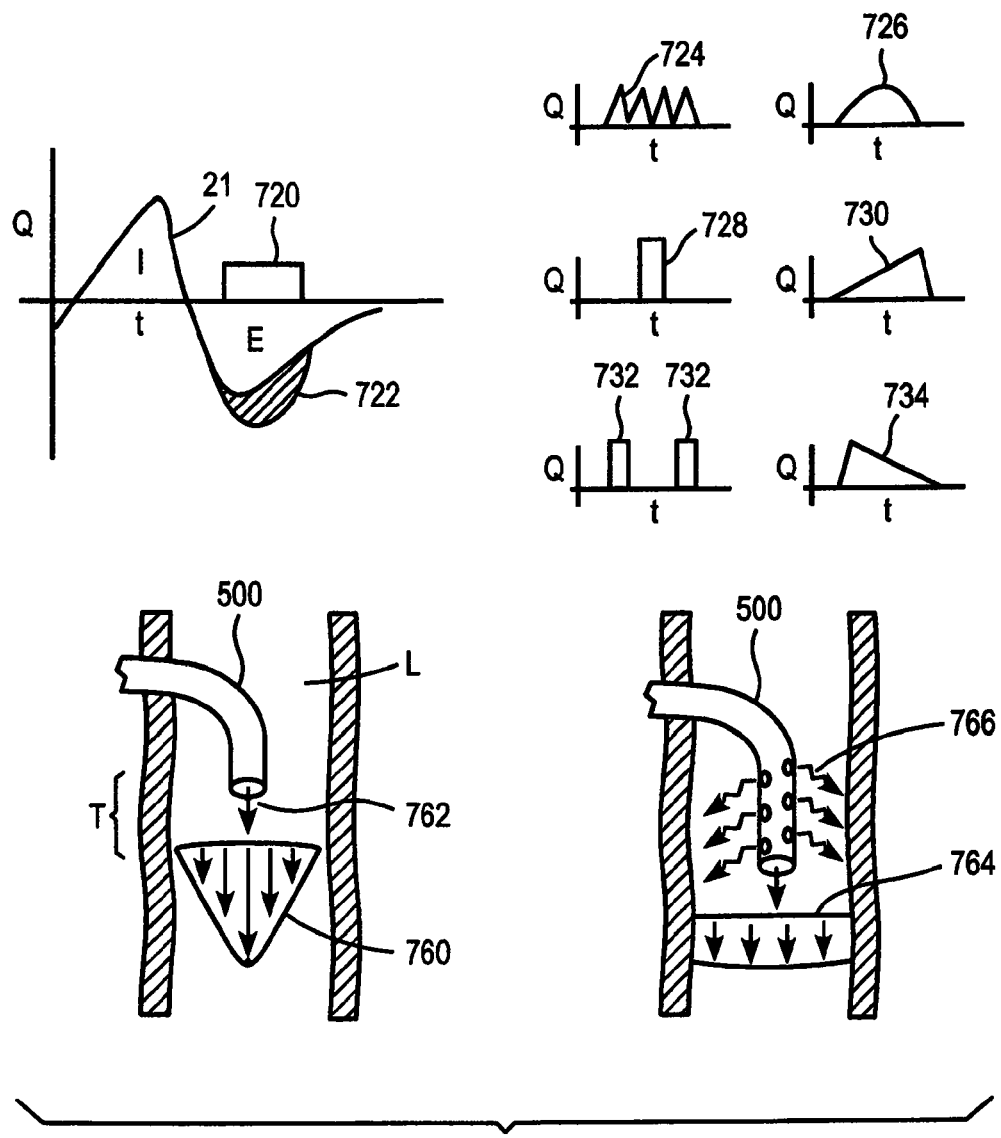
FIG. 21 describes exhalation counterflow therapy to reduce collapse of the airways during exhalation, to be used in conjunction with the augmentation therapy of present invention.

FIG. 21: In another embodiment of the present invention exhalation counter-flow is described which will have the effect of reducing collapse of the diseased, collapsible distal airways by giving those airways a back pressure. An increase in exhaled flow 722 and more volume is then able to be exhaled by the patient during exhalation. The exhalation counter-flow can be delivered in a variety of pressure or flow profiles, such as a square exhalation counter-flow flow curve 720, a short pulse 728, multiple pulses 732, ascending or descending profiles 730 and 734, oscillation 724, sign wave 726, or at the beginning or end of exhalation and at high, medium or low amplitudes. The exhalation counter-flow can be delivered by the piston described previously while the piston is stroking in the opposite direction of an augmentation stroke, or it can be delivered by a simple valve between the patient and the gas supply, or by a second cylinder or piston independent of the augmentation delivery mechanism. A catheter 500 is shown in the lumen L of the trachea T. The exhalation counterflow gas exit from the catheter can be non-diffuse 762 to cause a non-uniform velocity profile 760, or can be diffuse 766 to create a more uniform velocity profile 764. The gas exit dynamics are adjusted by the gas exit ports on the catheter, a signal port is useful for non-diffuse gas exit and several small side ports are useful for diffuse gas exit. The velocity profile is selected based on the collapsibility of the patients' airways; for example a more uniform profile is used for higher degrees of collapsibility. The counterflow amplitude can also be adjusted manually or automatically based on a physiological signal such as $CO_2$, exhaled flow, volume change.

Figure 11:
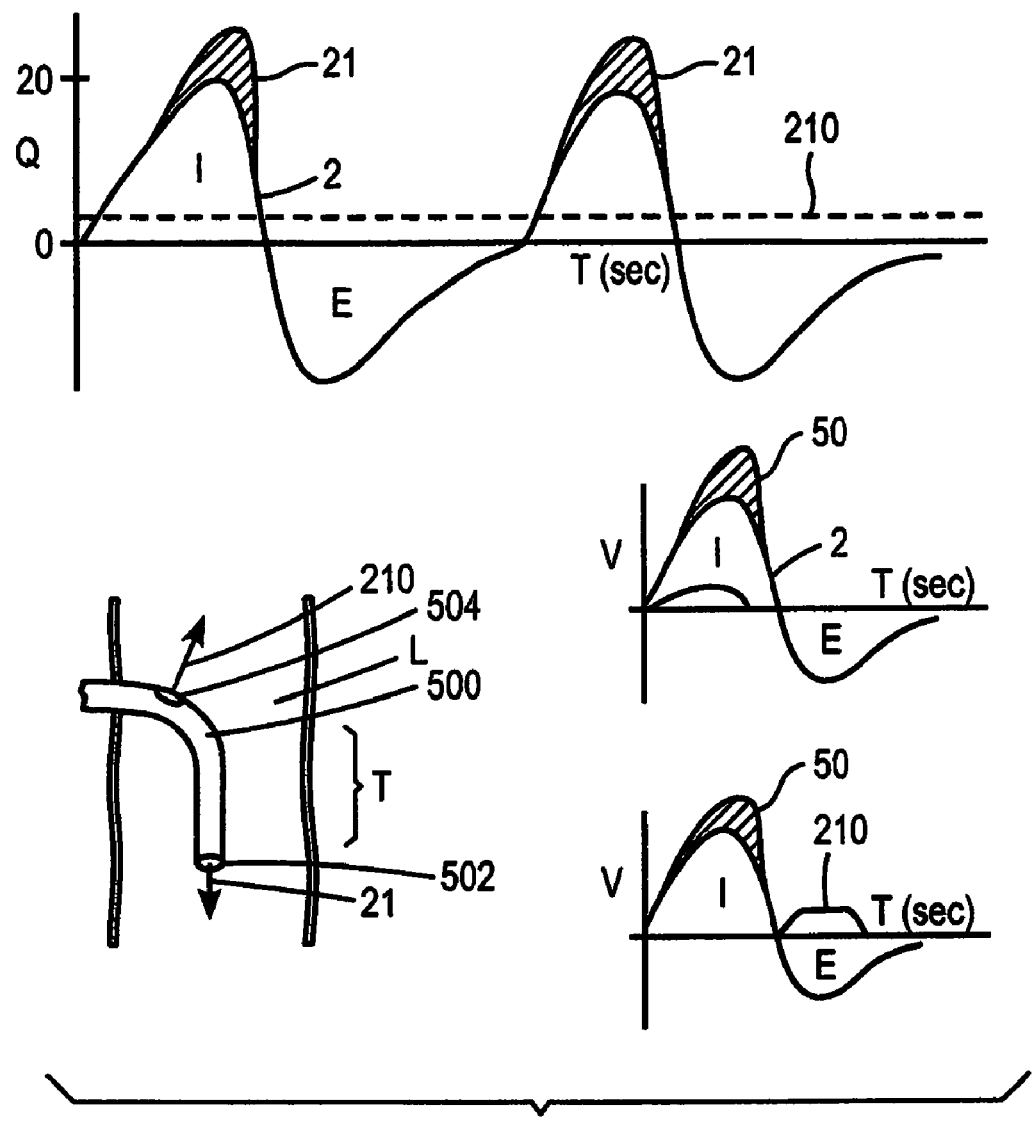
FIG. 11 describes combining oxygen insufflation of the bronchial tree with the ventilation therapy of the present invention.

FIG. 11: In another embodiment of the present invention tracheal gas insufflation flow 210 can be delivered to create a higher oxygen gas concentration in the upper airway, adjunctively to the TIJV augmentation flow 21. The catheter 50 includes an augmentation flow exit port 502 and an insufflation flow exit port 504. The insufflation can be delivered at a strategic time during the patient's inspiratory phase or can be delivered at a strategic time during the patient's expiratory phase. For example, if insufflation is delivered during the 250 msec of inspiration that precedes the augmentation pulse, then the entrained air sucked into the lung by the augmentation jet will be higher in O2 content. Or, if insufflation is delivered during exhalation it can have the effect desired plus also provide exhalation counterflow described previously. The amplitude of the insufflation flow can be adjustable, manually or automatically.

Figure 22:
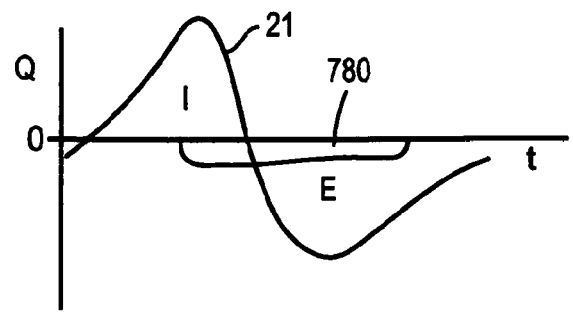
FIG. 22 describes tracheal gas evacuation to reduce the CO2 content in the airways, to be used in conjunction with the augmentation therapy of the present invention.

FIG. 22: In another embodiment of the present invention tracheal gas evacuation is used to lower the $CO_2$ content in the trachea, which will cause a lower $CO_2$ content in the distal compartments of the lung due to mixing and diffusion that will occur because of the concentration gradient. The evacuation flow 780 can be applied during inspiration, exhalation or both and the evacuation profile can be constant, oscillatory, synchronized, sinusoidal, etc., or can be applied intermittently at a rate and amplitude as determined by biofeedback such as by monitoring $CO_2$ levels in the trachea.

Figure 23:
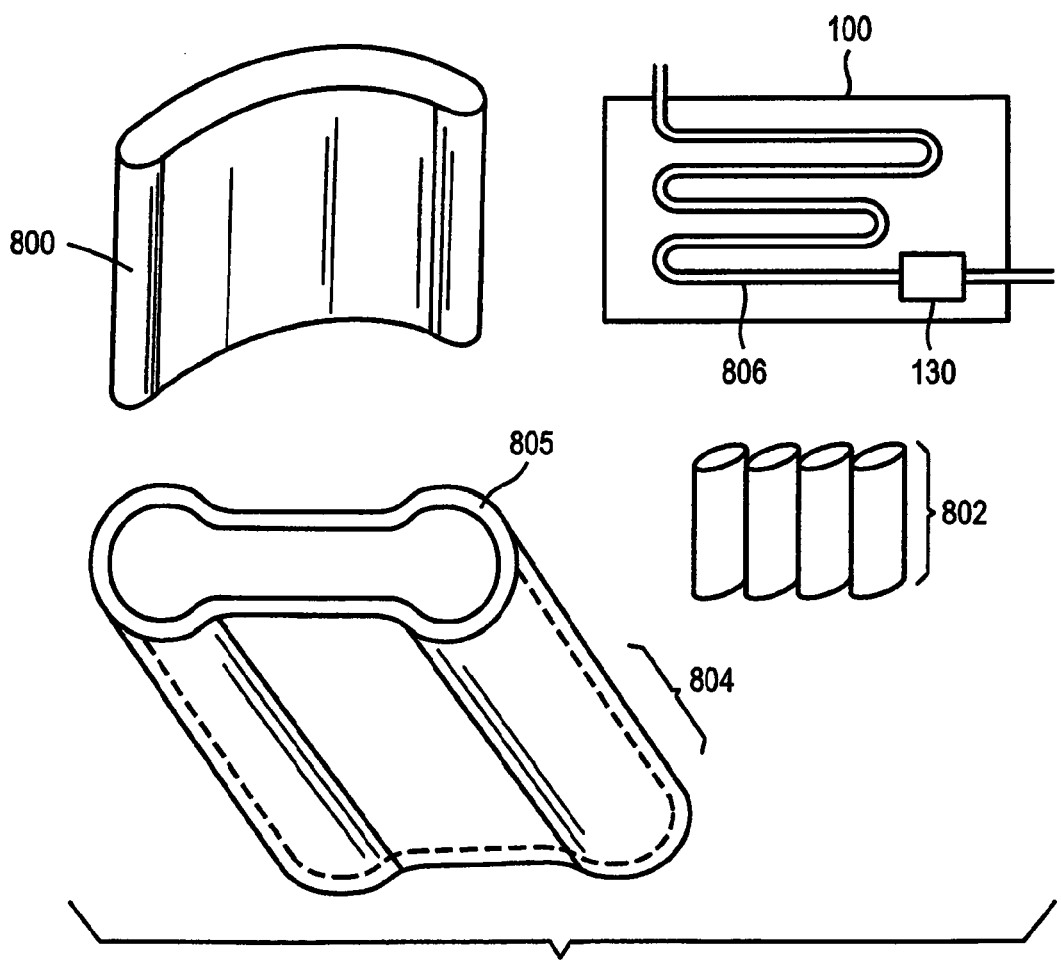
FIG. 23 describes non-cylindrically shaped oxygen gas cylinders or accumulators for use in the present invention.

FIG. 23: In another embodiment of the present invention, the ventilator can include a non-cylindrical gas accumulators or gas supply reservoir in order to optimize the overall shape of the compact ventilator, since an optimally small ventilator may not accommodate the conventional shape of a gas cylinder. For example the shape can be concave 800, or an interconnected series of cylinders 802, or a conduit system 806. Or the ventilator enclosure 804 itself can comprise the gas reservoir or gas supply by having a bilayer casing 805. In the case shown the ventilator enclosure cross section is bone-shaped, however it could be of any reasonable shape. Unorthodox shaped reservoirs are capable of handling the typical working pressure of the invention which is below 50 psi.

In another embodiment of the present invention, the ventilator is electrically powered by a manual hand-cranked charging generator unit, either internal to the ventilator or externally connected to the ventilator, (not shown).

In another embodiment of the present invention the ventilator can receive gas flow and pressure by a manual pneumatic pump system actuated by the user, (not shown).

In other embodiments of the present invention shown in FIGS. 24-33, catheter designs are described which will space the catheter tip in the center of the trachea, so that the tip is not poking, irritating or traumatizing the wall of the trachea, a problem described with other transtracheal catheters. Also, stabilizing the catheter tip in the center of the tracheal lumen so that the tip does not whip during the jet pulse is important. Whipping, a problem with other catheters, can cause tracheal wall trauma. Further, the tip should be directed generally in the direction of the carina C and not towards a tracheal wall W, in order for the augmentation pulse to effectively reach the lower portions of the left lung LL and right lung RL.

FIG. 24: In one embodiment of the invention, a looped catheter with approximately a 360 degree curve 809, is described which is inserted through a stomal sleeve 808 and contacts the anterior wall AW, spaces it from the posterior wall PW, and spaces the catheter gas exit port 811 in the center of the tracheal lumen L. The catheter lumen beyond the exit port is occluded so the gas can exit out of a the port 811, or the loop can extend so that the catheter tip points downward toward the carina. The catheter loop is biased so that the anterior section of the loop is always touching the anterior tracheal wall thus assuring that the catheter exit port will be somewhere in the middle of the tracheal lumen. Alternatively as shown in FIG. 25, the catheter can comprise approximately a 450-540 degree loop 810 so that the distal tip is directed down toward the carina. In this embodiment it may be more advantageous for the catheter bend to be biased such that there is contract with either or both of the anterior and posterior tracheal wall. This embodiment will also apply a gentle tension on the tracheal wall to help keep it in position, however when the trachea collapses with coughing, the curved catheter will compress with the trachea.

FIG. 26: In another embodiment of the invention a dual cannula design is described with an ostomy or stomal sleeve 808. The outer guiding cannula 820 removably attaches to the sleeve so that the guiding cannula can be removed and reinserted conveniently. The guiding cannula is especially thin wall, for example 0.010"-0.030" and is typically made of a braid or coil reinforced elastomer or thermoplastic to resist kinking. The guiding cannula, although semi-rigid, is short compared to the front-to-back width of the trachea and therefore is atraumatic. The inner cannula is the TIJV catheter and is dimensioned to fit the ID of the guiding cannula snuggly. The tip of the TIJV catheter extends beyond the tip of the guiding cannula. The guiding cannula semi-rigidity provides a predetermined known track for the TIJV catheter to follow and therefore positions the TIJV catheter tip somewhere in the tracheal lumen and not touching the tracheal wall.

FIG. 27: In another embodiment of the invention a shaped catheter design is described which is intended to remain close to the anterior wall of the trachea, thus when the patient's trachea collapses during coughing or bronchospasm, the posterior wall is not irritated. Near the tip of the catheter the catheter makes a gentle anterior bend 842 and posterior bend 843 such that the tip is directed away from the tracheal anterior wall. The stomal sleeve inner flange 922 provides a spacing of the catheter away from the anterior wall in that location. The catheter includes an flange 844 that can be adjustable. Alternatively the catheter tip can include an atraumatic spacer that pushes it away from the anterior tracheal wall.

FIG. 28: In another embodiment of the invention a catheter design is described which is comprised of extremely soft material, for example 30-60 shore A so that it does not irritate the tracheal wall when it comes in contact with it. The shape of the soft highly flexible catheter is maintained by a rigid filament stiffening member 830 imbedded into the catheter construction, for example a thin stainless steel, thermoplastic or shape memory wire shaped-set into the required and desired shape.

Figure 29:
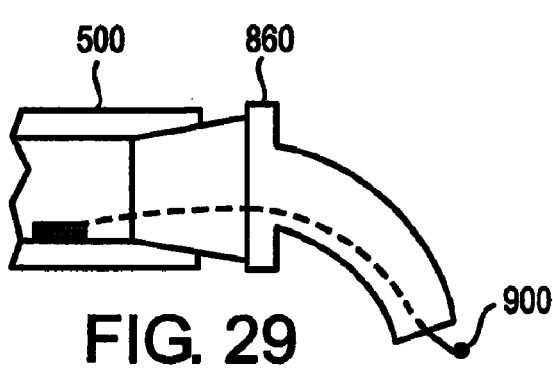
FIG. 29 describes a ventilation catheter adaptable to a standard respiratory connector.

FIG. 29: In another embodiment a catheter is described which is connected to the male connector of a standard tracheal tube such as a short tracheostomy tube 860 or a laryngectomy tube and which includes a protruding or extending sensor 900 which extends through the length of the tracheal tube and into the tracheal airway where the sensor can sense airflow.

Figure 30:
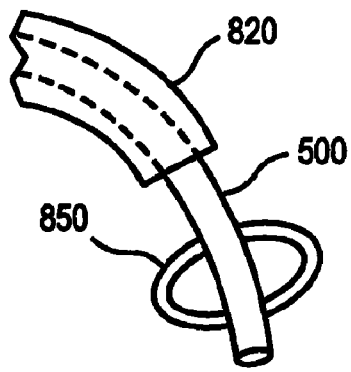
FIG. 30 describes a ventilation catheter and a catheter guide, where the catheter has a non-obstructing positioning member.

FIG. 30: In another embodiment of the invention a catheter design is described that has an anchoring basket 850 to center the catheter in the tracheal lumen. The basket is highly forgiving such that partial or full collapse of the tracheal diameter (during coughing or spasms) is not impeded by the basket and any contract is atraumatic. The basket material must be lubricious and rounded so that it does not encourage granulation tissue growth and become attached to the tracheal wall. The basket is typically releasable from a sleeve for easy insertion and removal but can also be easily inserted and removed through the ostomy due to its compliant nature. Alternatively, the basket can be an inflatable fenestrated cuff.

Figure 31:
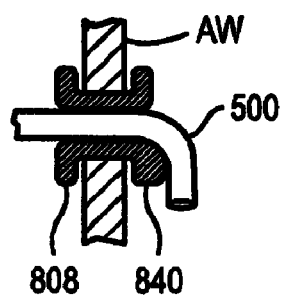
FIG. 31 describes a ventilation catheter with a spacer positioned to locate the catheter tip at a controlled desired distance from the anterior tracheal wall.

FIG. 31: In another embodiment of the invention a catheter design is described which includes a spacer 840 that spaces it from the anterior wall of the trachea. The spacer can be a soft material or a shape memory foam encapsulated in a highly compliant membrane. Or, the spacer can be an inflatable cuff. The cuff can be a normally deflated cuff that requires inflation by the user, or can be a normally inflated and self inflating cuff which requires deflation for insertion and removal. The spacer can be a protrusion of the stomal sleeve 808 or the catheter 50.

Figure 32:
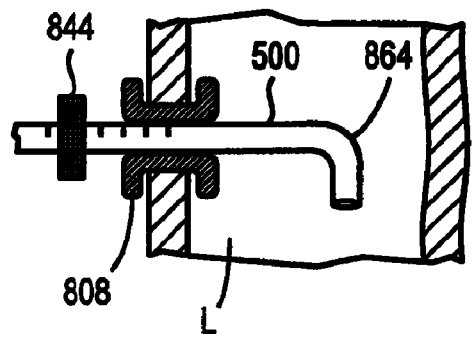
FIG. 32 describes a ventilation catheter with a generally right angle curve to position the tip of the catheter in the center of the tracheal lumen.

FIG. 32: In another embodiment of the invention a shaped catheter design is described which is intended to distend in the tracheal lumen minimally, by being shaped in a right angle or approximately a right angle 864. This shape allows the tip of the catheter to be directed downward toward the carina, but with a very short catheter length. This shape may be advantageous when the trachea is moving and elongating since the body of the catheter will not be contacting the tracheal walls, unless the trachea is collapsed. The catheter also includes an adjustable flange 860 to set the required depth of insertion of the catheter.

Figure 33:
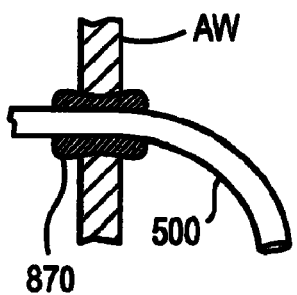
FIG. 33 describes a ventilation catheter with a compressible stomal tract seal.

FIG. 33: In another embodiment a catheter is described comprising a compliant and/or inflatable sealing sleeve 870 for sealing and securing the catheter shaft transcutaneously to the ostomy site. The sleeve can be a self deflating or inflating or a manually deflating or inflating design, for example a memory foam encapsulated by a compliant elastomeric membrane with a deflation bleed port.

Figure 34:
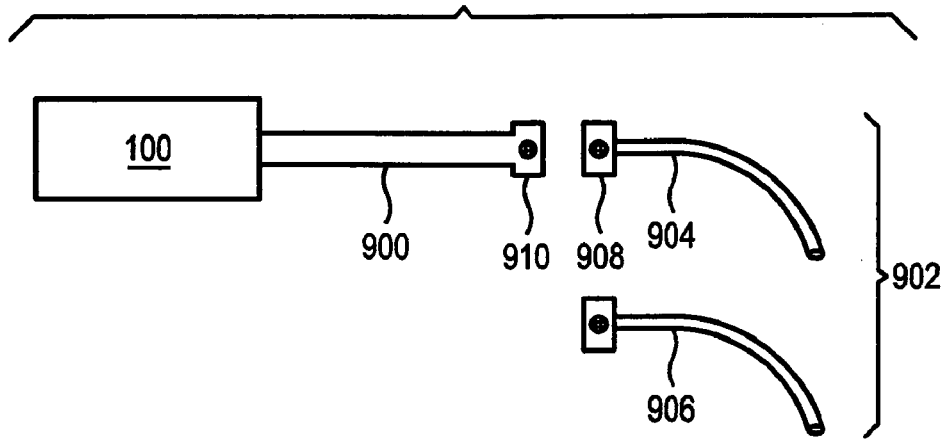
FIG. 34 describes a smart ventilation catheter with electronic tags to handshake with the ventilator.

FIG. 34: In another embodiment a smart catheter is described in which there is a proximal external catheter section 900 and distal internal catheter section 902 which connect to each other. Each section contains a miniature device that produces an electrical signature wherein the distal section signature tag 908 is recognized by the proximal section recognition tag 910. In this manner, different catheter designs for different therapeutic modes can be attached to the ventilator unit, and the ventilator unit will detect which catheter and therefore which mode should be used. For example, a non-jet catheter 904 can be attached and the ventilator can switch to non-jet mode, and a jet catheter 906 can be attached and the ventilator switches to a jet mode. Or the electrical signature can track usage time and alert the user when the catheter needs to be replaced or cleaned. Or the signature can be patient specific or distinguish between adults and pediatric patients, or to report on therapy compliance.

Figure 35:
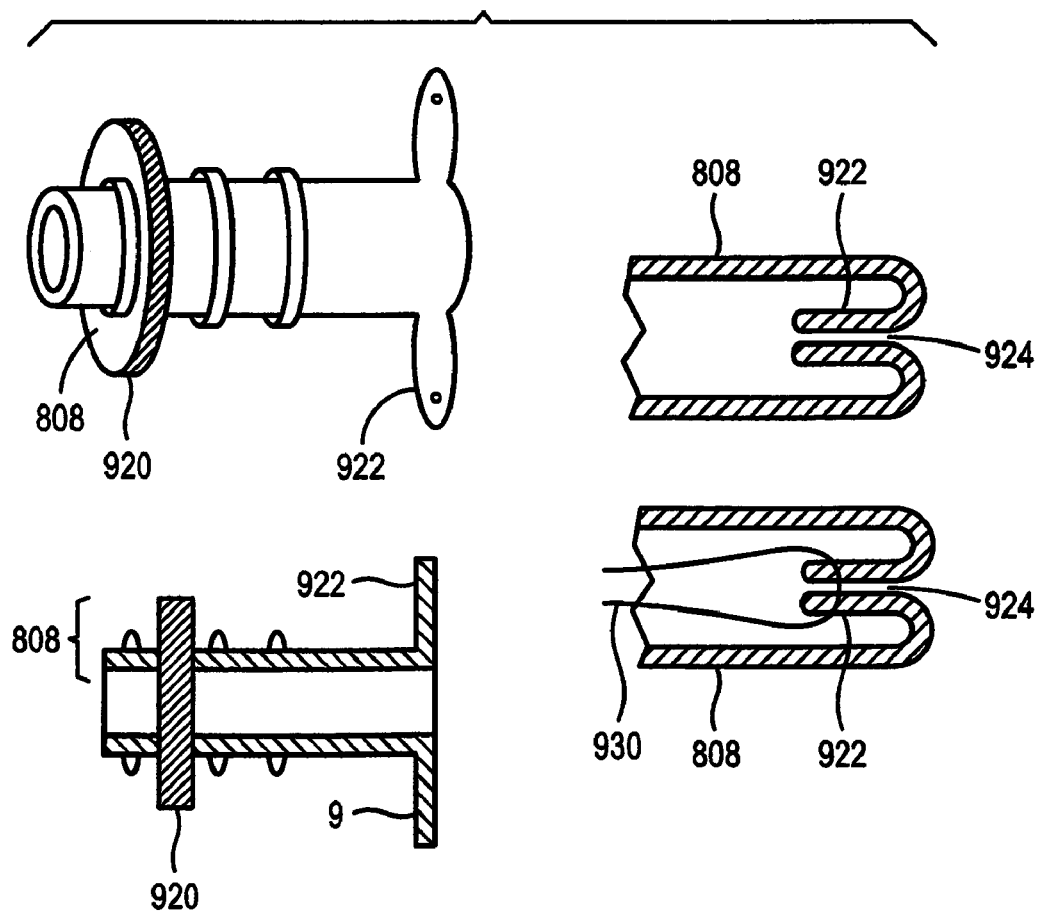
FIG. 35 describes an ostomy or stomal tract guide with deployable inner retaining flanges.

FIG. 35: In another embodiment a transtracheal catheter sleeve 808 is described for placement in the trachea transcutaneous ostomy site. The sleeve comprises a proximal flange 920 and a distal flange 922 for the purpose of positioning the distal end of the sleeve just barely inside the tracheal lumen and preventing inadvertent decannulation of the sleeve. The distal flange is retractable into the main lumen of the sleeve so that when the sleeve is being inserted into the ostomy the retracted flange 924 is not protruding and the sleeve can assume a low profile for easy and atraumatic insertion. Then, when inserted into the trachea, the flange can be deployed by pushing a trocar against the retracted flange or by releasing a release cord 930 which was keeping the flange in the retracted state.

Figure 36:
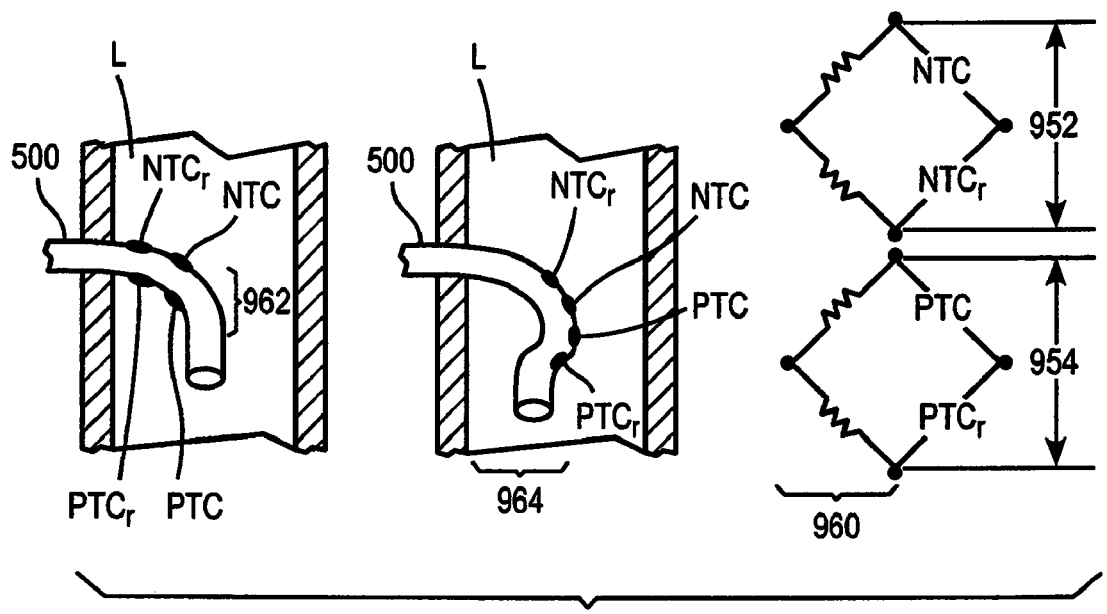
FIG. 36 describes a ventilation catheter with two breath sensor arrays which use both negative and positive coefficient thermistors, useful in distinguishing between inspiration and exhalation in a variety of temperature conditions.

FIG. 36: A sensor arrangement is described which combines negative thermal coefficient NTC and positive thermal coefficient PTC thermistors to detect cooling and heating for the purpose of determining breath flow directionality. The NTC thermistor is especially effective in detecting inspiration; as the thermistor is cooled by the cooler inspired air, the start of inspiration is detected. The PTC thermistor is especially effective in detecting exhalation; as the thermistor is heated by the warmer exhaled air the start of exhalation is detected. An external reference thermistor is used to measure ambient temperature. If the ambient temperature is cooler than body temperature which will normally be the case, the arrangement described is used, however if ambient temperature is warmer than body temperature, then the operation of the NTC and PTC thermistors is reversed. Each thermistor is paired with a reference thermistor NTCr and PTCr and the signals from each pair of sensing thermistor and its reference thermistor are processed through an electronic comparator, such as a wheatstone bridge 960 with resistors R to complete the bridge, to yield a dampened output signal 952 and 954 that dampens artifacts in the respiratory pattern and drifts that occur because of surrounding conditions. Alternatively, the thermistor sensors can be heated by applying a voltage to them such that their resting temperature and resistance is kept at a known constant value. Therefore, heating and cooling from inspiration and exhalation is highly predicable when ambient temperature is known. For example, the thermistors can be warmed to a temperature of 120 degrees F. Exhalation cools the thermistor less than inspiration and therefore the breath phase can be determined. The thermistors can be arranged on the catheter such that the positive coefficient thermistors are located on the side of the catheter facing exhaled flow, and the negative coefficient thermistors are located on the side of the catheter facing inspired flow, 962. Or alternatively, the thermistors can be spacially arranged in some other strategic orientation such as placing the sensing thermistors such that they are fully exposed to airflow and the reference thermistors such that they less exposed to airflow 964.

In another aspect of the present invention, sensors are included to provide biofeedback for a variety of purposes. For example, the presence of coughing or wheezing or dyspnea is monitored by comparing the measured breathing curve to algorithms in the software. If an exacerbation is detected, a medicant can be delivered, such as a bronchodilator. Or, tracheal humidity can be monitored for the purpose of increasing or decreasing the delivered volume so that the lung does not become dry, or alternatively the jet venturi can be increased or decreased to increase or decrease upper airway entrainment, in order to maintain the correct lung humidity or correct ventilation volume. Or, patient activity level can be monitored with an actigraphy sensor and the ventilation parameters can be adjusted accordingly to match the activity level of the patient. Or the patient's venous oxygen saturation can be measured in the percutaneous ostomy by a pulse oxymetry sensor placed in the ostomy sleeve or in the catheter and the ventilation parameters adjusted accordingly. Or the patient's tracheal CO2 level can be measured with a CO2 sensor and the ventilation parameters adjusted accordingly. All these prospective measured parameters can be transmitted by telemetry or by internet to a clinician for external remote monitoring of the patient's status.

Figure 37:
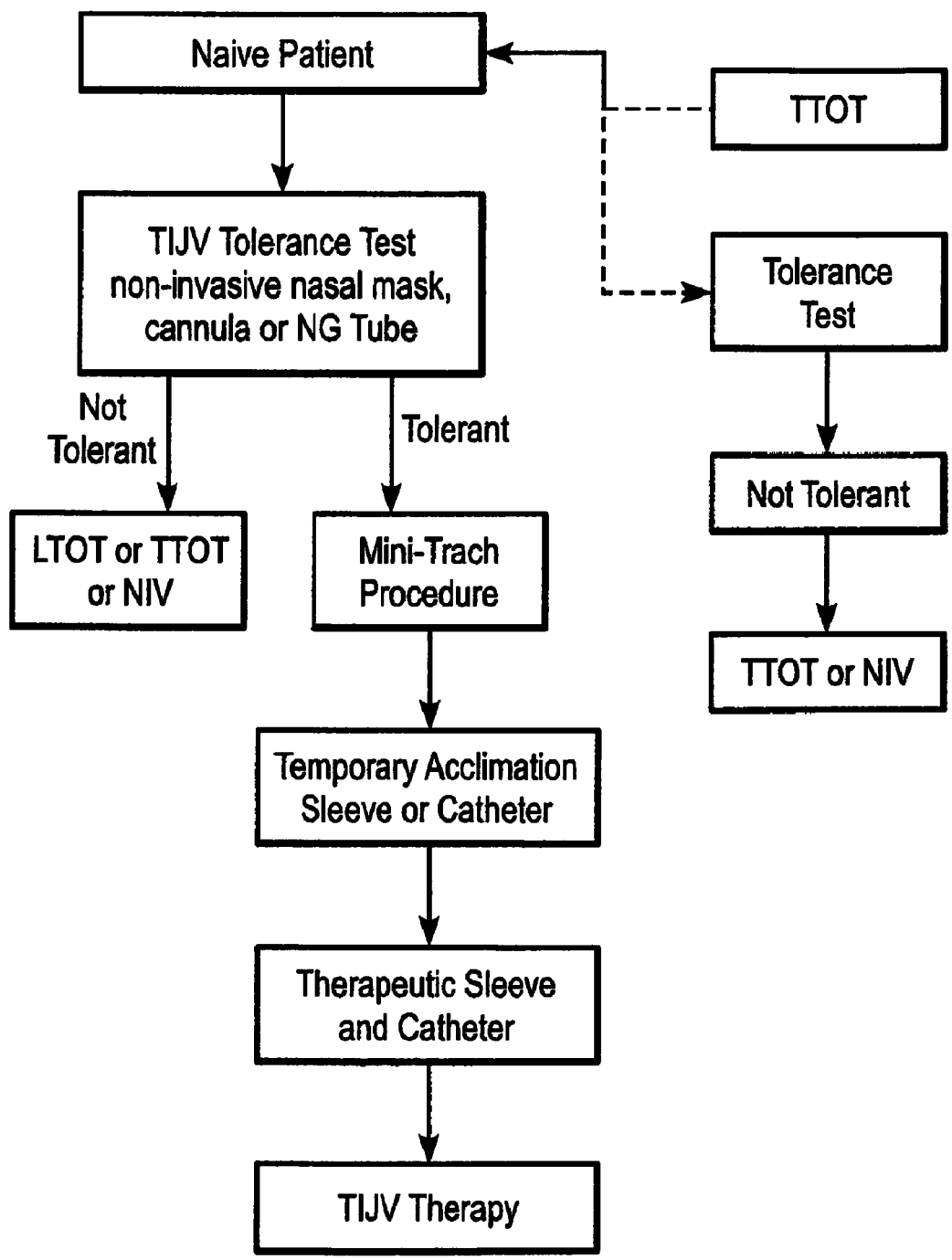
FIG. 37 describes a screening and tolerance test algorithm and method for the purpose of evaluating a patient for the therapy of the subject invention.

FIG. 37: Another potential problem of new minimally invasive ventilation and oxygen therapy modalities is the patient acceptance and tolerance to the new therapy, and the acclimation of the body to the intervention such as a minitracheotomy. For example patients may not want to have an intervention performed unless they can experience what the effect of the therapy will be. Or for example, the body may be initially irritated by the intervention, and if the therapy is started immediately after the intervention, the benefit may be spoiled by other physiological reactions. Therefore in another aspect of the present invention a novel medical procedural sequence is described, to allow the patient to experience the therapy and to acclimate the patient to the intervention before the therapy is started. The patient is subjected to a tolerance test by using a non-invasive patient interface such as a mask or nasal gastric tube or a laryngeal mask or oropharyngeal airway (NGT, LMA or OPA). In the case of using the NGT the patient's nasal cavity can be anesthetized to allow the patient to tolerate the NGT easily. TIJV is then applied to the patient in this manner for an acute period of time to determine how well the patient tolerates the therapy. Also, information can be extracted from the tolerance test to extrapolate what the therapeutic ventilation parameters should be for that patient. After the tolerance test, a mini-otomy procedure is performed and an acclimation sleeve and/or acclimation catheter is introduced into the airway. After a subchronic acclimation period with the temporary sleeve/catheter, for example one week, the therapeutic catheter and/or ostomy sleeve is inserted into the patient and the therapy is commenced, or alternatively another brief acclimation period will take place before commencing the ventilation therapy. If the patient was a previous tracheotomy patient, for example having been weaned from mechanical ventilation, then the tolerance test can be applied directly to the trachea through the tracheotomy. If the patient was a previous TTOT patient, for example with a 3 mm transtracheal catheter, in the event the mature ostomy tract is too small for the TIJV catheter, then the tolerance test can be administered from the nasal mask, NGT, LMA or OPA as described previously, or alternatively the tolerance test is performed using a smaller than normal TIJV catheter that can fit in the existing ostomy. Or alternatively the tolerance test is delivered directly through the ostomy pre-existing from the transtracheal catheter using the same or similar transtracheal catheter, or a transtracheal catheter with the required sensors. Then if needed, a larger acclimation catheter and or sleeve is placed in the ostomy to dilate it and after the correct acclimation period the therapy is commenced.

Figure 38:
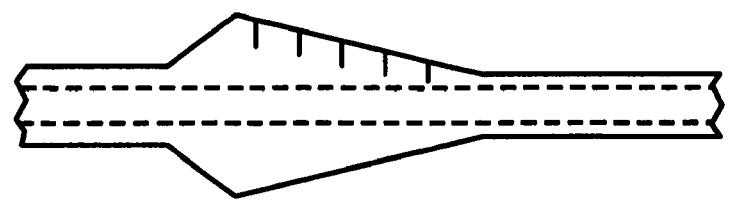
FIG. 38 describes a special catheter with a stepped or tapered dilation section.

FIG. 38: In another embodiment of the present invention a special catheter 990 is described with a stepped or tapered dilatation section 991. The catheter 990 can be used to dilate the otomy to the appropriate amount during an acclimation period or during the therapeutic period by inserting to the appropriate depth, or can be used to successively dilate the otomy to larger and larger diameters. The catheter tapered section 991 can be fixed or inflatable. Length and diameter markings 992 are provided so that the proper diameter is used.

Figure 39:
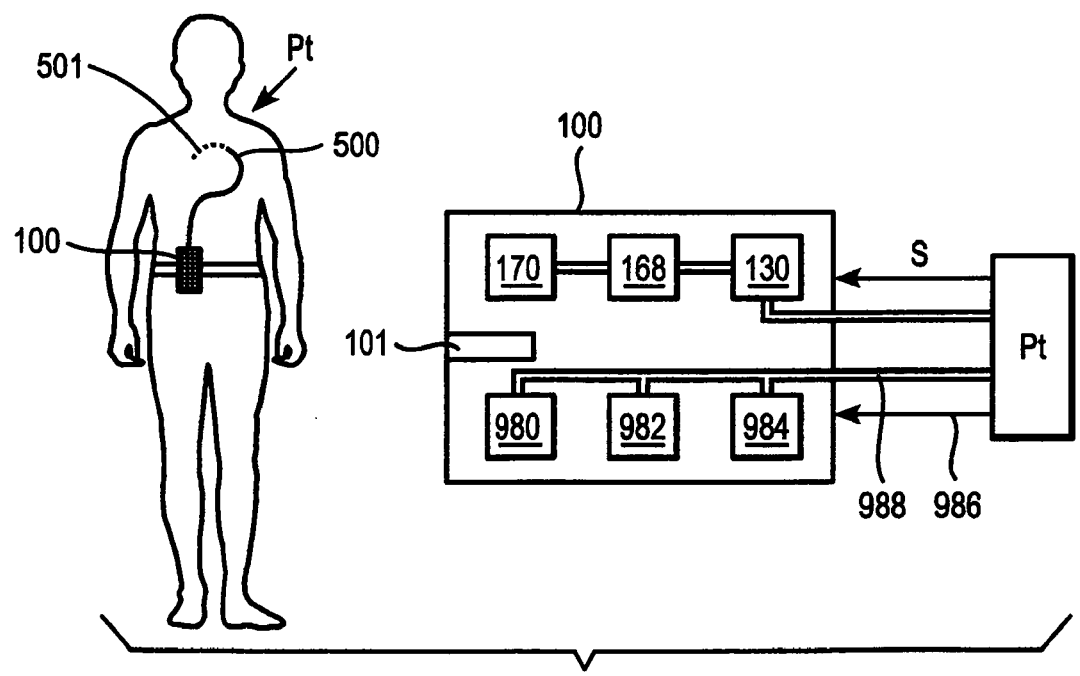
FIG. 39 describes the overall invention.

FIG. 39 describes the overall invention, showing a wearable ventilator 100 being worn by a patient Pt, which includes an integral gas supply 170, battery 101, volume reservoir/accumulator 168, on/off outlet valve 130, transtracheal catheter 500, a tracheal airflow breath sensor 101 and signal S, as well as an optional exhalation counterflow unit 980, gas evacuation unit 982 and medicant delivery unit 984 and respective flow output or input 988, and a biofeedback signal 986.

It should be noted that the different embodiments described above can be combined in a variety of ways to deliver a unique therapy to a patient and while the invention has been described in detail with reference to the preferred embodiments thereof, it will be apparent to one skilled in the art that various changes and combinations can be made without departing for the present invention. Also, while the invention has been described as a means for mobile respiratory support for a patient, it can be appreciated that still within the scope of this invention, the embodiments can be appropriately scaled such that the therapy can provide higher levels of support for more seriously impaired and perhaps non-ambulatory patients or can provide complete or almost complete ventilatory support for non-breathing or critically compromised patients, or can provide support in an emergency, field or transport situation. Also, while the invention has been described as being administered via a transtracheal catheter it should be noted that the ventilation parameters can be administered with a variety of other airway interface devices such as ET tubes, Tracheostomy tubes, laryngectomy tubes, cricothyrotomy tubes, endobronchial catheters, laryngeal mask airways, oropharyngeal airways, nasal masks, nasal cannula, nasal-gastric tubes, full face masks, etc. And while the ventilation parameters disclosed in the embodiments have been specified to be compatible with adult respiratory augmentation, it should be noted that with the proper scaling the therapy can be applied to pediatric and neonatal patients.

What is claimed is:

1. A ventilatory support apparatus, comprising:
   (a) a ventilator;
   (b) a tubing adapted to be in communication with a patient's airway;
   (c) a breath sensor adapted to measure spontaneous airflow of the patient's airway; and
   (d) a delivery mechanism for delivering a volume of ventilation gas at a rate synchronized with the patient's spontaneous breathing and delivered during the patient's inspiratory phase.

2. The apparatus of claim 1, wherein the ventilator is configured to be worn by the patient.

3. The apparatus of claim 1, wherein the ventilator includes an integrated supply of oxygen volume.

4. The apparatus of claim 1, wherein the ventilator includes an integrated oxygen generating system.

5. The apparatus of claim 1, wherein the ventilation gas volume to be delivered is 5-50% of a patient's natural tidal volume.

6. The apparatus of claim 1, wherein a ventilation gas driving pressure is 5-25 psi.

7. The apparatus of claim 1, wherein a ventilation peak flow rate delivery is 12-50 liters per minute.

8. The apparatus of claim 1, wherein a ventilation gas delivery time is 0.1 to 0.8 seconds.

9. The apparatus of claim 1, wherein the tubing includes a tip and a ventilation gas exit speed out of the tip is 25-400 meters per second.

10. The apparatus of claim 1, wherein ventilation gas exit airflow dynamics are selected to cause 25-200% volume entrainment of gas from an upper airway into a lung with the ventilation gas.

11. The apparatus of claim 1, wherein a ventilation gas delivery amplitude is selected to cause a less negative pressure in a patient's lung during inspiration compared to a negative pressure during un-assisted breathing.

12. The apparatus of claim 1, wherein a ventilation gas delivery amplitude is selected to cause a positive pressure in a patient's lung during inspiration compared to a negative pressure during un-assisted breathing.

13. The apparatus of claim 1, wherein the breath sensor comprises two individual sensors used to obtain a comparison between the two individual sensors wherein a comparison is used to compensate for drifts and signal artifacts.

14. The apparatus of claim 13, wherein the individual sensor comparison is differentiated to correlate the signal to different parts of the breathing curve.

15. The apparatus of claim 1, further comprising a ventilation gas source.

16. The apparatus of claim 15, wherein the ventilation gas source is a liquid oxygen system.

17. The apparatus of claim 15, wherein the ventilation gas source is a compressed oxygen gas source.

18. The apparatus of claim 15, wherein the ventilation gas source is an oxygen generating system.

19. The apparatus of claim 1, wherein the sensor comprises means to measure the strength and direction of airflow to deliver the ventilation gas after the inspiratory flow rate reaches a peak amplitude.

20. The apparatus of claim 1, wherein the sensor signal is correlated to respiratory muscle activity to provide means to deliver the ventilation gas after respiratory muscles reach their maximum work.

21. The apparatus of claim 1, wherein the delivery mechanism delivers gas after respiratory muscles reach their maximum work.

22. The apparatus of claim 1, wherein the delivery mechanism delivers gas in multiple pulses during inspiration.

23. The apparatus of claim 1, comprising means for adjusting the ventilation gas delivery to occur at any time within the inspiratory phase, depending on the comfort and ventilatory needs of the patient, wherein a time in the inspiratory phase is determined by information from the breath sensor.

24. The apparatus of claim 23, wherein the adjustment means is capable of adjusting the ventilation gas delivery automatically by a physiological feedback mechanism.

25. The apparatus of claim 24, wherein the feedback mechanism is based on airway gas concentrations.

26. The apparatus of claim 24, wherein the feedback mechanism is based on depth of breathing.

27. The apparatus of claim 24, wherein the feedback mechanism is based on rate of breathing.

28. The apparatus of claim 24, wherein the feedback mechanism is based on pulse oximetry.

29. The apparatus of claim 23, wherein the adjustment means is capable of being made manually by the user.

30. The apparatus of claim 23, wherein the adjustment means is capable of being adjusted by a patient.

31. The apparatus of claim 23, wherein the adjustment means is capable of being adjusted by the clinician.

32. The apparatus of claim 1, wherein the ventilation gas delivery means is a primary ventilation gas delivery means and the apparatus further comprises means for delivering a secondary ventilation gas, the secondary gas delivery means comprising a lower gas flow rate compared to the primary ventilation gas delivery.

33. The apparatus of claim 32, comprising means to deliver the secondary ventilation gas early in inspiration.

34. The apparatus of claim 32, comprising means to deliver the secondary ventilation gas throughout inspiration.

35. The apparatus of claim 32, comprising means to deliver the secondary ventilation gas during exhalation.

36. The apparatus of claim 32, wherein the secondary ventilation gas displaces $CO_2$ in the upper airway, such that the primary ventilation gas when delivered entrains air from the upper airway into the lower airways, wherein the entrained air is low in $CO_2$, at least 2% lower in $CO_2$ compared to when the secondary ventilation gas is turned off.

37. The apparatus of claim 32, wherein the secondary ventilation gas comprises a high oxygen concentration, such as 50%-100% and the primary ventilation gas comprises a lower oxygen concentration, such as 21%-60%.

38. The apparatus of claim 32, comprising means to adjust one of a pressure and a flow rate amplitude of the ventilation gas delivery.

39. The apparatus of claim 1, comprising means to adjust the shape of the ventilation gas delivery pressure or flow rate waveform into a desired waveform, including at least one of a sine wave, an ascending wave, a descending wave or a square wave, wherein the adjusting means comprises at least one of a valve, an orifice, a piston and a regulator.

40. The apparatus of claim 1, wherein the ventilation gas delivery comprises a primary ventilation gas delivery and the apparatus further comprises means to delivery gas into an airway during exhalation to provide a counter-resistance to exhaled flow, wherein the counter-resistance gas flow dynamics are selected to reduce airway collapse.

41. The apparatus of claim 40, comprising means to deliver the counter-resistance gas at a selectable strategic time within the expiratory phase including one of early in exhalation or late in exhalation.

42. The apparatus of claim 40, wherein the counter-resistance gas delivery occurs throughout exhalation.

43. The apparatus of claim 40, comprising means to deliver the counter-resistance gas in an oscillatory pattern.

44. The apparatus of claim 40, comprising means to deliver the counter-resistance gas in a turbulent pattern.

45. The apparatus of claim 40, comprising means to deliver the counter-resistance gas in a laminar pattern.

46. The apparatus of claim 40, wherein the counter-resistance gas delivery dynamics create a substantially uniform velocity profile in the airway.

47. The apparatus of claim 40, wherein the counter-resistance gas delivery dynamics create a substantially non-uniform velocity profile in the airway.

48. The apparatus of claim 1, comprising means, in addition to the primary ventilation gas delivery, to actively remove airway gas from the airway to reduce the $CO_2$ content of gas in the airway.

49. The apparatus of claim 1, wherein the ventilation gas comprises at least one of following: oxygen, or helium-oxygen mixtures, or nitric oxide mixtures, or other therapeutic gases.

50. The apparatus of claim 1, comprising means to deliver a medicant.

51. The apparatus of claim 1, further comprising means to deliver one or more conjunctive therapies and (a) a secondary gas delivery; (b) a delivery of gas during exhalation to cause exhaled flow counter-resistance; (c) a removal of gas from the airway; (d) delivery of a therapeutic gas such as helium-oxygen or nitric oxide; (e) delivery of a medication.

52. The apparatus of claim 51, further comprising means to adjust the conjunctive therapies based on the needs of the patient, wherein the adjustment means can be manual or automatic based on a feedback, and wherein the adjustment means can permit turning the conjunctive therapy on or off or varying the amplitude of the conjunctive therapy.

53. An apparatus for providing ventilatory assistance to a patient wherein a gas volume is delivered into an airway of the patient via a tubing in communication with the airway and wherein the apparatus is adapted such that:
  (a) the gas volume is delivered at a rate in synchrony with the patient's spontaneous breathing and delivered during the patient's inspiratory phase;
  (b) the gas volume delivered is 5-50% of the patient's natural tidal volume;
  (c) a driving pressure in the catheter is 5-25 psi, a peak flow rate of gas delivery is 12-50 liters per minute;
  (d) a gas delivery time is 0.1 to 0.8 seconds;
  (e) an exit speed of gas out of the catheter tip is 25-400 meters per second causing 25-200% volume entrainment; and
  (f) the ventilator is synchronized with the patient's breathing pattern by using a breath sensor in communication with the airway to measure spontaneous airflow.

54. The apparatus of claim 1, comprising means to regulate pressure output from the gas source, an accumulator to accumulate gas at the regulated pressure, an on/off valve for controlling flow output from the accumulator to the patient and the sensor comprises breath sensors to determine the breath phase of the patient.

55. The apparatus of claim 1, wherein the ventilation gas source comprises a compressed oxygen gas canister comprising a regulator wherein the regulator comprises a gas output orifice configured to provide an output of 10-40 psi and greater than 6 liters per minute.

56. The apparatus of claim 1, further comprising a gas accumulator, wherein the accumulator accumulates the volume of gas being delivered to the patient in one breath for each breath delivered.

57. The apparatus of claim 56, wherein the accumulator is a cylinder with a stroking piston.

58. The apparatus of claim 1, further comprising a gas volume accumulator comprising: (a) a cylinder, (b) a stroking piston within the cylinder, (c) an inlet and outlet port on one side of the piston and an spring element on the opposite side of the piston, (d) a valve means to control the filling and emptying of the cylinder, wherein the spring element comprises a spring force sufficient to accelerate the emptying of the gas out of the cylinder to the patient.

59. The apparatus of claim 1, further comprising a gas volume accumulator comprising a cylinder with an internal stroking piston, wherein a geometric volume of the cylinder is adjustable.

60. The apparatus of claim 59, wherein the cylinder volume adjustment means is a moveable end-cap on one end of the cylinder wherein the end-cap slides axially in the inner diameter of the cylinder.

61. The apparatus of claim 59, wherein the cylinder volume adjustment is adjusted manually, for example by rotation of a knob.

62. The apparatus of claim 59, wherein the cylinder volume adjustment is adjusted automatically, for example by use of a motor.

63. The apparatus of claim 59, wherein the cylinder volume adjustment is monitored by use of a position scale, such as an axial scale to determine the position of said end-cap, or a radial scale to determine the position of said knob.

64. The apparatus of claim 59, wherein the cylinder volume adjustment is monitored by use of a position sensor, such as an axial sensor to determine the position of the end-cap, or a radial sensor to determine the position of the knob.

65. The apparatus of claim 1, further comprising valves and control means to shape a ventilation gas delivery profile as desired, such as a sine wave, square wave or accelerating or decelerating wave.

66. The apparatus of claim 1, further comprising a gas accumulator wherein the gas accumulator is shaped non-cylindrically.

67. The apparatus of claim 1, further comprising a gas accumulator wherein the gas accumulator is shaped with a concave curve.

68. The apparatus of claim 1, further comprising a gas accumulator wherein the gas accumulator comprises a bone-shaped cross section.

69. The apparatus of claim 1, further comprising a gas accumulator wherein the gas accumulator comprises an array of separate interconnected cylinders.

70. The apparatus of claim 1, further comprising a gas accumulator wherein the gas accumulator is comprised of tubing.

71. The apparatus of claim 1, wherein a ventilation gas supply reservoir is configured non-cylindrically, such as but not limited to a concave shape, a bone-shaped cross section, an array of interconnected cylinders, or curved conduit.

72. The apparatus of claim 1, wherein the tubing includes a tip that is restricted to provide the desired amount of gas exit speed, typically 50 to 400 meters per second and preferably 100-250 meters per second.

73. The apparatus of claim 72, wherein the tip is restricted to produce the desired amount of entrainment of upper airway air, typically 25-200%.

74. The apparatus of claim 72, wherein the tip restriction is constant.

75. The apparatus of claim 72, wherein the tip restriction is variable.

76. The apparatus of claim 72, wherein the tip restriction is variable wherein the restriction is varied by the use of an adjustable member in the gas flow lumen of the tip.

77. The apparatus of claim 76, wherein the adjustable member adjusts radially to decrease or increase the gas flow lumen diameter.

78. The apparatus of claim 76, wherein the adjustable member axially slides to actuate an increase or decrease in the gas flow lumen diameter.

79. The apparatus of claim 1, wherein the gas flow lumen is restricted to produce an exit speed of typically 50-400 meters per second.

80. The apparatus of claim 79, wherein the gas flow lumen tip diameter is restricted to an inner diameter of 0.5 mm to 2.0 mm.

81. The apparatus of claim 1, comprising a main ventilation gas flow opening at the distal tip to deliver the main ventilation gas toward the lung, and comprising a secondary opening configured to direct delivery of the secondary gas upward toward the larynx.

82. The apparatus of claim 1, comprising gas flow ports near the distal tip wherein the ports are configured to allow gas to exit the tubing multi-directionally, wherein the ports and multidirectional flow is selected to produce a uniform or semi-uniform velocity profile in the airway.

83. The apparatus of claim 1, comprising a generally 360° curve at its end which is inserted into the trachea, wherein the gas delivery lumen is blocked to gas flow at the tip of the tubing, and comprising a gas exit port located on the curved section of the tubing at a location to direct the exiting gas flow toward the lung, and wherein the radius of the curve positions a portion of the curve against the anterior tracheal wall.

84. The apparatus of claim 1, comprising a generally a 540° curve at its end which is inserted into the trachea, wherein the curve positions the tip of the tubing pointing toward the lung, wherein the radius of the curve positions a portion of the curve against the anterior and posterior wall of the trachea.

85. The apparatus of claim 1, comprising an outer cannula sleeve, wherein the outer cannula sleeve comprises a stomal sleeve, and wherein the outer cannula sleeve directs the tip to the center of the trachea.

86. The apparatus of claim 1, comprising (a) a spacer positioned inside the trachea used to space the tubing away from the stomal tissue; (b) a curve configured to a position of the distal section of the tubing against the anterior tracheal wall; (c) a curve to position the tip of the tubing away from the airway wall and directed toward the lungs.

87. The apparatus of claim 1, with a distal section that is inserted into a patient wherein the inserted section is comprised of a soft material of 20-80 Shore A and further comprising a rigid member imbedded into the construction to provide the soft material semi-rigidity.

88. The apparatus of claim 87, wherein the rigid member is a spring material.

89. The apparatus of claim 87, wherein the rigid member is a shape memory alloy material.

90. The apparatus of claim 87, wherein the rigid member is a malleable material.

91. The apparatus of claim 1, wherein the catheter comprises thermally responsive material in its construction which causes a change from a first shape to a second shape of the tubing when reaching body temperature, wherein the first shape is configured to aide in insertion of the tubing and the second shape is configured to aide in atraumatic positioning of the tubing in the airway and to direct the gas exit of the catheter to the lungs.

92. The apparatus of claim 1, wherein a patient end of the tubing is configured to connect to a standard 15 mm connector a tracheal tube, such as a tracheostomy tube or laryngectomy tube, and comprising a sensor extension that extends into the shaft of the tracheal tube or beyond the distal tip of the tracheal tube.

93. The apparatus of claim 1, comprising at its distal tip a radially expandable or compressible basket configured to anchor the tubing in the airway and position the tip of the tubing generally in the center of the airway.

94. The apparatus of claim 1, comprising a outer diameter mating stomal sleeve configured for insertion into the stomal tract and for insertion of the tubing through the sleeve, wherein the sleeve further comprises a spacer on its distal end configured to position the catheter tip away from the anterior tracheal wall.

95. The apparatus of claim 1, comprising: (a) a distal section inserted into the trachea wherein the distal inserted section comprises a generally 90° curve to position the tip the tubing to be pointing toward the lungs; (b) an flange placed on the tubing shaft positioned outside the patient comprising means to axially adjust the placement of the flange on the catheter shaft and comprising means to lock the axial position of flange on the catheter shaft; (c) length markings on the tubing shaft to correspond to the flange position.

96. The apparatus of claim 1, comprising a compressible member for sealing with and securing to the stomal tract.

97. The apparatus of claim 1, comprising a signal element recognizable by the ventilator, wherein the signal element defines a therapeutic attribute of the tubing, such as patient compatibility, intended disease state, or length of usage of therapy by the patient, and wherein the ventilator comprises the ability to recognize the signal element and alter its output based on the signal.

98. The apparatus of claim 1, wherein the breath sensor comprises two sensors wherein a first sensor is a negative coefficient thermistor and a second sensor is a positive coefficient thermistor.

99. The apparatus of claim 1, wherein the breath sensor comprises two pair of thermistors, wherein each pair is connected to a wheatstone bridge circuit, and wherein one pair of thermistors are negative coefficient thermistors and the second pair of thermistors are positive coefficient thermistors.

100. The apparatus of claim 1, wherein the breath sensor comprises at least two thermistors, wherein at least one thermistor is located on the surface of the tubing facing the larynx and at least one thermistor is located on the surface of the tubing facing the lungs.

101. The apparatus of claim 1, wherein the tubing comprises dimensions of 0.5-15 cm insertion length, 20-200 cm overall length, working inner diameter of 2.0-4.0 mm, nozzle diameter at tip of tubing of 0.7-1.0 mm, and outer diameter of insertion section of 2.0-6.5 mm.

102. A method for providing ventilatory assistance to a patient, comprising the steps of:
  (a) delivering a gas volume into the airway via a tubing in communication with a patient airway;
  (b) synchronizing the delivery volume to a rate synchronized with the patient's spontaneous breathing;
  (c) delivering the delivery volume during the patient's inspiratory phase;
  (d) providing the gas volume by a wearable ventilator;
  (e) synchronizing the ventilator with the patient's breathing pattern by using a breath sensor in communication with the patient's airway to measure spontaneous airflow.

103. The method of claim 102, wherein the ventilation gas volume delivered is 5-50% of the patient's natural tidal volume.

104. The method of claim 102, wherein the ventilation gas driving pressure is 5-25 psi.

105. The method of claim 102, wherein the ventilation peak flow rate delivery is 12-50 liters per minute.

106. The method of claim 102, wherein the ventilation gas delivery time is 0.1 to 0.8 seconds.

107. The method of claim 102, wherein the ventilation gas exit speed out of the catheter tip is 25-400 meters per second.

108. The method of claim 102, wherein the ventilation gas exit airflow dynamics are selected to cause 25-200% volume entrainment of gas from the upper airway into the lung with the ventilation gas.

109. The method of claim 102, wherein the ventilation gas delivery amplitude is selected to cause a less negative pressure in the patient's lung during inspiration compared to the negative pressure during un-assisted breathing.

110. The method of claim 102, wherein the ventilation gas delivery amplitude is selected to cause a positive pressure in the patient's lung during inspiration compared to the negative pressure during un-assisted breathing.

111. The method of claim 102, wherein the breath sensor comprises two individual sensors used to obtain a comparison between the two individual sensors wherein the comparison is used to compensate for drifts and signal artifacts.

112. The method of claim 102, wherein the individual sensor comparison is differentiated to correlate the signal to different parts of the breathing curve.

113. The method of claim 102, wherein a liquid oxygen system is used as the ventilation gas source.

114. The method of claim 102, wherein a compressed oxygen gas source is used as the ventilation gas source.

115. The method of claim 102, wherein an oxygen generating system is used as the ventilation gas source.

116. The method of claim 102, wherein a supply volume of oxygen rich gas is integrated into the ventilator.

117. The method of claim 102, wherein the ventilation gas is delivered after the inspiratory flow rate reaches its peak amplitude.

118. The method of claim 102, wherein the ventilation gas is delivered after the respiratory muscles reach their maximum work.

119. The method of claim 102, wherein the ventilation gas is delivered in multiple pulses during inspiration.

120. The method of claim 102, wherein the ventilation gas is delivery is adjustable to occur at any time within the inspiratory phase, depending on the comfort and ventilatory needs of the patient, wherein the time in the inspiratory phase is determined by information from the breath sensor.

121. The method of claim 120, wherein the adjustment is made automatically by a physiological feedback mechanism.

122. The method of claim 121, wherein the feedback mechanism is based on airway gas concentrations.

123. The method of claim 121, wherein the feedback mechanism is based on depth of breathing.

124. The method of claim 121, wherein the feedback mechanism is based on rate of breathing.

125. The method of claim 121, wherein the feedback mechanism is based on pulse oximetry.

126. The method of claim 120, wherein the adjustment is made manually by the user.

127. The method of claim 120, wherein the adjustment is made by the patient.

128. The method of claim 120, wherein the adjustment is made by the clinician.

129. The method of claim 102, wherein in addition to the primary ventilation gas delivery, a delivery of secondary ventilation gas comprising a lower gas flow rate compared to the primary ventilation gas delivery, is delivered.

130. The method of claim 129, wherein the secondary ventilation gas is delivered early in inspiration.

131. The method of claim 129, wherein the secondary ventilation gas is delivered throughout inspiration.

132. The method of claim 129, wherein the secondary ventilation gas is delivered during exhalation.

133. The method of claim 129, wherein the secondary ventilation gas displaces CO2 in the upper airway, such that the primary ventilation gas when delivered entrains air from the upper airway into the lower airways, wherein the entrained air is low in CO2, at least 2% lower in CO2 compared to when the secondary ventilation gas is turned off.

134. The method of claim 129, wherein the secondary ventilation gas comprises a high oxygen concentration, such as 50%-100%, and the primary ventilation gas comprises a lower oxygen concentration, such as 21%-60%.

135. The method of claim 102, wherein the pressure or flow rate amplitude of the ventilation gas delivery is adjustable.

136. The method of claim 102, wherein the ventilation gas delivery pressure of flow rate waveform is shaped into a desired waveform, such as a sine wave, an ascending wave, a descending wave or a square wave.

137. The method of claim 102, wherein in addition to the primary ventilation gas delivery, gas is delivered into the airway during exhalation to provide a counter-resistance to exhaled flow, wherein the counter-resistance gas flow dynamics are selected to reduce airway collapse.

138. The method of claim 137, wherein the counter-resistance gas delivery occurs at a strategic time within the expiratory phase, for example early in exhalation or late in exhalation.

139. The method of claim 137, wherein the counter-resistance gas delivery occurs throughout exhalation.

140. The method of claim 137, wherein the counter-resistance gas delivery dynamics are oscillatory.

141. The method of claim 137, wherein the counter-resistance gas delivery dynamics are turbulent.

142. The method of claim 137, wherein the counter-resistance gas delivery dynamics are laminar.

143. The method of claim 137, wherein the counter-resistance gas delivery dynamics create a substantially uniform velocity profile in the airway.

144. The method of claim 137, wherein the counter-resistance gas delivery dynamics create a substantially non-uniform velocity profile in the airway.

145. The method of claim 102, wherein in addition to the primary ventilation gas delivery, airway gas is actively removed from the airway to reduce the CO2 content of gas in the airway.

146. The method of claim 102, wherein the ventilation gas may comprise oxygen, or helium-oxygen mixtures, or nitric oxide mixtures.

147. The method of claim 102, wherein a medicant is delivered to the patient during.

148. The method of claim 102, further comprising in addition one or more of the conjunctive therapies: (a) a secondary gas delivery; (b) a delivery of gas during exhalation to cause exhaled flow counter-resistance; (c) a removal of gas from the airway; (d) delivery of a therapeutic gas such as helium-oxygen or nitric oxide; (e) delivery of a medication.

149. The method of claim 148, further wherein the conjunctive therapies are adjustable based on the needs of the patient, wherein the adjustment can be manual or automatic based on a feedback, and wherein the adjustment can be on or off or varying the amplitude.

150. A method for providing ventilatory assistance to a patient wherein a gas volume is delivered to the airway via a tubing in communication with the airway and wherein: (a) the volume is delivered at a rate in synchrony with the patient's spontaneous breathing and delivered during the patient's inspiratory phase; (b) the volume delivered is 5-50% of the patient's natural tidal volume; (c) the driving pressure in the tubing is 5-25 psi, the peak flow rate of gas delivery 12-50 liters per minute; (d) the gas delivery time is 0.1 to 0.8 seconds; (e) the exit speed of gas out of the tip is 25-400 meters per second causing 25-200% volume entrainment; and (f) the ventilator is synchronized with the patient's breathing pattern by using a breath sensor in communication with the airway of the patient to measure tracheal airflow.

151. The apparatus of claim 1, wherein the tubing is a catheter adapted to be indwelling in the patient's airway.

152. The apparatus of claim 1, wherein the breath sensor is adapted to measure spontaneous airflow directly in the patient's airway.

153. The apparatus of claim 1, further comprising a means for adjusting the ventilation gas delivery to occur at any tine within the inspiratory phase.

154. The apparatus of claim 153, wherein the adjustment means is capable of adjusting the ventilation gas delivery automatically by a physiological feedback mechanism.

* * * * *